(12) United States Patent
Boulter et al.

(10) Patent No.: US 9,156,903 B2
(45) Date of Patent: *Oct. 13, 2015

(54) HIGH AFFINITY NY-ESO T CELL RECEPTORS

(75) Inventors: Jonathan Michael Boulter, Oxfordshire (GB); Bent Karsten Jakobsen, Oxfordshire (GB); Yi Li, Oxfordshire (GB); Peter Eamon Molloy, Oxfordshire (GB); Steven Mark Dunn, Oxfordshire (GB)

(73) Assignee: ADAPTIMMUNE LIMITED, Oxford (GB)

( * ) Notice: Subject to any disclaimer, the term of this patent is extended or adjusted under 35 U.S.C. 154(b) by 141 days.

This patent is subject to a terminal disclaimer.

(21) Appl. No.: 13/429,944

(22) Filed: Mar. 26, 2012

(65) Prior Publication Data

US 2013/0058908 A1   Mar. 7, 2013

Related U.S. Application Data

(63) Continuation of application No. 11/596,458, filed as application No. PCT/GB2005/001924 on May 18, 2005, now Pat. No. 8,143,376.

(30) Foreign Application Priority Data

May 19, 2004  (GB) .................................. 0411123.3
Sep. 3, 2004  (GB) .................................. 0419643.2

(51) Int. Cl.
  C07K 1/00    (2006.01)
  C07K 14/00   (2006.01)
  C07K 17/00   (2006.01)
  C07K 14/725  (2006.01)
  C07K 14/705  (2006.01)
  A61K 35/12   (2015.01)
  A61K 38/00   (2006.01)

(52) U.S. Cl.
  CPC ........... *C07K 14/7051* (2013.01); *C07K 14/705* (2013.01); *A61K 35/12* (2013.01); *A61K 38/00* (2013.01)

(58) Field of Classification Search
  None
  See application file for complete search history.

(56) References Cited

U.S. PATENT DOCUMENTS

6,811,785 B2    11/2004  Brumeanu et al.
2002/0058253 A1  5/2002  Kranz et al.
2011/0014169 A1  1/2011  Boulter

FOREIGN PATENT DOCUMENTS

WO    WO 03/020763    3/2003

OTHER PUBLICATIONS

Abbas, et al., Cellular and Molecular Immunology, 3rd ed., W.B. Saunders Co., Philadelphia (1997) p. 106.
Jager, et al., Simultaneous Humoral and Cellular Immune Response Against Cancer-Testis Antigen NY-ESP-1: Definition of Human Histocompatability Leukocyte Antigen (HLA)-A2-Binding Peptide Epitopes, The Journal of Experimental Medicine (1998) vol. 187, No. 2, p. 265-270.
Li, et al., Directed Evolution of Human T-Cell Receptors With Picomolar Affinities by Phage Display, Nature Biotechnology (2005) vol. 23, No. 3, p. 349-354.
Manning, et al., J. Exp. Med. (1999) vol. 189, p. 461-470.
Marsh, et al., The HLA Factsbook (2000) Academic Press, San Diego, 109-110, p. 20-23.
Morgan, et al., Cancer Regression in Patients After Transfer of Genetically Engineered Lymphocytes, Science (2006) vol. 314, p. 126-129.
Office Action mailed Nov. 23, 2010 in U.S. Appl. No. 12/854,691.
Pardoll, et al., Tumor Reactive T Cells Get a Boost, Nature Biotechnology (2002) vol. 20, p. 1207-1208.
Pierce, et al., Biochem. (2010) vol. 49, p. 7050-7059.
Wang, et al., A Systematic Assessment of MHC Class II Peptide Binding Predictions and Evaluation of a Consensus Approach, PLoS Comput Biol. (2008) vol. 4, Issue 4: e1000048.

*Primary Examiner* — Amy Juedes
(74) *Attorney, Agent, or Firm* — Vedder Price P.C.; Thomas J. Kowalski; Deborah L. Lu

(57) ABSTRACT

The present invention provides T cell receptors (TCRs) having the property of binding to SLLMWITQC-HLA-A*0201, the SLLMWITQC SEQ ID NO:126 peptide being derived from the NY-ESO-1 protein which is expressed by a range of tumor cells. The TCRs have a $K_D$ for the said peptide-HLA complex of less than or equal to 1 μM and/or have an off-rate $(k_{off})$ of $1 \times 10^{-3}$ $S^{-1}$ or slower.

9 Claims, 41 Drawing Sheets

(SEQ ID No: 1)

Figure 1b

```
                10                      20
                *                       *
    M G V T Q T P K F Q V L K T G Q S M T L Q C A Q D M N H E 30                      40                      50
    *                       *                       *
    Y M S W Y R Q D P G M G L R L I H Y S V G A G I T D Q G E 60                      70                      80
        *                       *                       *
    V P N G Y N V S R S T T E D F P L R L L S A A P S Q T S V 90                      100                     110
            *                       *                       *
    Y F C A S S Y V G N T G E L F F G E G S R L T V L
```
(SEQ ID No: 2)

Figure 2a atgcaggaggtgacacagattcctgcagctctgagtgtcccagaaggagaaaacttggttctcaactgcagtttcactgatag
cgctatttacaacctccagtggtttaggcaggaccctgggaaaggtctcacatctctgttgcttattcagtcaagtcagagaga
gcaaacaagtggaagacttaatgcctcgctggataaatcatcaggacgtagtactttatacattgcagcttctcagcctggtga
ctcagccacctacctctgtgctgtgaggcccacatcaggaggaagctacatacctacatttggaagaggaaccagccttatt
gttcatccgtatatccagaaccctgaccctgccgtgtaccagctgagagactctaaatccagtgacaagtctgtctgcctattc
accgattttgattctcaaacaaatgtgtcacaaagtaaggattctgatgtgtatatcacagacaaaactgtgctagacatgaggt
ctatggacttcaagagcaacagtgctgtggcctggagcaacaaatctgactttgcatgtgcaaacgccttcaacaacagcatt
attccagaagacaccttcttccccagcccagaaagttcctaa (SEQ ID No: 3)

Figure 2b atgggtgtcactcagaccccaaaattccaggtcctgaagacaggacagagcatgacactgcagtgtgcccaggatatgaac
catgaatacatgtcctggtatcgacaagacccaggcatggggctgaggctgattcattactcagttggtgctggtatcactga
ccaaggagaagtccccaatggctacaatgtctccagatcaaccacagaggatttcccgctcaggctgctgtcggctgctccc
tcccagacatctgtgtacttctgtgccagcagttacgtcgggaacaccggggagctgttttttggagaaggctctaggctgac
cgtactggaggacctgaaaaacgtgttcccacccgaggtcgctgtgtttgagccatcagaagcagagatctcccacaccca
aaaggccacactggtgtgcctggccacaggcttctaccccgaccacgtggagctgagctggtgggtgaatgggaaggag
gtgcacagtggggtcagcacagacccgcagcccctcaaggagcagcccgccctcaatgactccagatacgctctgagca
gccgcctgagggtctcggccaccttctggcaggaccccgcaaccacttccgctgtcaagtccagttctacgggctctcgg
agaatgacgagtggacccaggatagggccaaacccgtcacccagatcgtcagcgccgaggcctggggtagagcagact
aa
(SEQ ID No: 4)

(SEQ ID No: 5)

(SEQ ID No: 6)

Figure 4a atgcaggaggtgacacagattcctgcagctctgagtgtcccagaaggagaaaacttggttctcaactgcagtttcactgatag
cgctatttacaacctccagtggtttaggcaggaccctgggaaaggtctcacatctctgttgcttattcagtcaagtcagagaga
gcaaacaagtggaagacttaatgcctcgctggataaatcatcaggacgtagtactttatacattgcagcttctcagcctggtga
ctcagccacctacctctgtgctgtgaggcccacatcaggaggaagctacatacctacatttggaagaggaaccagccttatt
gttcatccgtatatccagaaccctgaccctgccgtgtaccagctgagagactctaaatccagtgacaagtctgtctgcctattc
accgattttgattctcaaacaaatgtgtcacaaagtaaggattctgatgtgtatatcacagacaaatgtgtgctagacatgaggt
ctatggacttcaagagcaacagtgctgtggcctggagcaacaaatctgactttgcatgtgcaaacgccttcaacaacagcatt
attccagaagacaccttcttccccagcccagaaagttcctaa
(SEQ ID No: 7)

Figure 4b atgggtgtcactcagaccccaaaattccaggtcctgaagacaggacagagcatgacactgcagtgtgcccaggatatgaac
catgaatacatgtcctggtatcgacaagacccaggcatggggctgaggctgattcattactcagttggtgctggtatcactga
ccaaggagaagtccccaatggctacaatgtctccagatcaaccacagaggatttcccgctcaggctgctgtcggctgctccc
tcccagacatctgtgtacttctgtgccagcagttacgtcgggaacaccggggagctgttttttggagaaggctctaggctgac
cgtactggaggacctgaaaaacgtgttcccacccgaggtcgctgtgtttgagccatcagaagcagagatctcccacaccca
aaaggccacactggtgtgcctggccacaggcttctaccccgaccacgtggagctgagctggtgggtgaatgggaaggag
gtgcacagtggggtctggacagacccgcagcccctcaaggagcagcccgccctcaatgactccagatacgctctgagca
gccgcctgagggtctcggccaccttctggcaggaccccgcaaccacttccgctgtcaagtccagttctacgggctctcgg
agaatgacgagtggacccaggatagggccaaacccgtcacccagatcgtcagcgccgaggcctggggtagagcagact
aa
(SEQ ID No: 8)

Figure 5a

```
M Q E V T Q I P A A L S V P E G E N L V L N C S F T D S A I Y N L Q W
F R Q D P G K G L T S L L L I Q S S Q R E Q T S G R L N A S L D K S S
G R S T L Y I A A S Q P G D S A T Y L C A V R P T S G G S Y I P T F G
R G T S L I V H P Y I Q N P D P A V Y Q L R D S K S S D K S V C L F T
D F D S Q T N V S Q S K D S D V Y I T D K G V L D M R S M D F K S N S
A V A W S N K S D F A C A N A F N N S I I P E D T F F P S P E S S
```
(SEQ ID No: 9)

Figure 5b

```
M G V T Q T P K F Q V L K T G Q S M T L Q C A Q D M N H E Y M S W Y R
Q D P G M G L R L I H Y S V G A G I T D Q G E V P N G Y N V S R S T T
E D F P L R L L S A A P S Q T S V Y F C A S S Y V G N T G E L F F G E
G S R L T V L E D L K N V F P P E V A V F E P S E A E I S H T Q K A T
L V C L A T G F Y P D H V E L S W W V N G K E V H S G V G T D P Q P L
K E Q P A L N D S R Y A L S S R L R V S A T F W Q D P R N H F R C Q V
Q F Y G L S E N D E W T Q D R A K P V T Q I V S A E A W G R A D
```
(SEQ ID No: 10)

Figure 6

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPLLDGTYIPTFGRGTSLIVHPY
(SEQ ID No: 11)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRHTSNGYFPPTFGRGTSLIVHPY
(SEQ ID No: 12)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPMTGGTYIPTFGRGTSLIVHPY
(SEQ ID No: 13)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPLYGGTYIPTFGRGTSLIVHPY
(SEQ ID No: 14)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPMIGGTYIPTFGRGTSLIVHPY
(SEQ ID No: 15)

Figure 6 (continued)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPLTGGTYIPTFGRGTSLIVHPY
(SEQ ID No: 16)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPLTGGSYIPTFGRGTSLIVHPY
(SEQ ID No: 17)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPATGGTYIPTFGRGTSLIVHPY
(SEQ ID No: 18)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPQTVPTYIPTFGRGTSLIVHPY
(SEQ ID No: 19)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPMSGGTYIPTFGRGTSLIVHPY
(SEQ ID No: 20)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPYQSGHYMPTFGRGTSLIVHPY
(SEQ ID No: 21)

Figure 6 (continued)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPTSGG_D_Y_T_PTFGRGTSLIVHPY
(SEQ ID No: 22)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP_ML_GG_T_YIPTFGRGTSLIVHPY
(SEQ ID No: 23)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP_LQD_G_T_YIPTFGRGTSLIVHPY
(SEQ ID No: 24)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP_MTDS_TYIPTFGRGTSLIVHPY
(SEQ ID No: 25)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP_LVDPT_YIPTFGRGTSLIVHPY
(SEQ ID No: 26)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP_EVDAT_YIPTFGRGTSLIVHPY
(SEQ ID No: 27)

Figure 6 (continued)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPLEDSTYIPTFGRGTSLIVHPY
(SEQ ID No: 28)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPLVGGVYIPTFGRGTSLIVHPY
(SEQ ID No: 29)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGGNYIPTFGRGTSLIVHPY
(SEQ ID No: 30)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTTGGSYIPTFGRGTSLIVHPY
(SEQ ID No: 31)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPISGGSYIPTFGRGTSLIVHPY
(SEQ ID No: 32)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPMSGGSYIPTFGRGTSLIVHPY
(SEQ ID No: 33)

Figure 6 (continued)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP<u>MT</u>GGSYIPTFGRGTSLIVHPY
(SEQ ID No: 34)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP<u>I</u>SGGSYIPTFGRGTSLIVHPY
(SEQ ID No: 35)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPTSGG<u>T</u>YIPTFGRGTSLIVHPY
(SEQ ID No: 36)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPT<u>A</u>GGSYIP<u>A</u>FGRGTSLIVHPY
(SEQ ID No: 37)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP<u>A</u>GGSYIPTFGRGTSLIVHPY
(SEQ ID No: 38)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRP<u>AT</u>GGSYIPTFGRGTSLIVHPY
(SEQ ID No: 39)

Figure 6 (continued)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPT-QYTQVPTFGRGTSLIVHPY
(SEQ ID No: 40)

MQEVTQIPAALSVPEGENLALNCSFTDSAIYNLQWFRQ
DPGKGLTSLLIQPSQREQTSGRLNASLDKSSGRSTLYI
AASQPGDSATYLCAVRPTSGGSYIPTFGRGTSLIVHPY
(SEQ ID No: 41)

MQEVTQIPAALSVPEGENLVLNCSFTDSAIYNLQWFRQ
DPGKGLTSLLIPFWQREQTSGRLNASLDKSSGRSTLYI
AASQPGDSATYLCAVRPTSGGSYIPTFGRGTSLIVHPY
(SEQ ID No: 42)

MQEVTQIPAALSVPEGENLVLNCSFTDSAIYNLQWFRQ
DPGKGLTSLLISPWQREQTSGRLNASLDKSSGRSTLYI
AASQPGDSATYLCAVRPTSGGSYIPTFGRGTSLIVHPY
(SEQ ID No: 43)

MQEVTQIPAALSVPEGENLVLNCSFTDSAIYNLQWFRQ
DPGKGLTSLLITPWQREQTSGRLNASLDKSSGRSTLYI
AASQPGDSATYLCAVRPTSGGSYIPTFGRGTSLIVHPY
(SEQ ID No: 44)

MQEVTQIPAALSVPEGENLVLNCSFTDSAIYNLQWFRQ
DPGKGLTSLLIQGWQREQTSGRLNASLDKSSGRSTLYI
AASQPGDSATYLCAVRPTSGGSYIPTFGRGTSLIVHPY
(SEQ ID No: 45)

Figure 6 (continued)

MQEVTQIPAALSVPEGENLVLNCSFTDSAIYNLQWFRQ
DPGKGLTSLLLI<u>MGH</u>QREQTSGRLNASLDKSSGRSTLYI
AASQPGDSATYLCAVRPTSGGSYIPTFGRGTSLIVHPY
(SEQ ID No: 46)

MQEVTQIPAALSVPEGENLVLNCSFTDSAIYNLQWFRQ
DPGKGLTSLLLI<u>MGT</u>QREQTSGRLNASLDKSSGRSTLYI
AASQPGDSATYLCAVRPTSGGSYIPTFGRGTSLIVHPY
(SEQ ID No: 47)

MQEVTQIPAALSVPEGENLVLNCSFTDSAIYNLQWFRQ
DPGKGLTSLLLI<u>PFW</u>QREQTSGRLNASLDKSSGRSTLYI
AASQPGDSATYLCAVRP<u>LLD</u>G<u>T</u>YIPTFGRGTSLIVHPY
(SEQ ID No: 48)

MQEVTQIPAALSVPEGENLVLNCSFTDSAIYNLQWFRQ
DPGKGLTSLLLI<u>TPW</u>QREQTSGRLNASLDKSSGRSTLYI
AASQPGDSATYLCAVRP<u>LLD</u>G<u>T</u>YIPTFGRGTSLIVHPY
(SEQ ID No: 49)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>LLD</u>G<u>T</u>YIPTFGRGTSLIVHPY
(SEQ ID No: 50)

MQEVTQIPAALSVPEGENLVLNCSFTDSAIYNLQWFRQ
DPGKGLTSLLLI<u>MGH</u>QREQTSGRLNASLDKSSGRSTLYI
AASQPGDSATYLCAVRP<u>LLD</u>G<u>T</u>YIPTFGRGTSLIVHPY
(SEQ ID No: 51)

Figure 6 (continued)

MQEVTQIPAALSVPEGENLVLNCSFTDSAIYNLQWFRQ
DPGKGLTSLLLI<u>MGT</u>QREQTSGRLNASLDKSSGRSTLYI
AASQPGDSATYLCAVRP<u>LLD</u>G<u>T</u>YIPTFGRGTSLIVHPY
(SEQ ID No: 52)

MQEVTQIPAALSVPEGENLVLNCSFTDSAIYNLQWFRQ
DPGKGLTSLLLI<u>MGW</u>QREQTSGRLNASLDKSSGRSTLYI
AASQPGDSATYLCAVRP<u>LLD</u>G<u>T</u>YIPTFGRGTSLIVHPY
(SEQ ID No: 53)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>LR</u>GGSYIPTFGRGTSLIVHPY
(SEQ ID No: 54)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>NDGSG</u>SYIPTFGRGTSLIVHPY
(SEQ ID No: 55)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>AW</u>GG<u>N</u>YIPTFGRGTSLIVHPY
(SEQ ID No: 56)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>AE</u>GG<u>E</u>YIPTFGRGTSLIVHPY
(SEQ ID No: 57)

Figure 6 (continued)

MQEVTQIPAALSVPEGENLVLNCSFTDSAIYNLQWFRQ
DPGKGLTSLLLI<u>SP</u><u>W</u>QREQTSGRLNASLDKSSGRSTLYI
AASQPGDSATYLCAVRP<u>FT</u>GG<u>G</u>YIPTFGRGTSLIVHPY
(SEQ ID No: 58)

MQEVTQIPAALSVPEGENLVLNCSFTDSAIYNLQWFRQ
DPGKGLTSLLLI<u>SP</u><u>W</u>QREQTSGRLNASLDKSSGRSTLYI
AASQPGDSATYLCAVRP<u>V</u>SGG<u>D</u>YIPTFGRGTSLIVHPY
(SEQ ID No: 59)

MQEVTQIPAALSVPEGENLVLNCSFTDSAIYNLQWFRQ
DPGKGLTSLLLI<u>SP</u><u>W</u>QREQTSGRLNASLDKSSGRSTLYI
AASQPGDSATYLCAVRP<u>LDDGR</u>YIPTFGRGTSLIVHPY
(SEQ ID No: 60)

MQEVTQIPAALSVPEGENLVLNCSFTDSAIYNLQWFRQ
DPGKGLTSLLLI<u>SP</u><u>W</u>QREQTSGRLNASLDKSSGRSTLYI
AASQPGDSATYLCAVRP<u>NT</u>GG<u>Q</u>YIPTFGRGTSLIVHPY
(SEQ ID No: 61)

MQEVTQIPAALSVPEGENLVLNCSFTDSAIYNLQWFRQ
DPGKGLTSLLLI<u>SP</u><u>W</u>QREQTSGRLNASLDKSSGRSTLYI
AASQPGDSATYLCAVRP<u>IA</u>GG<u>K</u>YIPTFGRGTSLIVHPY
(SEQ ID No: 62)

MQEVTQIPAALSVPEGENLVLNCSFTDSAIYNLQWFRQ
DPGKGLTSLLLI<u>SP</u><u>W</u>QREQTSGRLNASLDKSSGRSTLYI
AASQPGDSATYLCAVRP<u>GT</u>GG<u>D</u>YIPTFGRGTSLIVHPY
(SEQ ID No: 63)

Figure 6 (continued)

MQEVTQIPAALSVPEGENLVLNCSFTDSAIYNLQWFRQ
DPGKGLTSLLLI<u>SP</u>W<u></u>QREQTSGRLNASLDKSSGRSTLYI
AASQPGDSATYLCAVRP<u>AA</u>GGS<u>D</u>IPTFGRGTSLIVHPY
(SEQ ID No: 64)

MQEVTQIPAALSVPEGENLVLNCSFTDSAIYNLQWFRQ
DPGKGLTSLLLI<u>SP</u>W<u></u>QREQTSGRLNASLDKSSGRSTLYI
AASQPGDSATYLCAVRP<u>L</u>AGG<u>A</u>YIPTFGRGTSLIVHPY
(SEQ ID No: 65)

MQEVTQIPAALSVPEGENLVLNCSFTDSAIYNLQWFRQ
DPGKGLTSLLLI<u>SP</u>W<u></u>QREQTSGRLNASLDKSSGRSTLYI
AASQPGDSATYLCAVRP<u>AR</u>GG<u>D</u>YIPTFGRGTSLIVHPY
(SEQ ID No: 66)

MQEVTQIPAALSVPEGENLVLNCSFTDSAIYNLQWFRQ
DPGKGLTSLLLI<u>SP</u>W<u></u>QREQTSGRLNASLDKSSGRSTLYI
AASQPGDSATYLCAVRP<u>L</u>GGG<u>I</u>YIPTFGRGTSLIVHPY
(SEQ ID No: 67)

MQEVTQIPAALSVPEGENLVLNCSFTDSAIYNLQWFRQ
DPGKGLTSLLLI<u>SP</u>W<u></u>QREQTSGRLNASLDKSSGRSTLYI
AASQPGDSATYLCAVRP<u>M</u>GG<u>R</u>YIPTFGRGTSLIVHPY
(SEQ ID No: 68)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>SV</u>GG<u>N</u>YIPTFGRGTSLIVHPY
(SEQ ID No: 69)

Figure 6 (continued)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPATGGNYIPTFGRGTSLIVHPY
(SEQ ID No: 70)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPLTGGAYIPTFGRGTSLIVHPY
(SEQ ID No: 71)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPRESGNYIPTFGRGTSLIVHPY
(SEQ ID No: 72)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPISGGDYIPTFGRGTSLIVHPY
(SEQ ID No: 73)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPAHNGNYIPTFGRGTSLIVHPY
(SEQ ID No: 74)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPDNTWGTYIPTFGRGTSLIVHPY
(SEQ ID No: 75)

Figure 6 (continued)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPVEGDYIPTFGRGTSLIVHPY
(SEQ ID No: 76)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPAASGNYIPTFGRGTSLIVHPY
(SEQ ID No: 77)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPISGGEYIPTFGRGTSLIVHPY
(SEQ ID No: 78)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPITGGGYIPTFGRGTSLIVHPY
(SEQ ID No: 79)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPLKGAYIPTFGRGTSLIVHPY
(SEQ ID No: 80)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPAEGGSYIPTFGRGTSLIVHPY
(SEQ ID No: 81)

Figure 6 (continued)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPSTGGNYIPTFGRGTSLIVHPY
(SEQ ID No: 82)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPVDDGKYIPTFGRGTSLIVHPY
(SEQ ID No: 83)

Figure 7

MGVTQTPKFQVLKTGQSMTLQCAQDMNHEYMSWYRQ
DPGMGLRLIHYSVGAGTTDREVPNGYNVSRSTIEDFPL
RLLSAAPSQTSVYFCASSYLGNTGELFFGEGSRLTVL
(SEQ ID No: 84)

MGVTQTPKFQVLKTGQSMTLQCAQDMNHEYMSWYRQ
DPGMGLRLIHYSVGAGTTDQGEVPNGYNVSRSTIEDFP
LRLLSAAPSQTSVYFCASSYLGNTGELFFGEGSRLTVL
(SEQ ID No: 85)

MGVTQTPKFQVLKTGQSMTLQCAQDMNHEYMSWYRQ
DPGMGLRLIHYSVGAGTTDQGEVPNGYNVSRSTTEDFP
LRLLSAAPSQTSVYFCASSNVGNTGELFFGEGSRLTVL
(SEQ ID No: 86)

MGVTQTPKFQVLKTGQSMTLQCAQDMNHEYMSWYRQ
DPGMGLRLIHYSVGAGTTDQGEVPNGYNVSRSTTEDFP
LRLLSAAPSQTSVYFCASSYVGGTGELFFGEGSRLTVL
(SEQ ID No: 87)

MGVTQTPKFQVLKTGQSMTLQCAQDMNHEYMSWYRQ
DPGMGLRLIHYSVGAITDQGEVPNGYNVSRSTIEDFPL
RLLSAAPSQTSVYFCASSYVGNTGELFFGEGSRLTVL
(SEQ ID No: 88)

Figure 7 (continued)

MGVTQTPKFQVLKTGQSMTLQCAQDMNHEYMSWYRQ
DPGMGLRLIHYSVGAITDQGEVPNGYNVSRSTTEDFP
LRLLSAAPSQTSVYFCASSYLGDTGELFFGEGSRLTVL
(SEQ ID No: 89)

MGVTQTPKFQVLKTGQSMTLQCAQDMNHEYMSWYRQ
DPGMGLRLIHYSVGVGTTDQGEVPNGYNVSRSTTEDFP
LRLLSAAPSQTSVYFCASSYLGDTGELFFGEGSRLTVL
(SEQ ID No: 90)

MGVTQTPKFQVLKTGQSVTLQCAQDMNHEYMSWYRQ
DPGMGLRLIHYSVGVGTTDQGEVPNGYNVSRSTTEDFP
LRLLSAAPSQTSVYFCASSYLGDTGELFFGEGSRLTVL
(SEQ ID No: 91)

MGVTQTPKFQVLKTGQSMTLQCAQDMNHEYMSWYRQ
DPGMGLRLIHYSVSVGMTDQGEVPNGYNVSRSTTEDFP
LRLLSAAPSQTSVYFCASSYVGNTGELFFGEGSRLTVL
(SEQ ID No: 92)

MGVTQTPKFQVLKTGQSMTLQCAQDMNHEYMSWYRQ
DPGMGLRLIHYSVAIQTDQGEVPNGYNVSRSTTEDFPL
RLLSAAPSQTSVYFCASSYVGNTGELFFGEGSRLTVL
(SEQ ID No: 93)

MGVTQTPKFQVLKTGQSMTLQCAQDMNHEYMSWYRQ
DPGMGLRLIHYSVAIQTDQGEVPNGYNVSRSTI EDFPL
RLLSAAPSQTSVYFCASSYLGNTGELFFGEGSRLTVL
(SEQ ID No: 94)

Figure 7 (continued)

MGVTQTPKFQVLKTGQSMTLQCAQDMNHEYMSWYRQ
DPGMGLRLIHYSV<u>SV</u>G<u>M</u>TDQGEVPNGYNVSRSTI<u></u>EDFP
LRLLSAAPSQTSVYFCASSY<u>L</u>GNTGELFFGEGSRLTVL
(SEQ ID No: 95)

MGVTQTPKFQVLKTGQSMTLQCAQDMNHEYMSWYRQ
DPGMGLRLIHYSVGAG<u>T</u>TD<u>R</u>GEVPNGYNVSRSTI<u></u>EDFPL
RLLSAAPSQTSVYFCASSYVGTGELFFGEGSRLTVL
(SEQ ID No: 96)

MGVTQTPKFQVLKTGQSMTLQCAQDMNHEYMSWYRQ
DPGMGLRLIHYSVGAG<u>T</u>TD<u>R</u>GEVPNGYNVSRSTI<u></u>EDFPL
RLLSAAPSQTSVYFCASSYVG<u>D</u>TGELFFGEGSRLTVL
(SEQ ID No: 97)

MGVTQTPKFQVLKTGQSMTLQCAQDMNHEYMSWYRQ
DPGMGLRLIHYSVGAG<u>TT</u>D<u>R</u>GEVPNGYNVSRSTI<u></u>EDFPL
RLLSAAPSQTSVYFCASSY<u>L</u>G<u>D</u>TGELFFGEGSRLTVL
(SEQ ID No: 98)

MGVTQTPKFQVLKTGQSMTLQCAQDMNHEYMSWYRQ
DPGMGLRLIHYSVGAG<u>TT</u>D<u>R</u>GEVPNGYNVSRSTI<u></u>EDFPL
RLLSAAPSQTSVYFCASS<u>F</u>VG<u>D</u>TGELFFGEGSRLTVL
(SEQ ID No: 99)

Figure 8a

N I Q N P D P A V Y Q L R D S K S S D K S V C L F T
D F D S Q T N V S Q S K D S D V Y I T D K (SEQ ID NO: 100)

Figure 8b

E D L N K V F P P E V A V F E P S E A E I S H T Q K A T
L V C L A T G F F P D H V E L S W W V N G K E V H S G V (SEQ ID NO: 101)

Figure 8c

E D L K N V F P P E V A V F E P S E A E I S H T Q K A T
L V C L A T G F Y P D H V E L S W W V N G K E V H S G V (SEQ ID NO: 102)

Figure 9

PEX954 gatctcgatcccgcgaaattaatacgactcactatagggagaccacaacggtttccctctagaaataattttgtttaactttaaga
aggagatataatcgatgtctaactcgagtgacaagtctgtctgcctattcaccgattttgattctcaaacaaatgtgtcacaaagt
aaggattctgatgtgtatatcacagacaaatgtgtgctagacatgaggtctatggacttcaagagcaacagtgctgtggcctg
gagcaacaaatctgactttgcatgtgcaaacgccttcaacaacagcattattccagaagacaccttcttccccagcccagaaa
gttcctaagcttgaattccgatccggctgctaacaaagcccgaaaggaagctgagttggctgctgccaccgctgagcaataa
ctagcataaccccttggggcctctaaacgggtcttgaggggttttttgctgaaaggaggaactatatccggataattcttgaag
acgaaagggcctcgtgatacgcctatttttataggttaatgtcatgataataatggtttcttagacgtgaggtggcacttttcggg
gaaatgtgcgcggaacccctatttgtttatttttctaaatacattcaaatatgtatccgctcatgagacaataaccctgataaatgc
ttcaataatattttgttaaaattcgcgttaaattttgttaaatcagctcattttttaaccaataggccgaaatcggcaaaatcccttat
aaatcaaaagaatagaccgagatagggttgagtgttgttccagtttggaacaagagtccactattaaagaacgtggactccaa
cgtcaaagggcgaaaaaccgtctatcagggcgatggcccactacgtgaaccatcaccctaatcaagtttttggggtcgagg
tgccgtaaagcactaaatcggaaccctaaagggagccccgatttagagcttgacggggaaagccggcgaacgtggcga
gaaaggaagggaagaaagcgaaaggagcgggcgctagggcgctggcaagtgtagcggtcacgctgcgcgtaaccacc
acacccgccgcgcttaatgcgccgctacagggcgcgtcaggtggcacttttcggggaaatgtgcgcggaacccctatttgtt
tattttctaaatacattcaaatatgtatccgctcatgagacaataaccctgataaatgcttcaataatattgaaaaaggaagagta
tgagtattcaacatttccgtgtcgcccttattcccttttttgcggcattttgccttcctgttttgctcacccagaaacgctggtgaaa
gtaaaagatgctgaagatcagttgggtgcacgagtgggttacatcgaactggatctcaacagcggtaagatccttgagagttt
tcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatg
gcatgacagtaagagaattatgcagtgctgccataaccatgagtgataacactgcggccaacttacttctgacaacgatcgg
aggaccgaaggagctaaccgcttttttgcacaacatgggggatcatgtaactcgccttgatcgttgggaaccggagctgaat
gaagccataccaaacgacgagcgtgacaccacgatgcctgcagcaatggcaacaacgttgcgcaaactattaactggcga
actacttactctagcttcccggcaacaattaatagactggatggaggcggataaagttgcaggaccacttctgcgctcggcc
ttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgag
ataggtgcctcactgattaagcattggtaactgtcagaccaagtttactcatatatactttagattgatttaaaacttcatttttaatt
aaaaggatctaggtgaagatcctttttgataatctcatgaccaaaatcccttaacgtgagttttcgttccactgagcgtcagacc

Figure 9 (continued)

ccgtagaaaagatcaaaggatcttcttgagatccttttttttctgcgcgtaatctgctgcttgcaaacaaaaaaaccaccgctacc
agcggtggtttgtttgccggatcaagagctaccaactctttttccgaaggtaactggcttcagcagagcgcagataccaaata
ctgtccttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcagcg
gtcgggctgaacggggggttcgtgcacacagcccagcttggagcgaacgacctacaccgaactgagatacctacagcgt
gagctatgagaaagcgccacgcttcccgaagggagaaaggcggacaggtatccggtaagcggcagggtcggaacagg
agagcgcacgagggagcttccaggggggaaacgcctggtatctttatagtcctgtcgggtttcgccacctctgacttgagcgt
cgattttgtgatgctcgtcaggggggcggagcctatggaaaaacgccagcaacgcggccttttacggttcctggccttttg
ctggccttttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctcctta
cgcatctgtgcggtatttcacaccgcaatggtgcactctcagtacaatctgctctgatgccgcatagttaagccagtatacact
ccgctatcgctacgtgactgggtcatggctgcgccccgacaccccgccaacacccgctgacgcgccctgacgggcttgtct
gctcccggcatccgcttacagacaagctgtgaccgtctccgggagctgcatgtgtcagaggttttcaccgtcatcaccgaaa
cgcgcgaggcag (SEQ ID NO: 113)

Figure 10

PEX821
gatctcgatcccgcgaaattaatacgactcactatagggagaccacaacggtttcccctctagaaataattttgtttaactttaaga
aggagatatacatatgaacgctggtgtcactcagaccccaaaattccaggtcctgaagacaggacagagcatgacactgca
gtgtgcccaggatatgaaccatgaatacatgtcctggtatcgacaagacccaggcatggggctgaggctgattcattactca
gttggtgctggtatcactgaccaaggagaagtccccaatggctacaatgtctccagatcaaccacagaggatttcccgctca
ggctgctgtcggctgctccctcccagacatctgtgtactictgtgccagcaggccgggactagcgggagggcgaccagag
cagtacttcgggccgggcaccaggctcacggtcacagaggacctgaaaaacgtgttccccaccgaggtcgctgtgtttga
gccatcagaagcagagatctcccacacccaaaaggccacactggtgtgcctggccaccggtttctaccccgaccacgtgg
agctgagctggtgggtgaatgggaaggaggtgcacagtggggtctgcacagacccgcagcccctcaaggagcagcccg
ccctcaatgactccagatacgctctgagcagccgcctgagggtctcggccaccttctggcaggaccccgcaaccacttcc
gctgtcaagtccagttctacgggctctcggagaatgacgagtggacccaggataggccaaacccgtcacccagatcgtc
agcgccgaggcctgggtagagcagactaagcttgaattccgatccggctgctaacaaagcccgaaaggaagctgagttg
gctgctgccaccgctgagcaataactagcataaccccttggggcctctaaacgggtcttgaggggttttttgctgaaaggag
gaactatatccggataattcttgaagacgaaagggcctcgtgatacgcctatttttataggttaatgtcatgataataatggtttct
tagacgtcaggtggcactttcggggaaatgtgcgcggaaccccctatttgtttatttttctaaatacattcaaatatgtatccgctc
atgagacaataaccctgataaatgcttcaataatattttgttaaaattcgcgttaaattttgttaaatcagctcattttttaaccaata
ggccgaaatcggcaaaatcccttataaatcaaaagaatagaccgagatagggttgagtgttgttccagtttggaacaagagt
ccactattaaagaacgtggactccaacgtcaaaggcgaaaaaccgtctatcagggcgatggcccactacgtgaaccatca
ccctaatcaagttttttggggtcgaggtgccgtaaagcactaaatcggaaccctaaagggagcccccgatttagagcttgac
ggggaaagccggcgaacgtggcgagaaaggaagggaagaaagcgaaaggagcgggcgctagggcgctggcaagtg
tagcggtcacgctgcgcgtaaccaccacacccgccgcgcttaatgcgccgctacagggcgcgtcaggtggcactttcgg
ggaaatgtgcgcggaacccctatttgtttatttttctaaatacattcaaatatgtatccgctcatgagacaataaccctgataaatg
cttcaataatattgaaaaaggaagagtatgagtattcaacatttccgtgtcgcccttattccctttttttgcggcattttgccttcctgt
ttttgctcacccagaaacgctggtgaaagtaaaagatgctgaagatcagttgggtgcacgagtgggttacatcgaactggat
ctcaacagcggtaagatccttgagagttttcgccccgaagaacgttttccaatgatgagcactttaaagttctgctatgtggcg
cggtattatcccgtgttgacgccgggcaagagcaactcggtcgccgcatacactattctcagaatgacttggttgagtactca
ccagtcacagaaaagcatcttacggatggcatgacagtaagagaattatgcagtgctgccataaccatgagtgataacactg
cggccaacttacttctgacaacgatcggaggaccgaaggagctaaccgcttttttgcacaacatgggggatcatgtaactcg
ccttgatcgttgggaaccggagctgaatgaagccataccaaacgacgagcgtgacaccacgatgcctgcagcaatggcaa
caacgttgcgcaaactattaactggcgaactacttactctagcttcccggcaacaattaatagactggatggaggcggataaa
gttgcaggaccacttctgcgctcggcccttccggctggctggtttattgctgataaatctggagccggtgagcgtgggtctcg
cggtatcattgcagcactggggccagatggtaagccctcccgtatcgtagttatctacacgacggggagtcaggcaactatg
gatgaacgaaatagacagatcgctgagataggtgcctcactgattaagcattggtaactgtcagaccaagtttactcatatata
ctttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactg
gcttcagcagagcgcagataccaaatactgtccttctagtgtagccgtagttaggccaccacttcaagaactctgtagcaccg
cctacatacctcgctctgctaatcctgttaccagtggctgctgccagtggcgataagtcgtgtcttaccgggttggactcaaga
cgatagttaccggataaggcgcagcggtcgggctgaacggggggttcgtgcacacagcccagcttggagcgaacgacct
acaccgaactgagatacctacagcgtgagctatgagaaagcgccacgcttcccgaagggagaaaggcggacaggtatcc
ggtaagcggcagggtcggaacaggagagcgcacgagggagcttccaggggaaacgcctggtatctttatagtcctgtc
gggtttcgccacctctgacttgagcgtcgatttttgtgatgctcgtcaggggggcggagcctatggaaaaacgccagcaacg Figure 10 (continued)

cggcctttttacggttcctggcctttgctggcctttgctcacatgttctttcctgcgttatcccctgattctgtggataaccgtatta
ccgcctttgagtgagctgataccgctcgccgcagccgaacgaccgagcgcagcgagtcagtgagcgaggaagcggaag
agcgcctgatgcggtattttctccttacgcatctgtgcggtatttcacaccgcaatggtgcactctcagtacaatctgctctgatg
ccgcatagttaagccagtatacactccgctatcgctacgtgactgggtcatggctgcgccccgacaccgccaacacccgc
tgacgcgccctgacgggcttgtctgctcccggcatccgcttacagacaagctgtgaccgtctccgggagctgcatgtgtcag
aggttttcaccgtcatcaccgaaacgcgcgaggcag
(SEQ ID NO: 114)

Figure 11 pEX202 gatctcgatcccgcgaaattaatacgactcactatagggagaccacaacggtttccctctagaaataattttgtttaactttaaga
aggagatatacatatgcagaaggaagtggagcagaactctggaccccctcagtgttccagagggagccattgcctctctcaa
ctgcacttacagtgaccgaggtcccagtccttcttctggtacagacaatattctgggaaaagccctgagttgataatgtccata
tactccaatggtgacaaagaagatggaaggtttacagcacagctcaataaagccagccagtatgtttctctgctcatcagaga
ctcccagcccagtgattcagccacctacctctgtgccgttacaactgacagctgggggaaattgcagtttggagcagggacc
caggttgtggtcaccccagatatccagaaccctgaccctgccgtgtaccagctgagagactctaaatccagtgacaagtctg
tctgcctattcaccgattttgattctcaaacaaatgtgtcacaaagtaaggattctgatgtgtatatcacagacaaaactgtgcta
gacatgaggtctatggacttcaagagcaacagtgctgtggcctggagcaacaaatctgactttgcatgtgcaaacgccttca
acaacagcattattccagaagacaccttcttccccagcccagaaagttccccggggggtagaatcgcccggctggaggaa
aaagtgaaaaccttgaaagctcagaactcggagctggcgtccacggccaacatgctcagggaacaggtggcacagcttaa
acagaaagtcatgaactactaggatccatggtaagcttgaattccgatccggctgctaacaaagcccgaaaggaagctgag
ttggctgctgccaccgctgagcaataactagcataaccccttggggcctctaaacgggtcttgaggggttttttgctgaaagg
aggaactatatccggataatcttgaagacgaaagggcctcgtgatacgcctatttttataggttaatgtcatgataataatggtt
tcttagacgtcaggtggcactttttcggggaaatgtgcgcggaacccctatttgtttatttttctaaatacattcaaatatgtatccg
ctcatgagacaataaccctgataaatgcttcaataatattttgttaaaattcgcgttaaattttgttaaatcagctcatttttaacca
ataggccgaaatcggcaaaatcccttataaatcaaaagaatagaccgagatagggttgagtgttgttccagtttggaacaaga
gtccactattaaagaacgtggactccaacgtcaaaggggcgaaaaaccgtctatcagggcgatggcccactacgtgaaccat
cacccctaatcaagttttttggggtcgaggtgccgtaaagcactaaatcggaacccctaaagggagcccccgatttagagcttg
acggggaaagccggcgaacgtggcgagaaaggaagggaagaaagcgaaaggagcgggcgctagggcgctggcaag
tgtagcggtcacgctgcgcgtaaccaccacaccgccgcgcttaatgcgccgctacagggcgcgtcaggtggcactttcg
gggaaatgtgcgcggaacccctatttgtttatttttctaaatacattcaaatatgtatccgctcatgagacaataaccctgataaat
gcttcaataatattgaaaaaggaagagtatgagtattcaacatttccgtgtcgcccttattcccttttttgcggcattttgccttcct
gtttttgctcacccagaaacgctggtgaaagtaaaagatgctgaagatcagttgggtgcacgagtgggttacatcgaactgg
atctcaacagcggtaagatccttgagagttttcgccccgaagaacgttttccaatgatgagcacttttaaagttctgctatgtgg
cgcggtattatcccgtgttgacgccgggcaagagcaactcggtcgccgcatacactattctcagaatgacttggttgagtact
caccagtcacagaaaagcatcttacggatggcatgacagtaagagaattatgcagtgctgccataaccatgagtgataacac
tgcggccaacttacttctgacaacgatcggaggaccgaaggagctaaccgcttttttgcacaacatgggggatcatgtaact
cgccttgatcgttgggaaccggagctgaatgaagccataccaaacgacgagcgtgacaccacgatgcctgcagcaatggc
aacaacgttgcgcaaactattaactggcgaactacttactctagcttcccggcaacaattaatagactggatggaggcggata
aagttgcaggaccacttctgcgctcggcccttccggctggctggtttattgctgataaatctggagccggtgagcgtgggtct
cgcggtatcattgcagcactggggccagatggtaagccctcccgtatcgtagttatctacacgacggggagtcaggcaact
atggatgaacgaaatagacagatcgctgagataggtgcctcactgattaagcattggtaactgtcagaccaagtttactcatat
atactttagattgatttaaaacttcatttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctg
ctgcttgcaaacaaaaaaaccaccgctaccagcggtggtttgtttgccggatcaagagctaccaactctttttccgaaggtaa
ctggcttcagcagagcgcagataccaaatactgtccttctagtgtagccgtagttaggccaccacttcaagaactctgtagca
ccgcctacatacctcgctctgctaatcctgttaccagtggctgctgccagtggcgataagtcgtgtcttaccgggttggactca
agacgatagttaccggataaggcgcagcggtcgggctgaacggggggttcgtgcacacagcccagcttggagcgaacg
acctacaccgaactgagatacctacagcgtgagctatgagaaagcgccacgcttcccgaagggagaaaggcggacaggt
atccggtaagcggcagggtcggaacaggagagcgcacgagggagcttccagggggaaacgcctggtatctttatagtcct
gtcgggtttcgccacctctgacttgagcgtcgatttttgtgatgctcgtcaggggggcggagcctatggaaaaacgccagca
acgcggccttttacggttcctggccttttgctggccttttgctcacatgttctttcctgcgttatcccctgattctgtggataaccgt Figure 11 (continued)

attaccgcctttgagtgagctgataccgctcgccgcagccgaacgaccgagcgcagcgagtcagtgagcgaggaagcgg
aagagcgcctgatgcggtattttctccttacgcatctgtgcggtatttcacaccgcaatggtgcactctcagtacaatctgctct
gatgccgcatagttaagccagtatacactccgctatcgctacgtgactgggtcatggctgcgccccgacacccgccaacac
ccgctgacgcgccctgacgggcttgtctgctcccggcatccgcttacagacaagctgtgaccgtctccgggagctgcatgt
gtcagaggttttcaccgtcatcaccgaaacgcgcgaggcag (SEQ ID NO: 115)

Figure 12 pEX205 gatctcgatcccgcgaaattaatacgactcactatagggagaccacaacggtttccctctagaaataattttgtttaactttaagaaggagat
atacatatgaacgctggtgtcactcagacccaaaattccaggtcctgaagacaggacagagcatgacactgcagtgtgcccaggatat
gaaccatgaatacatgtcctggtatcgacaagacccaggcatggggctgaggctgattcattactcagttggtgctggtatcactgacca
aggagaagtcccaatggctacaatgtctccagatcaaccacagaggatttcccgctcaggctgctgtcggctgctccctcccagacat
ctgtgtacttctgtgccagcaggccgggactagcgggagggcgaccagagcagtacttcgggccgggcaccaggctcacggtcaca
gaggacctgaaaaacgtgttcccacccgaggtcgctgtgtttgagccatcagaagcagagatctcccacacccaaaaggccacactgg
tgtgcctggccacaggcttctaccccgaccacgtggagctgagctggtgggtgaatgggaaggaggtgcacagtggggtcagcaca
gacccgcagcccctcaaggagcagcccgccctcaatgactccagatacgctctgagcagccgcctgagggtctcggccaccttctgg
caggacccccgcaaccacttccgctgtcaagtccagttctacggctctcggagaatgacgagtggacccaggatagggccaaaccc
gtcacccagatcgtcagcgccgaggcctggggtagagcagacccgggggtctgactgatacactccaagcggagacagatcaactt
gaagacaagaagtctgcgttgcagaccgagattgccaatctactgaaagagaaggaaaaactagagttcatcctggcagcttacggatc
cggtggtggtctgaacgatattttgaagctcagaaaatcgaatggcattaagcttgaattccgatccggctgctaacaaagcccgaaag
gaagctgagttggctgctgccaccgctgagcaataactagcataaccccttggggcctctaaacgggtcttgagggtttttgctgaaa
ggaggaactatatccggataattcttgaagacgaaagggcctcgtgatacgcctatttttataggttaatgtcatgataataatggtttcttag
acgtcaggtggcacttttcggggaaatgtgcgcggaacccctatttgtttatttttctaaatacattcaaatatgtatccgctcatgagacaat
aaccctgataaatgcttcaataatattttgttaaaattcgcgttaaattttttgttaaatcagctcattttttaaccaataggccgaaatcggcaaa
atcccttataaatcaaaagaatagaccgagatagggttgagtgttgttccagtttggaacaagagtccactattaaagaacgtggactcca
acgtcaaagggcgaaaaaccgtctatcagggcgatggcccactacgtgaaccatcaccctaatcaagttttttggggtcgaggtgccgt
aaagcactaaatcggaaccctaaagggagccccgatttagagcttgacggggaaagccggcgaacgtggcgagaaaggaaggga
agaaagcgaaaggagcgggcgctagggcgctggcaagtgtagcggtcacgctgcgcgtaaccaccacacccgccgcgcttaatgc
gccgctacagggcgcgtcaggtggcacttttcggggaaatgtgcgcggaacccctatttgtttatttttctaaatacattcaaatatgtatcc
gctcatgagacaataaccctgataaatgcttcaataatattgaaaaggaagagtatgagtattcaacatttccgtgtcgcccttattccttt
tttgcggcatttgccttcctgtttttgctcacccagaaacgctggtgaaagtaaaagatgctgaagatcagttgggtgcacgagtgggtta
catcgaactggatctcaacagcggtaagatccttgagagttttcgccccgaagaacgttttccaatgatgagcactttaaagttctgctatg
tggcgcggtattatcccgtgttgacgccgggcaagagcaactcggtcgccgcatacactattctcagaatgacttggttgagtactcacc
agtcacagaaaagcatcttacggatggcatgacagtaagagaattatgcagtgctgccataaccatgagtgataacactgcggccaactt
acttctgacaacgatcggaggaccgaaggagctaaccgcttttttgcacaacatgggggatcatgtaactcgccttgatcgttgggaacc
ggagctgaatgaagccataccaaacgacgagcgtgacaccacgatgcctgcagcaatggcaacaacgttgcgcaaactattaactgg
cgaactacttactctagcttcccggcaacaattaatagactggatggaggcggataaagttgcaggaccacttctgcgctcggcccttcc
ggctggctggtttattgctgataaatctggagccggtgagcgtgggtctcgcggtatcattgcagcactggggccagatggtaagccctc
ccgtatcgtagttatctacacgacggggagtcaggcaactatggatgaacgaaatagacagatcgctgagataggtgcctcactgattaa
gcattggtaactgtcagaccaagtttactcatatatactttagattgatttaaaacttcattttttaatttaaaaggatctaggtgaagatcctttttg
ataatctcatgaccaaaatcccttaacgtgagttttcgttccactgagcgtcagaccccgtagaaaagatcaaaggatcttcttgagatcctt
tttttctgcgcgtaatctgctgcttgcaaacaaaaaaaccaccgctaccagcggtggtttgtttgccggatcaagagctaccaactctttttc
cgaaggtaactggcttcagcagagcgcagataccaaatactgtccttctagtgtagccgtagttaggccaccacttcaagaactctgtag
caccgcctacatacctcgctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcgaacgacctacaccgaac
tgagatacctacagcgtgagctatgagaaagcgccacgcttcccgaagggagaaaggcggacaggtatccggtaagcggcagggtc
ggaacaggagagcgcacgagggagcttccagggggaaacgcctggtatctttatagtcctgtcgggtttcgccacctctgacttgagc
gtcgatttttgtgatgctcgtcaggggggcggagcctatggaaaaacgccagcaacgcggcctttttacggttcctggccttttgctggcc
ttttgctcacatgttctttcctgcgttatcccctgattctgtggataaccgtattaccgcctttgagtgagctgataccgctcgccgcagccga
acgaccgagcgcagcgagtcagtgagcgaggaagcggaagagcgcctgatgcggtattttctccttacgcatctgtgcggtatttcaca
ccgcaatggtgcactctcagtacaatctgctctgatgccgcatagttaagccagtatacactccgctatcgctacgtgactgggtcatggc
tgcgccccgacacccgccaacacccgctgacgcgccctgacgggcttgtctgctcccggcatccgcttacagacaagctgtgaccgtc
tccgggagctgcatgtgtcagaggttttcaccgtcatcaccgaaacgcgcgaggcag (SEQ ID NO: 116)

Figure 13

MGVTQTPKFQVLKTGQSMTLQCAQDMNHEYMSWYRQ
DPGMGLRLIHYSVAIQTTDQGEVPNGYNVSRSTIEDFPL
RLLSAAPSQTSVYFCASSYVGDTGELFFGEGSRLTVL
(SEQ ID No: 117)

MGVTQTPKFQVLKTGQSMTLQCAQDMNHEYMSWYRQ
DPGMGLRLIHYSVAIQTTDRGEVPNGYNVSRSTIEDFPL
RLLSAAPSQTSVYFCASSYLGNTGELFFGEGSRLTVL
(SEQ ID No: 118)

MGVTQTPKFQVLKTGQSMTLQCAQDMNHEYMSWYRQ
DPGMGLRLIHYSVAIQTTDQGEVPNGYNVSRSTIEDFPL
RLLSAAPSQTSVYFCASSYVGNTGELFFGEGSRLTVL
(SEQ ID No: 119)

MGVTQTPKFQVLKTGQSMTLQCAQDMNHEYMSWYRQ
DPGMGLRLIHYSVSVGMTDRGEVPNGYNVSRSTTEDFP
LRLLSAAPSQTSVYFCASSYVGDTGELFFGEGSRLTVL
(SEQ ID No: 120)

MGVTQTPKFQVLKTGQSMTLQCAQDMNHEYMSWYRQ
DPGMGLRLIHYSVAIQTTDRGEVPNGYNVSRSTIEDFPL
RLLSAAPSQTSVYFCASSYVGNTGELFFGEGSRLTVL
(SEQ ID No: 121)

Figure 14a

C58c61 alpha with TRAC

MKQEVTQIPAALSVPEGENLVLNCSFTDSAIYNLQWFR
QDPGKGLTSLLLI<u>TPW</u>QREQTSGRLNASLDKSSGRSTLY
IAASQPGDSATYLCAVRP<u>LLD</u>G<u>T</u>YIPTFGRGTSLIVHPYI
QNPDPAVYQLRDSKSSDKSVCLFTDFDSQTNVSQSKDS
DVYITDK (SEQ ID NO: 122)

Figure 14b

C58c61 beta with TRBC1

MNAGVTQTPKFQVLKTGQSMTLQCAQDMNHEYMSWY
RQDPGMGLRLIHYSV<u>AIQT</u>TDQGEVPNGYNVSRST<u>I</u>EDF
PLRLLSAAPSQTSVYFCASSY<u>L</u>GNTGELFFGEGSRLTVL
EDLNKVFPPEVAVFEPSEAEISHTQKATLVCLATGFFPD
HVELSWWVNGKEVHSGV (SEQ ID NO: 123)

Figure 14c

C58c61 beta with TRBC2

MNAGVTQTPKFQVLKTGQSMTLQCAQDMNHEYMSWY
RQDPGMGLRLIHYSV<u>AIQT</u>TDQGEVPNGYNVSRST<u>I</u>EDF
PLRL<u>L</u>SAAPSQTSVYFCASSY<u>L</u>GNTGELFFGEGSRLTVL
EDLKNVFPPEVAVFEPSEAEISHTQKATLVCLATGFYPD
HVELSWWVNGKEVHSGV (SEQ ID NO: 124)

Figure 14d

C58c61 beta with TRBC2 fused to wt human IL-2

MNAGVTQTPKFQVLKTGQSMTLQCAQDMNHEYMSWY
RQDPGMGLRLIHYSV<u>AIQT</u>TDQGEVPNGYNVSRST<u>I</u>EDF
PLRLLSAAPSQTSVYFCASSY<u>L</u>GNTGELFFGEGSRLTVL
EDLKNVFPPEVAVFEPSEAEISHTQKATLVCLATGFYPD
HVELSWWVNGKEVHSGV*PGAPTSSSTKKTQLQLEHLLL*
*DLQMILNGINNYKNPKLTRMLTFKFYMPKKATELKHLQCL*
*EEELKPLEEVLNLAQSKNFHLRPRDLISNINVIVLELKGSE*
*TTFMCEYADETATIVEFLNRWITFCQSIISTLT*

(SEQ ID NO: 125)

SEQUENCE LISTING

```
<160> NUMBER OF SEQ ID NOS: 127

<210> SEQ ID NO 1
<211> LENGTH: 115
<212> TYPE: PRT
<213> ORGANISM: Homo sapiens

<400> SEQUENCE: 1

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
```

```
                        20                  25                  30
Leu Gln Trp Phe Arg Gln Asp Pro Gly Lys Gly Leu Thr Ser Leu Leu
                35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 2
<211> LENGTH: 112
<212> TYPE: PRT
<213> ORGANISM: Homo sapiens

<400> SEQUENCE: 2

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
                35                  40                  45

Val Gly Ala Gly Ile Thr Asp Gln Gly Glu Val Pro Asn Gly Tyr Asn
            50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
                100                 105                 110

<210> SEQ ID NO 3
<211> LENGTH: 627
<212> TYPE: DNA
<213> ORGANISM: Artificial Sequence
<220> FEATURE:
<223> OTHER INFORMATION: DNA encoding Soluble version of 1G4 TCR alpha
      chain

<400> SEQUENCE: 3
atgcaggagg tgacacagat tcctgcagct ctgagtgtcc cagaaggaga aaacttggtt      60
ctcaactgca gtttcactga tagcgctatt tacaacctcc agtggtttag gcaggaccct    120
gggaaaggtc tcacatctct gttgcttatt cagtcaagtc agagagagca acaagtgga     180 agacttaatg cctcgctgga taatcatca  ggacgtagta ctttatacat tgcagcttct    240
cagcctggtg actcagccac ctacctctgt gctgtgaggc ccacatcagg aggaagctac    300
atacctacat ttggaagagg aaccagcctt attgttcatc cgtatatcca gaaccctgac    360
cctgccgtgt accagctgag agactctaaa tccagtgaca agtctgtctg cctattcacc    420
gattttgatt ctcaaacaaa tgtgtcacaa gtaaggatt  ctgatgtgta tatcacagac    480
aaaactgtgc tagacatgag gtctatggac ttcaagagca cagtgctgt  ggcctggagc    540 aacaaatctg actttgcatg tgcaaacgcc ttcaacaaca gcattattcc agaagacacc    600
```
ttcttcccca gcccagaaag ttcctaa 627

<210> SEQ ID NO 4
<211> LENGTH: 729
<212> TYPE: DNA
<213> ORGANISM: Artificial Sequence
<220> FEATURE:
<223> OTHER INFORMATION: DNA encoding Soluble version of 1G4 TCR beta
      chain

<400> SEQUENCE: 4

```
atgggtgtca ctcagacccc aaaattccag gtcctgaaga caggacagag catgacactg    60
cagtgtgccc aggatatgaa ccatgaatac atgtcctggt atcgacaaga cccaggcatg   120
gggctgaggc tgattcatta ctcagttggt gctggtatca ctgaccaagg agaagtcccc   180
aatggctaca atgtctccag atcaaccaca gaggatttcc cgctcaggct gctgtcggct   240
gctccctccc agacatctgt gtacttctgt gccagcagtt acgtcgggaa caccggggag   300
ctgttttttg gagaaggctc taggctgacc gtactggagg acctgaaaaa cgtgttccca   360
cccgaggtcg ctgtgtttga gccatcagaa gcagagatct cccacaccca aaaggccaca   420
ctggtgtgcc tggccacagg cttctacccc gaccacgtgg agctgagctg gtgggtgaat   480
gggaaggagg tgcacagtgg ggtcagcaca gacccgcagc ccctcaagga gcagcccgcc   540
ctcaatgact ccagatacgc tctgagcagc cgcctgaggg tctcggccac cttctggcag   600
gacccccgca accacttccg ctgtcaagtc cagttctacg ggctctcgga gaatgacgag   660
tggacccagg atagggccaa acccgtcacc cagatcgtca gcgccgaggc ctggggtaga   720
gcagactaa                                                          729
```

<210> SEQ ID NO 5
<211> LENGTH: 208
<212> TYPE: PRT
<213> ORGANISM: Artificial Sequence
<220> FEATURE:
<223> OTHER INFORMATION: Soluble version of 1G4 TCR alpha chain

<400> SEQUENCE: 5

```
Met Gln Glu Val Thr Gln Ile Pro Ala Ala Leu Ser Val Pro Glu Gly
1               5                   10                  15
Glu Asn Leu Val Leu Asn Cys Ser Phe Thr Asp Ser Ala Ile Tyr Asn
            20                  25                  30
Leu Gln Trp Phe Arg Gln Asp Pro Gly Lys Gly Leu Thr Ser Leu Leu
        35                  40                  45
Leu Ile Gln Ser Ser Gln Arg Glu Gln Thr Ser Gly Arg Leu Asn Ala
    50                  55                  60
Ser Leu Asp Lys Ser Ser Gly Arg Ser Thr Leu Tyr Ile Ala Ala Ser
65                  70                  75                  80
Gln Pro Gly Asp Ser Ala Thr Tyr Leu Cys Ala Val Arg Pro Thr Ser
                85                  90                  95
Gly Gly Ser Tyr Ile Pro Thr Phe Gly Arg Gly Thr Ser Leu Ile Val
            100                 105                 110
His Pro Tyr Ile Gln Asn Pro Asp Pro Ala Val Tyr Gln Leu Arg Asp
        115                 120                 125
Ser Lys Ser Ser Asp Lys Ser Val Cys Leu Phe Thr Asp Phe Asp Ser
    130                 135                 140
Gln Thr Asn Val Ser Gln Ser Lys Asp Ser Asp Val Tyr Ile Thr Asp
145                 150                 155                 160
```

```
Lys Thr Val Leu Asp Met Arg Ser Met Asp Phe Lys Ser Asn Ser Ala
            165                 170                 175
Val Ala Trp Ser Asn Lys Ser Asp Phe Ala Cys Ala Asn Ala Phe Asn
        180                 185                 190
Asn Ser Ile Ile Pro Glu Asp Thr Phe Phe Pro Ser Pro Glu Ser Ser
        195                 200                 205

<210> SEQ ID NO 6
<211> LENGTH: 242
<212> TYPE: PRT
<213> ORGANISM: Artificial Sequence
<220> FEATURE:
<223> OTHER INFORMATION: Soluble version of 1G4 TCR beta chain

<400> SEQUENCE: 6

Met Gly Val Thr Gln Thr Pro Lys Phe Gln Val Leu Lys Thr Gly Gln
1               5                   10                  15
Ser Met Thr Leu Gln Cys Ala Gln Asp Met Asn His Glu Tyr Met Ser
            20                  25                  30
Trp Tyr Arg Gln Asp Pro Gly Met Gly Leu Arg Leu Ile His Tyr Ser
        35                  40                  45
Val Gly Ala Gly Ile Thr Asp Gln Gly Glu Val Pro Asn Gly Tyr Asn
    50                  55                  60
Val Ser Arg Ser Thr Thr Glu Asp Phe Pro Leu Arg Leu Leu Ser Ala
65                  70                  75                  80
Ala Pro Ser Gln Thr Ser Val Tyr Phe Cys Ala Ser Ser Tyr Val Gly
            85                  90                  95
Asn Thr Gly Glu Leu Phe Phe Gly Glu Gly Ser Arg Leu Thr Val Leu
        100                 105                 110
Glu Asp Leu Lys Asn Val Phe Pro Pro Glu Val Ala Val Phe Glu Pro
        115                 120                 125
Ser Glu Ala Glu Ile Ser His Thr Gln Lys Ala Thr Leu Val Cys Leu
    130                 135                 140
Ala Thr Gly Phe Tyr Pro Asp His Val Glu Leu Ser Trp Trp Val Asn
145                 150                 155                 160
Gly Lys Glu Val His Ser Gly Val Ser Thr Asp Pro Gln Pro Leu Lys
            165                 170                 175
Glu Gln Pro Ala Leu Asn Asp Ser Arg Tyr Ala Leu Ser Ser Arg Leu
        180                 185                 190
Arg Val Ser Ala Thr Phe Trp Gln Asp Pro Arg Asn His Phe Arg Cys
        195                 200                 205
Gln Val Gln Phe Tyr Gly Leu Ser Glu Asn Asp Glu Trp Thr Gln Asp
    210                 215                 220
Arg Ala Lys Pro Val Thr Gln Ile Val Ser Ala Glu Ala Trp Gly Arg
225                 230                 235                 240
Ala Asp

<210> SEQ ID NO 7
<211> LENGTH: 627
<212> TYPE: DNA
<213> ORGANISM: Artificial Sequence
<220> FEATURE:
<223> OTHER INFORMATION: DNA encoding a soluble version of 1G4 TCR alpha
      chain containing a non native cysteine codon

<400> SEQUENCE: 7
atgcaggagg tgacacagat tcctgcagct ctgagtgtcc agaaggaga  aaacttggtt      60
```

```
ctcaactgca gtttcactga tagcgctatt tacaacctcc agtggtttag gcaggaccct    120
gggaaaggtc tcacatctct gttgcttatt cagtcaagtc agagagagca aacaagtgga    180
agacttaatg cctcgctgga taaatcatca ggacgtagta ctttatacat tgcagcttct    240
cagcctggtg actcagccac ctacctctgt gctgtgaggc ccacatcagg aggaagctac    300
atacctacat ttggaagagg aaccagcctt attgttcatc cgtatatcca gaaccctgac    360
cctgccgtgt accagctgag agactctaaa tccagtgaca gtctgtctg cctattcacc    420 gattttgatt ctcaaacaaa tgtgtcacaa gtaaggatt ctgatgtgta tatcacagac    480
aaatgtgtgc tagacatgag gtctatggac ttcaagagca cagtgctgt ggcctggagc    540 aacaaatctg actttgcatg tgcaaacgcc ttcaacaaca gcattattcc agaagacacc    600
ttcttcccca gcccagaaag ttcctaa                                       627

<210> SEQ ID NO 8
<211> LENGTH: 729
<212> TYPE: DNA
<213> ORGANISM: Artificial Sequence
<220> FEATURE:
<223> OTHER INFORMATION: DNA encoding a soluble version of the 1G4 TCR
      beta chain containing a non native cysteine codon

<400> SEQUENCE: 8
atgggtgtca ctcagacccc aaaattccag gtcctgaaga caggacagag catgacactg     60
cagtgtgccc aggatatgaa ccatgaatac atgtcctggt atcgacaaga cccaggcatg    120
gggctgaggc tgattcatta ctcagttggt gctggtatca ctgaccaagg agaagtcccc    180
aatggctaca atgtctccag atcaaccaca gaggatttcc cgctcaggct gctgtcggct    240
gctcccctcc agacatctgt gtacttctgt gccagcagtt acgtcgggaa caccggggag    300 ctgtttttg gagaaggctc taggctgacc gtactggagg acctgaaaaa cgtgttccca    360
cccgaggtcg ctgtgtttga gccatcagaa gcagagatct cccacaccca aaaggccaca    420
ctggtgtgcc tggccacagg cttctacccc gaccacgtgg agctgagctg gtgggtgaat    480
gggaaggagg tgcacagtgg ggtctgcaca gacccgcagc ccctcaagga gcagcccgcc    540
ctcaatgact ccagatacgc tctgagcagc cgcctgaggg tctcggccac cttctggcag    600
gacccccgca accacttccg ctgtcaagtc cagttctacg gctctcggga gaatgacgag    660
tggacccagg atagggccaa accgtcacc cagatcgtca gcgccgaggc ctggggtaga    720
gcagactaa                                                           729

<210> SEQ ID NO 9
<211> LENGTH: 208
<212> TYPE: PRT
<213> ORGANISM: Artificial Sequence
<220> FEATURE:
<223> OTHER INFORMATION: Soluble version of the 1G4 TCR alpha chain
      containing a non-native cysteine residue

<400> SEQUENCE: 9

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
```

```
                  50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
                100                 105                 110

His Pro Tyr Ile Gln Asn Pro Asp Pro Ala Val Tyr Gln Leu Arg Asp
                115                 120                 125

Ser Lys Ser Ser Asp Lys Ser Val Cys Leu Phe Thr Asp Phe Asp Ser
130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
                180                 185                 190

Asn Ser Ile Ile Pro Glu Asp Thr Phe Phe Pro Ser Pro Glu Ser Ser
                195                 200                 205

<210> SEQ ID NO 10
<211> LENGTH: 242
<212> TYPE: PRT
<213> ORGANISM: Artificial Sequence
<220> FEATURE:
<223> OTHER INFORMATION: Soluble version of the 1G4 TCR beta chain
      containing a non native cysteine residue

<400> SEQUENCE: 10

Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
                35                  40                  45

Val Gly Ala Gly Ile Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
                 85                  90                  95

Asn Thr Gly Glu Leu Phe Phe Gly Glu Gly Ser Arg Leu Thr Val Leu
                100                 105                 110

Glu Asp Leu Lys Asn Val Phe Pro Pro Glu Val Ala Val Phe Glu Pro
                115                 120                 125

Ser Glu Ala Glu Ile Ser His Thr Gln Lys Ala Thr Leu Val Cys Leu
130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
                180                 185                 190

Arg Val Ser Ala Thr Phe Trp Gln Asp Pro Arg Asn His Phe Arg Cys
                195                 200                 205
```

-continued

```
Gln Val Gln Phe Tyr Gly Leu Ser Glu Asn Asp Glu Trp Thr Gln Asp
    210                 215                 220
Arg Ala Lys Pro Val Thr Gln Ile Val Ser Ala Glu Ala Trp Gly Arg
225                 230                 235                 240
Ala Asp
```

<210> SEQ ID NO 11
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 11

```
Met Gln Glu Val Thr Gln Ile Pro Ala Ala Leu Ser Val Pro Glu Gly
1               5                   10                  15
Glu Asn Leu Val Leu Asn Cys Ser Phe Thr Asp Ser Ala Ile Tyr Asn
                20                  25                  30
Leu Gln Trp Phe Arg Gln Asp Pro Gly Lys Gly Leu Thr Ser Leu Leu
            35                  40                  45
Leu Ile Gln Ser Ser Gln Arg Glu Gln Thr Ser Gly Arg Leu Asn Ala
        50                  55                  60
Ser Leu Asp Lys Ser Ser Gly Arg Ser Thr Leu Tyr Ile Ala Ala Ser
65                  70                  75                  80
Gln Pro Gly Asp Ser Ala Thr Tyr Leu Cys Ala Val Arg Pro Leu Leu
                85                  90                  95
Asp Gly Thr Tyr Ile Pro Thr Phe Gly Arg Gly Thr Ser Leu Ile Val
                100                 105                 110
His Pro Tyr
        115
```

<210> SEQ ID NO 12
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 12

```
Met Gln Glu Val Thr Gln Ile Pro Ala Ala Leu Ser Val Pro Glu Gly
1               5                   10                  15
Glu Asn Leu Val Leu Asn Cys Ser Phe Thr Asp Ser Ala Ile Tyr Asn
                20                  25                  30
Leu Gln Trp Phe Arg Gln Asp Pro Gly Lys Gly Leu Thr Ser Leu Leu
            35                  40                  45
Leu Ile Gln Ser Ser Gln Arg Glu Gln Thr Ser Gly Arg Leu Asn Ala
        50                  55                  60
Ser Leu Asp Lys Ser Ser Gly Arg Ser Thr Leu Tyr Ile Ala Ala Ser
65                  70                  75                  80
Gln Pro Gly Asp Ser Ala Thr Tyr Leu Cys Ala Val Arg His Thr Ser
                85                  90                  95
Asn Gly Tyr Phe Pro Pro Thr Phe Gly Arg Gly Thr Ser Leu Ile Val
                100                 105                 110
His Pro Tyr
        115
```

<210> SEQ ID NO 13
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 13

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Thr
                85                  90                  95

Gly Gly Thr Tyr Ile Pro Thr Phe Gly Arg Gly Thr Ser Leu Ile Val
            100                 105                 110

His Pro Tyr
        115
```

<210> SEQ ID NO 14
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 14

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Tyr
                85                  90                  95

Gly Gly Thr Tyr Ile Pro Thr Phe Gly Arg Gly Thr Ser Leu Ile Val
            100                 105                 110

His Pro Tyr
        115
```

<210> SEQ ID NO 15
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 15

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Ile
                85                  90                  95

Gly Gly Thr Tyr Ile Pro Thr Phe Gly Arg Gly Thr Ser Leu Ile Val
                100                 105                 110

His Pro Tyr
        115

<210> SEQ ID NO 16
<211> LENGTH: 115
<212> TYPE: PRT
<213> ORGANISM: Artificial Sequence
<220> FEATURE:
<223> OTHER INFORMATION: high affinity 1G4 TCR variant

<400> SEQUENCE: 16

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Thr
                85                  90                  95

Gly Gly Thr Tyr Ile Pro Thr Phe Gly Arg Gly Thr Ser Leu Ile Val
                100                 105                 110

His Pro Tyr
        115

<210> SEQ ID NO 17
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 17

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45
```

Leu Ile Gln Ser Ser Gln Arg Glu Gln Thr Ser Gly Arg Leu Asn Ala
            50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Thr
                    85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 18
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 18

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
            50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ala Thr
                    85                  90                  95

Gly Gly Thr Tyr Ile Pro Thr Phe Gly Arg Gly Thr Ser Leu Ile Val
                100                 105                 110

His Pro Tyr
        115

<210> SEQ ID NO 19
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 19

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
            50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Gln Thr
                    85                  90                  95

-continued

Val Pro Thr Tyr Ile Pro Thr Phe Gly Arg Gly Thr Ser Leu Ile Val
            100                 105                 110

His Pro Tyr
        115

<210> SEQ ID NO 20
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 20

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Ser
                85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 21
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 21

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Tyr Gln
                85                  90                  95

Ser Gly His Tyr Met Pro Thr Phe Gly Arg Gly Thr Ser Leu Ile Val
            100                 105                 110

His Pro Tyr
        115

<210> SEQ ID NO 22
<211> LENGTH: 115

<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 22

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Asp Tyr Thr Pro Thr Phe Gly Arg Gly Thr Ser Leu Ile Val
                100                 105                 110

His Pro Tyr
        115

<210> SEQ ID NO 23
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 23

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Leu
                85                  90                  95

Gly Gly Thr Tyr Ile Pro Thr Phe Gly Arg Gly Thr Ser Leu Ile Val
                100                 105                 110

His Pro Tyr
        115

<210> SEQ ID NO 24
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 24

Met Gln Glu Val Thr Gln Ile Pro Ala Ala Leu Ser Val Pro Glu Gly

```
                 1               5                  10                 15
Glu Asn Leu Val Leu Asn Cys Ser Phe Thr Asp Ser Ala Ile Tyr Asn
                20                 25                 30

Leu Gln Trp Phe Arg Gln Asp Pro Gly Lys Gly Leu Thr Ser Leu Leu
            35                 40                 45

Leu Ile Gln Ser Ser Gln Arg Glu Gln Thr Ser Gly Arg Leu Asn Ala
        50                 55                 60

Ser Leu Asp Lys Ser Ser Gly Arg Ser Thr Leu Tyr Ile Ala Ala Ser
 65                 70                 75                 80

Gln Pro Gly Asp Ser Ala Thr Tyr Leu Cys Ala Val Arg Pro Leu Gln
                85                 90                 95

Asp Gly Thr Tyr Ile Pro Thr Phe Gly Arg Gly Thr Ser Leu Ile Val
                100                105                110

His Pro Tyr
        115

<210> SEQ ID NO 25
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 25

Met Gln Glu Val Thr Gln Ile Pro Ala Ala Leu Ser Val Pro Glu Gly
1               5                  10                 15

Glu Asn Leu Val Leu Asn Cys Ser Phe Thr Asp Ser Ala Ile Tyr Asn
                20                 25                 30

Leu Gln Trp Phe Arg Gln Asp Pro Gly Lys Gly Leu Thr Ser Leu Leu
            35                 40                 45

Leu Ile Gln Ser Ser Gln Arg Glu Gln Thr Ser Gly Arg Leu Asn Ala
        50                 55                 60

Ser Leu Asp Lys Ser Ser Gly Arg Ser Thr Leu Tyr Ile Ala Ala Ser
 65                 70                 75                 80

Gln Pro Gly Asp Ser Ala Thr Tyr Leu Cys Ala Val Arg Pro Met Thr
                85                 90                 95

Asp Ser Thr Tyr Ile Pro Thr Phe Gly Arg Gly Thr Ser Leu Ile Val
                100                105                110

His Pro Tyr
        115

<210> SEQ ID NO 26
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 26

Met Gln Glu Val Thr Gln Ile Pro Ala Ala Leu Ser Val Pro Glu Gly
1               5                  10                 15

Glu Asn Leu Val Leu Asn Cys Ser Phe Thr Asp Ser Ala Ile Tyr Asn
                20                 25                 30

Leu Gln Trp Phe Arg Gln Asp Pro Gly Lys Gly Leu Thr Ser Leu Leu
            35                 40                 45

Leu Ile Gln Ser Ser Gln Arg Glu Gln Thr Ser Gly Arg Leu Asn Ala
```

```
                50                  55                  60
Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Val
                 85                  90                  95

Asp Pro Thr Tyr Ile Pro Thr Phe Gly Arg Gly Thr Ser Leu Ile Val
                100                 105                 110

His Pro Tyr
        115

<210> SEQ ID NO 27
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 27

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
         50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Glu Val
                 85                  90                  95

Asp Ala Thr Tyr Ile Pro Thr Phe Gly Arg Gly Thr Ser Leu Ile Val
                100                 105                 110

His Pro Tyr
        115

<210> SEQ ID NO 28
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 28

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
         50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Glu
                 85                  90                  95

Asp Ser Thr Tyr Ile Pro Thr Phe Gly Arg Gly Thr Ser Leu Ile Val
```

His Pro Tyr
    115

<210> SEQ ID NO 29
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 29

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Val
                85                  90                  95

Gly Gly Val Tyr Ile Pro Thr Phe Gly Arg Gly Thr Ser Leu Ile Val
            100                 105                 110

His Pro Tyr
    115

<210> SEQ ID NO 30
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 30

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Asn Tyr Ile Pro Thr Phe Gly Arg Gly Thr Ser Leu Ile Val
            100                 105                 110

His Pro Tyr
    115

<210> SEQ ID NO 31
<211> LENGTH: 115
<212> TYPE: PRT

<213> ORGANISM: Artificial Sequence
<220> FEATURE:
<223> OTHER INFORMATION: High affinity variant of 1G4 TCR alpha chain variable domain AA sequence

<400> SEQUENCE: 31

```
Met Gln Glu Val Thr Gln Ile Pro Ala Ala Leu Ser Val Pro Glu Gly
 1               5                  10                  15
Glu Asn Leu Val Leu Asn Cys Ser Phe Thr Asp Ser Ala Ile Tyr Asn
                20                  25                  30
Leu Gln Trp Phe Arg Gln Asp Pro Gly Lys Gly Leu Thr Ser Leu Leu
            35                  40                  45
Leu Ile Gln Ser Ser Gln Arg Glu Gln Thr Ser Gly Arg Leu Asn Ala
        50                  55                  60
Ser Leu Asp Lys Ser Ser Gly Arg Ser Thr Leu Tyr Ile Ala Ala Ser
65                  70                  75                  80
Gln Pro Gly Asp Ser Ala Thr Tyr Leu Cys Ala Val Arg Pro Thr Thr
                85                  90                  95
Gly Gly Ser Tyr Ile Pro Thr Phe Gly Arg Gly Thr Ser Leu Ile Val
                100                 105                 110
His Pro Tyr
        115
```

<210> SEQ ID NO 32
<211> LENGTH: 115
<212> TYPE: PRT
<213> ORGANISM: Artificial Sequence
<220> FEATURE:
<223> OTHER INFORMATION: High affinity variant of 1G4 TCR alpha chain variable domain AA sequence

<400> SEQUENCE: 32

```
Met Gln Glu Val Thr Gln Ile Pro Ala Ala Leu Ser Val Pro Glu Gly
 1               5                  10                  15
Glu Asn Leu Val Leu Asn Cys Ser Phe Thr Asp Ser Ala Ile Tyr Asn
                20                  25                  30
Leu Gln Trp Phe Arg Gln Asp Pro Gly Lys Gly Leu Thr Ser Leu Leu
            35                  40                  45
Leu Ile Gln Ser Ser Gln Arg Glu Gln Thr Ser Gly Arg Leu Asn Ala
        50                  55                  60
Ser Leu Asp Lys Ser Ser Gly Arg Ser Thr Leu Tyr Ile Ala Ala Ser
65                  70                  75                  80
Gln Pro Gly Asp Ser Ala Thr Tyr Leu Cys Ala Val Arg Pro Ile Ser
                85                  90                  95
Gly Gly Ser Tyr Ile Pro Thr Phe Gly Arg Gly Thr Ser Leu Ile Val
                100                 105                 110
His Pro Tyr
        115
```

<210> SEQ ID NO 33
<211> LENGTH: 115
<212> TYPE: PRT
<213> ORGANISM: Artificial Sequence
<220> FEATURE:
<223> OTHER INFORMATION: High affinity variant of 1G4 TCR alpha chain variable domain AA sequence

<400> SEQUENCE: 33

```
Met Gln Glu Val Thr Gln Ile Pro Ala Ala Leu Ser Val Pro Glu Gly
 1               5                  10                  15
```

```
Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 34
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 34

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Thr
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 35
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 35

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60
```

```
Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ile Ser
                 85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 36
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 36

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 37
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 37

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ala
                 85                  90                  95

Gly Gly Ser Tyr Ile Pro Ala Phe Gly Arg Gly Thr Ser Leu Ile Val
            100                 105                 110
```

His Pro Tyr
    115

<210> SEQ ID NO 38
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 38

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Ser
                85                  90                  95

Gly Gly Ser Tyr Ile Pro Thr Phe Gly Arg Gly Thr Ser Leu Ile Val
            100                 105                 110

His Pro Tyr
    115

<210> SEQ ID NO 39
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 39

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Thr
                85                  90                  95

Gly Gly Ser Tyr Ile Pro Thr Phe Gly Arg Gly Thr Ser Leu Ile Val
            100                 105                 110

His Pro Tyr
    115

<210> SEQ ID NO 40
<211> LENGTH: 114
<212> TYPE: PRT
<213> ORGANISM: Artificial Sequence

```
<220> FEATURE:
<223> OTHER INFORMATION: High affinity variant of 1G4 TCR alpha chain
      variable domain AA sequence

<400> SEQUENCE: 40

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Gln
                85                  90                  95

Tyr Thr Gln Val Pro Thr Phe Gly Arg Gly Thr Ser Leu Ile Val His
            100                 105                 110

Pro Tyr

<210> SEQ ID NO 41
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 41

Met Gln Glu Val Thr Gln Ile Pro Ala Ala Leu Ser Val Pro Glu Gly
1               5                   10                  15

Glu Asn Leu Ala Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Pro Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 42
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 42

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
```

```
                    20                  25                  30

Leu Gln Trp Phe Arg Gln Asp Pro Gly Lys Gly Leu Thr Ser Leu Leu
            35                  40                  45

Leu Ile Pro Phe Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 43
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 43

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 44
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 44

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Thr Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
```

```
                65                  70                  75                  80
Gln Pro Gly Asp Ser Ala Thr Tyr Leu Cys Ala Val Arg Pro Thr Ser
                    85                  90                  95

Gly Gly Ser Tyr Ile Pro Thr Phe Gly Arg Gly Thr Ser Leu Ile Val
                    100                 105                 110

His Pro Tyr
        115

<210> SEQ ID NO 45
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 45

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                    85                  90                  95

Gly Gly Ser Tyr Ile Pro Thr Phe Gly Arg Gly Thr Ser Leu Ile Val
                    100                 105                 110

His Pro Tyr
        115

<210> SEQ ID NO 46
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 46

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Met Gly His Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                    85                  90                  95

Gly Gly Ser Tyr Ile Pro Thr Phe Gly Arg Gly Thr Ser Leu Ile Val
                    100                 105                 110

His Pro Tyr
```

<210> SEQ ID NO 47
<211> LENGTH: 115
<212> TYPE: PRT
<213> ORGANISM: Artificial Sequence
<220> FEATURE:
<223> OTHER INFORMATION: High affinity variant of 1G4 TCR alpha chain
     variable domain AA sequence

<400> SEQUENCE: 47

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Met Gly Thr Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 48
<211> LENGTH: 115
<212> TYPE: PRT
<213> ORGANISM: Artificial Sequence
<220> FEATURE:
<223> OTHER INFORMATION: High affinity variant of 1G4 TCR alpha chain
     variable domain AA sequence

<400> SEQUENCE: 48

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Pro Phe Trp Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr
        115

<210> SEQ ID NO 49
<211> LENGTH: 115
<212> TYPE: PRT
<213> ORGANISM: Artificial Sequence
<220> FEATURE:
<223> OTHER INFORMATION: High affinity variant of 1G4 TCR alpha chain -continued variable domain AA sequence

<400> SEQUENCE: 49

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr
        115

<210> SEQ ID NO 50
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 50

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr
        115

<210> SEQ ID NO 51
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 51

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
            35                  40                  45

Leu Ile Met Gly His Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 52
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 52

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
            35                  40                  45

Leu Ile Met Gly Thr Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 53
<211> LENGTH: 115
<212> TYPE: PRT
<213> ORGANISM: High affinity variant of 1G4 TCR alpha chain variable
      domain AA sequence
<400> SEQUENCE: 53

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
            35                  40                  45

Leu Ile Met Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr
        115

<210> SEQ ID NO 54
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 54

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Arg
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 55
<211> LENGTH: 116
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 55

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Asn Asp
                85                  90                  95

Gly Ser Gly Ser Tyr Ile Pro Thr Phe Gly Arg Gly Thr Ser Leu Ile
            100                 105                 110

Val His Pro Tyr
        115

<210> SEQ ID NO 56

```
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 56

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Trp
                85                  90                  95

Gly Gly Asn Tyr Ile Pro Thr Phe Gly Arg Gly Thr Ser Leu Ile Val
                100                 105                 110

His Pro Tyr
        115

<210> SEQ ID NO 57
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 57

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Glu
                85                  90                  95

Gly Gly Glu Tyr Ile Pro Thr Phe Gly Arg Gly Thr Ser Leu Ile Val
                100                 105                 110

His Pro Tyr
        115

<210> SEQ ID NO 58
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 58
```

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Phe Thr
                85                  90                  95

Gly Gly Gly Tyr Ile Pro Thr Phe Gly Arg Gly Thr Ser Leu Ile Val
            100                 105                 110

His Pro Tyr
        115

<210> SEQ ID NO 59
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 59

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Val Ser
                85                  90                  95

Gly Gly Asp Tyr Ile Pro Thr Phe Gly Arg Gly Thr Ser Leu Ile Val
            100                 105                 110

His Pro Tyr
        115

<210> SEQ ID NO 60
<211> LENGTH: 116
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 60

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

```
Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Asp
                85                  90                  95

Asp Gly Gly Arg Tyr Ile Pro Thr Phe Gly Arg Gly Thr Ser Leu Ile
                100                 105                 110

Val His Pro Tyr
        115

<210> SEQ ID NO 61
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 61

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Asn Thr
                85                  90                  95

Gly Gly Gln Tyr Ile Pro Thr Phe Gly Arg Gly Thr Ser Leu Ile Val
                100                 105                 110

His Pro Tyr
        115

<210> SEQ ID NO 62
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 62

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ile Ala
                85                  90                  95
```

```
Gly Gly Lys Tyr Ile Pro Thr Phe Gly Arg Gly Thr Ser Leu Ile Val
            100                 105                 110

His Pro Tyr
        115

<210> SEQ ID NO 63
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 63

Met Gln Glu Val Thr Gln Ile Pro Ala Ala Leu Ser Val Pro Glu Gly
1               5                  10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Gly Thr
                85                  90                  95

Gly Gly Asp Tyr Ile Pro Thr Phe Gly Arg Gly Thr Ser Leu Ile Val
            100                 105                 110

His Pro Tyr
        115

<210> SEQ ID NO 64
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 64

Met Gln Glu Val Thr Gln Ile Pro Ala Ala Leu Ser Val Pro Glu Gly
1               5                  10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Ala
                85                  90                  95

Gly Gly Ser Asp Ile Pro Thr Phe Gly Arg Gly Thr Ser Leu Ile Val
            100                 105                 110

His Pro Tyr
        115

<210> SEQ ID NO 65
<211> LENGTH: 115
```

-continued

```
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 65

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Ala
                85                  90                  95

Gly Gly Ala Tyr Ile Pro Thr Phe Gly Arg Gly Thr Ser Leu Ile Val
            100                 105                 110

His Pro Tyr
        115

<210> SEQ ID NO 66
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 66

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Arg
                85                  90                  95

Gly Gly Asp Tyr Ile Pro Thr Phe Gly Arg Gly Thr Ser Leu Ile Val
            100                 105                 110

His Pro Tyr
        115

<210> SEQ ID NO 67
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 67

Met Gln Glu Val Thr Gln Ile Pro Ala Ala Leu Ser Val Pro Glu Gly
```

```
                1               5                  10                 15
             Glu Asn Leu Val Leu Asn Cys Ser Phe Thr Asp Ser Ala Ile Tyr Asn
                              20                  25                 30

Leu Gln Trp Phe Arg Gln Asp Pro Gly Lys Gly Leu Thr Ser Leu Leu
                         35                  40                  45

Leu Ile Ser Pro Trp Gln Arg Glu Gln Thr Ser Gly Arg Leu Asn Ala
                     50                  55                  60

Ser Leu Asp Lys Ser Ser Gly Arg Ser Thr Leu Tyr Ile Ala Ala Ser
             65                  70                  75                  80

Gln Pro Gly Asp Ser Ala Thr Tyr Leu Cys Ala Val Arg Pro Leu Gly
                             85                  90                  95

Gly Gly Ile Tyr Ile Pro Thr Phe Gly Arg Gly Thr Ser Leu Ile Val
                             100                 105                 110

His Pro Tyr
                     115

<210> SEQ ID NO 68
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 68

Met Gln Glu Val Thr Gln Ile Pro Ala Ala Leu Ser Val Pro Glu Gly
1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Gly
                85                  90                  95

Gly Gly Arg Tyr Ile Pro Thr Phe Gly Arg Gly Thr Ser Leu Ile Val
                100                 105                 110

His Pro Tyr
        115

<210> SEQ ID NO 69
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 69

Met Gln Glu Val Thr Gln Ile Pro Ala Ala Leu Ser Val Pro Glu Gly
1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
```

```
                50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ser Val
                 85                  90                  95

Gly Gly Asn Tyr Ile Pro Thr Phe Gly Arg Gly Thr Ser Leu Ile Val
                100                 105                 110

His Pro Tyr
        115

<210> SEQ ID NO 70
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 70

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
             35                  40                  45

Leu Ile Gln Gly Trp Gln Arg Glu Gln Thr Ser Gly Arg Leu Asn Ala
         50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ala Thr
                 85                  90                  95

Gly Gly Asn Tyr Ile Pro Thr Phe Gly Arg Gly Thr Ser Leu Ile Val
                100                 105                 110

His Pro Tyr
        115

<210> SEQ ID NO 71
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 71

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
             35                  40                  45

Leu Ile Gln Gly Trp Gln Arg Glu Gln Thr Ser Gly Arg Leu Asn Ala
         50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Thr
                 85                  90                  95

Gly Gly Ala Tyr Ile Pro Thr Phe Gly Arg Gly Thr Ser Leu Ile Val
```

His Pro Tyr
    115

<210> SEQ ID NO 72
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 72

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Arg Glu
                85                  90                  95

Ser Gly Asn Tyr Ile Pro Thr Phe Gly Arg Gly Thr Ser Leu Ile Val
            100                 105                 110

His Pro Tyr
    115

<210> SEQ ID NO 73
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 73

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ile Ser
                85                  90                  95

Gly Gly Asp Tyr Ile Pro Thr Phe Gly Arg Gly Thr Ser Leu Ile Val
            100                 105                 110

His Pro Tyr
    115

<210> SEQ ID NO 74
<211> LENGTH: 115
<212> TYPE: PRT

<213> ORGANISM: Artificial Sequence
<220> FEATURE:
<223> OTHER INFORMATION: High affinity variant of 1G4 TCR alpha chain
     variable domain AA sequence

<400> SEQUENCE: 74

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala His
                85                  90                  95

Asn Gly Asn Tyr Ile Pro Thr Phe Gly Arg Gly Thr Ser Leu Ile Val
                100                 105                 110

His Pro Tyr
        115

<210> SEQ ID NO 75
<211> LENGTH: 116
<212> TYPE: PRT
<213> ORGANISM: Artificial Sequence
<220> FEATURE:
<223> OTHER INFORMATION: High affinity variant of 1G4 TCR alpha chain
     variable domain AA sequence

<400> SEQUENCE: 75

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Asp Asn
                85                  90                  95

Thr Trp Gly Thr Tyr Ile Pro Thr Phe Gly Arg Gly Thr Ser Leu Ile
                100                 105                 110

Val His Pro Tyr
        115

<210> SEQ ID NO 76
<211> LENGTH: 115
<212> TYPE: PRT
<213> ORGANISM: Artificial Sequence
<220> FEATURE:
<223> OTHER INFORMATION: High affinity variant of 1G4 TCR alpha chain
     variable domain AA sequence

<400> SEQUENCE: 76

Met Gln Glu Val Thr Gln Ile Pro Ala Ala Leu Ser Val Pro Glu Gly
1               5                   10                  15

```
Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Val Glu
                85                  90                  95

Gly Gly Asp Tyr Ile Pro Thr Phe Gly Arg Gly Thr Ser Leu Ile Val
                100                 105                 110

His Pro Tyr
        115
```

<210> SEQ ID NO 77
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 77

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Ala
                85                  90                  95

Ser Gly Asn Tyr Ile Pro Thr Phe Gly Arg Gly Thr Ser Leu Ile Val
                100                 105                 110

His Pro Tyr
        115
```

<210> SEQ ID NO 78
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 78

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
50                  55                  60
```

```
Ser Leu Asp Lys Ser Ser Gly Arg Ser Thr Leu Tyr Ile Ala Ala Ser
 65                 70                  75                  80

Gln Pro Gly Asp Ser Ala Thr Tyr Leu Cys Ala Val Arg Pro Ile Ser
                 85                  90                  95

Gly Gly Glu Tyr Ile Pro Thr Phe Gly Arg Gly Thr Ser Leu Ile Val
            100                 105                 110

His Pro Tyr
        115

<210> SEQ ID NO 79
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 79

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                 70                  75                  80

Gln Pro Gly Asp Ser Ala Thr Tyr Leu Cys Ala Val Arg Pro Ile Thr
                 85                  90                  95

Gly Gly Gly Tyr Ile Pro Thr Phe Gly Arg Gly Thr Ser Leu Ile Val
            100                 105                 110

His Pro Tyr
        115

<210> SEQ ID NO 80
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 80

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                 70                  75                  80

Gln Pro Gly Asp Ser Ala Thr Tyr Leu Cys Ala Val Arg Pro Leu Lys
                 85                  90                  95

Gly Gly Ala Tyr Ile Pro Thr Phe Gly Arg Gly Thr Ser Leu Ile Val
            100                 105                 110
```

His Pro Tyr
    115

<210> SEQ ID NO 81
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 81

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Glu
                85                  90                  95

Gly Gly Ser Tyr Ile Pro Thr Phe Gly Arg Gly Thr Ser Leu Ile Val
            100                 105                 110

His Pro Tyr
    115

<210> SEQ ID NO 82
<211> LENGTH: 115
<212> TYPE: PRT
<213> ORGANISM: Artificial Sequence
<220> FEATURE:
<223> OTHER INFORMATION: High affinity variant of 1G4 TCR alpha chain
      variable domain AA sequence

<400> SEQUENCE: 82

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ser Thr
                85                  90                  95

Gly Gly Asn Tyr Ile Pro Thr Phe Gly Arg Gly Thr Ser Leu Ile Val
            100                 105                 110

His Pro Tyr
    115

<210> SEQ ID NO 83
<211> LENGTH: 116
<212> TYPE: PRT
<213> ORGANISM: Artificial Sequence

```
<220> FEATURE:
<223> OTHER INFORMATION: High affinity variant of 1G4 TCR alpha chain
      variable domain AA sequence

<400> SEQUENCE: 83

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Val Asp
                85                  90                  95

Asp Gly Gly Lys Tyr Ile Pro Thr Phe Gly Arg Gly Thr Ser Leu Ile
            100                 105                 110

Val His Pro Tyr
        115

<210> SEQ ID NO 84
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 84

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asn Thr Gly Glu Leu Phe Phe Gly Glu Gly Ser Arg Leu Thr Val Leu
            100                 105                 110

<210> SEQ ID NO 85
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 85

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30
```

```
Trp Tyr Arg Gln Asp Pro Gly Met Gly Leu Arg Leu Ile His Tyr Ser
            35                  40                  45

Val Gly Ala Gly Thr Thr Asp Gln Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
            85                  90                  95

Asn Thr Gly Glu Leu Phe Phe Gly Glu Gly Ser Arg Leu Thr Val Leu
           100                 105                 110
```

<210> SEQ ID NO 86
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 86

```
Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Gly Ala Gly Thr Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Asn Val Gly
            85                  90                  95

Asn Thr Gly Glu Leu Phe Phe Gly Glu Gly Ser Arg Leu Thr Val Leu
           100                 105                 110
```

<210> SEQ ID NO 87
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 87

```
Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Gly Ala Gly Thr Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
            85                  90                  95

Gly Thr Gly Glu Leu Phe Phe Gly Glu Gly Ser Arg Leu Thr Val Leu
           100                 105                 110
```

```
<210> SEQ ID NO 88
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 88

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

<210> SEQ ID NO 89
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 89

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asp Thr Gly Glu Leu Phe Phe Gly Glu Gly Ser Arg Leu Thr Val Leu
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 90

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
```

```
                    20                  25                  30

Trp Tyr Arg Gln Asp Pro Gly Met Gly Leu Arg Leu Ile His Tyr Ser
            35                  40                  45

Val Gly Val Gly Thr Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
            85                  90                  95

Asp Thr Gly Glu Leu Phe Phe Gly Glu Gly Ser Arg Leu Thr Val Leu
            100                 105                 110

<210> SEQ ID NO 91
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 91

Met Gly Val Thr Gln Thr Pro Lys Phe Gln Val Leu Lys Thr Gly Gln
1               5                   10                  15

Ser Val Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Gly Val Gly Thr Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
            85                  90                  95

Asp Thr Gly Glu Leu Phe Phe Gly Glu Gly Ser Arg Leu Thr Val Leu
            100                 105                 110

<210> SEQ ID NO 92
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 92

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Ser Val Gly Met Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
            85                  90                  95

Asn Thr Gly Glu Leu Phe Phe Gly Glu Gly Ser Arg Leu Thr Val Leu
```

-continued

```
                100             105             110
```

<210> SEQ ID NO 93
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 93

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
                100             105             110
```

<210> SEQ ID NO 94
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 94

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asn Thr Gly Glu Leu Phe Phe Gly Glu Gly Ser Arg Leu Thr Val Leu
                100             105             110
```

<210> SEQ ID NO 95
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 95

```
Met Gly Val Thr Gln Thr Pro Lys Phe Gln Val Leu Lys Thr Gly Gln
1               5                   10                  15
```

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ser Val Gly Met Thr Asp Gln Gly Glu Val Pro Asn Gly Tyr Asn
50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
            85                  90                  95

Asn Thr Gly Glu Leu Phe Phe Gly Glu Gly Ser Arg Leu Thr Val Leu
            100                 105                 110

<210> SEQ ID NO 96
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 96

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
            85                  90                  95

Val Thr Gly Glu Leu Phe Phe Gly Glu Gly Ser Arg Leu Thr Val Leu
            100                 105                 110

<210> SEQ ID NO 97
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 97

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
            85                  90                  95

Asp Thr Gly Glu Leu Phe Phe Gly Glu Gly Ser Arg Leu Thr Val Leu
            100                 105                 110

<210> SEQ ID NO 98
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 98

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
            85                  90                  95

Asp Thr Gly Glu Leu Phe Phe Gly Glu Gly Ser Arg Leu Thr Val Leu
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 99

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Phe Val Gly
            85                  90                  95

Asp Thr Gly Glu Leu Phe Phe Gly Glu Gly Ser Arg Leu Thr Val Leu
            100                 105                 110

<210> SEQ ID NO 100
<211> LENGTH: 47
<212> TYPE: PRT
<213> ORGANISM: Artificial Sequence
<220> FEATURE:
<223> OTHER INFORMATION: Amino acid sequence of a soluble form of TRAC

<400> SEQUENCE: 100

Asn Ile Gln Asn Pro Asp Pro Ala Val Tyr Gln Leu Arg Asp Ser Lys

```
                1               5                  10                  15
Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys
                35                  40                  45
```

<210> SEQ ID NO 101
<211> LENGTH: 56
<212> TYPE: PRT
<213> ORGANISM: Artificial Sequence
<220> FEATURE:
<223> OTHER INFORMATION: Amino acid sequence of a soluble form of TRBC1

<400> SEQUENCE: 101

```
Glu Asp Leu Asn Lys Val Phe Pro Pro Glu Val Ala Val Phe Glu Pro
1               5                  10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
                35                  40                  45

Gly Lys Glu Val His Ser Gly Val
                50                  55
```

<210> SEQ ID NO 102
<211> LENGTH: 56
<212> TYPE: PRT
<213> ORGANISM: Artificial Sequence
<220> FEATURE:
<223> OTHER INFORMATION: Amino acid sequence of a soluble form of TRBC2

<400> SEQUENCE: 102

```
Glu Asp Leu Lys Asn Val Phe Pro Pro Glu Val Ala Val Phe Glu Pro
1               5                  10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
                35                  40                  45

Gly Lys Glu Val His Ser Gly Val
                50                  55
```

<210> SEQ ID NO 103
<211> LENGTH: 30
<212> TYPE: PRT
<213> ORGANISM: Artificial Sequence
<220> FEATURE:
<223> OTHER INFORMATION: Short scTCR linker

<400> SEQUENCE: 103

```
Pro Gly Gly Gly Ser Gly Gly Gly Gly Ser Gly Gly Gly Gly Ser Gly
1               5                  10                  15

Gly Gly Gly Ser Gly Gly Gly Ser Gly Gly Gly Gly Pro
                20                  25                  30
```

<210> SEQ ID NO 104
<211> LENGTH: 35
<212> TYPE: PRT
<213> ORGANISM: Artificial Sequence
<220> FEATURE:
<223> OTHER INFORMATION: Long scTCR linker

<400> SEQUENCE: 104

```
Pro Gly Gly Gly Ser Gly Gly Gly Gly Ser Gly Gly Gly Gly Ser Gly
```

```
                1               5                      10                      15
            Gly Gly Gly Ser Gly Gly Gly Ser Gly Gly Gly Ser Gly Gly
                        20                      25                      30
            Gly Gly Pro
                    35
```

<210> SEQ ID NO 105
<211> LENGTH: 37
<212> TYPE: DNA
<213> ORGANISM: Artificial Sequence
<220> FEATURE:
<223> OTHER INFORMATION: Primer

<400> SEQUENCE: 105
tctctcatta atgaaacagg aggtgacgca gattcct                           37

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
cggcagggtc agggttctgg                                              20

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
ccagaaccct gaccctgccg                                              20

<210> SEQ ID NO 108
<211> LENGTH: 30
<212> TYPE: DNA
<213> ORGANISM: Artificial Sequence
<220> FEATURE:
<223> OTHER INFORMATION: Primer

<400> SEQUENCE: 108
aagcttcccg ggggaacttt ctgggctggg                                   30

<210> SEQ ID NO 109
<211> LENGTH: 36
<212> TYPE: DNA
<213> ORGANISM: Artificial Sequence
<220> FEATURE:
<223> OTHER INFORMATION: Primer

<400> SEQUENCE: 109
tctctcatta atgaatgctg gtgtcactca gacccc                            36

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
cttctgatgg ctcaaacaca gc                                           22

<210> SEQ ID NO 111
<211> LENGTH: 22
<212> TYPE: DNA
<213> ORGANISM: Artificial Sequence
<220> FEATURE:
<223> OTHER INFORMATION: Primer

<400> SEQUENCE: 111
gctgtgtttg agccatcaga ag                                              22

<210> SEQ ID NO 112
<211> LENGTH: 30
<212> TYPE: DNA
<213> ORGANISM: Artificial Sequence
<220> FEATURE:
<223> OTHER INFORMATION: Primer

<400> SEQUENCE: 112
aagcttcccg gggtctgctc tacccaggc                                        30

<210> SEQ ID NO 113
<211> LENGTH: 3342
<212> TYPE: DNA
<213> ORGANISM: Artificial Sequence
<220> FEATURE:
<223> OTHER INFORMATION: pEX954 Vector

<400> SEQUENCE: 113
gatctcgatc ccgcgaaatt aatacgactc actataggga gaccacaacg gtttccctct      60
agaaataatt ttgtttaact ttaagaagga gatataatcg atgtctaact cgagtgacaa     120
gtctgtctgc ctattcaccg attttgattc tcaaacaaat gtgtcacaaa gtaaggattc     180
tgatgtgtat atcacagaca aatgtgtgct agacatgagg tctatggact tcaagagcaa     240
cagtgctgtg gcctggagca acaaatctga ctttgcatgt gcaacgcct tcaacaacag     300 cattattcca gaagacacct tcttccccag cccagaaagt tcctaagctt gaattccgat     360
ccggctgcta acaaagcccg aaaggaagct gagttggctg ctgccaccgc tgagcaataa     420
ctagcataac cccttggggc ctctaaacgg gtcttgaggg gttttttgct gaaaggagga     480
actatatccg gataattctt gaagacgaaa gggcctcgtg atacgcctat ttttataggt     540
taatgtcatg ataataatgg tttcttagac gtgaggtggc acttttcggg gaaatgtgcg     600
cggaacccct atttgtttat ttttctaaat acattcaaat atgtatccgc tcatgagaca     660
ataaccctga taaatgcttc aataatattt tgttaaaatt cgcgttaaat ttttgttaaa     720
tcagctcatt ttttaaccaa taggccgaaa tcggcaaaat cccttataaa tcaaaagaat     780
agaccgagat agggttgagt gttgttccag tttggaacaa gagtccacta ttaaagaacg     840
tggactccaa cgtcaaaggg cgaaaaaccg tctatcaggg cgatggccca ctacgtgaac     900
catcacccta atcaagtttt tggggtcga ggtgccgtaa agcactaaat cggaacccta     960
aagggagccc ccgatttaga gcttgacggg gaaagccggc gaacgtggcg agaaaggaag    1020
ggaagaaagc gaaaggagcg ggcgctaggg cgctggcaag tgtagcggtc acgctgcgcg    1080
taaccaccac acccgccgcg cttaatgcgc cgctacaggg cgcgtcaggt ggcacttttc    1140
ggggaaatgt gcgcggaacc cctatttgtt tatttttcta atacattca aatatgtatc    1200 cgctcatgag acaataaccc tgataaatgc ttcaataata ttgaaaaagg aagagtatga    1260
gtattcaaca tttccgtgtc gcccttattc ccttttttgc ggcattttgc cttcctgttt    1320

```
ttgctcaccc agaaacgctg gtgaaagtaa aagatgctga agatcagttg ggtgcacgag      1380
tgggttacat cgaactggat ctcaacagcg gtaagatcct tgagagtttt cgccccgaag      1440
aacgttttcc aatgatgagc acttttaaag ttctgctatg tggcgcggta ttatcccgtg      1500
ttgacgccgg gcaagagcaa ctcggtcgcc gcatacacta ttctcagaat gacttggttg      1560
agtactcacc agtcacagaa aagcatctta cggatggcat gacagtaaga gaattatgca      1620
gtgctgccat aaccatgagt gataacactg cggccaactt acttctgaca acgatcggag      1680
gaccgaagga gctaaccgct tttttgcaca acatggggga tcatgtaact cgccttgatc      1740
gttgggaacc ggagctgaat gaagccatac caaacgacga gcgtgacacc acgatgcctg      1800
cagcaatggc aacaacgttg cgcaaactat taactggcga actacttact ctagcttccc      1860
ggcaacaatt aatagactgg atggaggcgg ataaagttgc aggaccactt ctgcgctcgg      1920
cccttccggc tggctggttt attgctgata atctggagc cggtgagcgt gggtctcgcg      1980
gtatcattgc agcactgggg ccagatggta agccctcccg tatcgtagtt atctacacga      2040
cggggagtca ggcaactatg gatgaacgaa atagacagat cgctgagata ggtgcctcac      2100
tgattaagca ttggtaactg tcagaccaag tttactcata tatactttag attgatttaa      2160
aacttcattt ttaattttaaa aggatctagg tgaagatcct ttttgataat ctcatgacca      2220
aaatccctta acgtgagttt tcgttccact gagcgtcaga ccccgtagaa aagatcaaag      2280
gatcttcttg agatcctttt tttctgcgcg taatctgctg cttgcaaaca aaaaaaccac      2340
cgctaccagc ggtggtttgt ttgccggatc aagagctacc aactcttttt ccgaaggtaa      2400
ctggcttcag cagagcgcag ataccaaata ctgtccttct agtgtagccg tagttaggcc      2460
accacttcaa gaactctgta gcaccgccta catacctcgc tctgctaatc ctgttaccag      2520
tggctgctgc cagtggcgat aagtcgtgtc ttaccgggtt ggactcaaga cgatagttac      2580
cggataaggc gcagcggtcg ggctgaacgg ggggttcgtg cacacagccc agcttggagc      2640
gaacgaccta caccgaactg agatacctac agcgtgagct atgagaaagc gccacgcttc      2700
ccgaagggag aaaggcggac aggtatccgg taagcggcag ggtcggaaca ggagagcgca      2760
cgagggagct tccaggggga aacgcctggt atctttatag tcctgtcggg tttcgccacc      2820
tctgacttga gcgtcgattt ttgtgatgct cgtcaggggg cggagcctat ggaaaaacg      2880 ccagcaacgc ggccttttta cggttcctgg ccttttgctg ccttttgct cacatgttct      2940 ttcctgcgtt atcccctgat tctgtggata accgtattac cgcctttgag tgagctgata      3000
ccgctcgccg cagccgaacg accgagcgca gcgagtcagt gagcgaggaa gcggaagagc      3060
gcctgatgcg gtattttctc cttacgcatc tgtgcggtat ttcacaccgc aatggtgcac      3120
tctcagtaca atctgctctg atgccgcata gttaagccag tatacactcc gctatcgcta      3180
cgtgactggg tcatggctgc gccccgacac ccgccaacac ccgctgacgc gccctgacgg      3240
gcttgtctgc tcccggcatc cgcttacaga caagctgtga ccgtctccgg gagctgcatg      3300
tgtcagaggt tttcaccgtc atcaccgaaa cgcgcgaggc ag                        3342
```

<210> SEQ ID NO 114
<211> LENGTH: 3836
<212> TYPE: DNA
<213> ORGANISM: Artificial Sequence
<220> FEATURE:
<223> OTHER INFORMATION: pEX821 Vector

<400> SEQUENCE: 114

```
gatctcgatc ccgcgaaatt aatacgactc actatagggg accacaacg gtttccctct       60
```

```
agaaataatt ttgtttaact ttaagaagga gatatacata tgaacgctgg tgtcactcag    120
accccaaaat tccaggtcct gaagacagga cagagcatga cactgcagtg tgcccaggat    180
atgaaccatg aatacatgtc ctggtatcga caagacccag gcatggggct gaggctgatt    240
cattactcag ttggtgctgg tatcactgac caaggagaag tccccaatgg ctacaatgtc    300
tccagatcaa ccacagagga tttcccgctc aggctgctgt cggctgctcc ctcccagaca    360
tctgtgtact tctgtgccag caggccggga ctagcgggag gcgaccaga gcagtacttc    420 gggccgggca ccaggctcac ggtcacagag gacctgaaaa acgtgttccc acccgaggtc    480
gctgtgtttg agccatcaga agcagagatc tcccacaccc aaaaggccac actggtgtgc    540
ctggccaccg gtttctaccc cgaccacgtg gagctgagct ggtgggtgaa tgggaaggag    600
gtgcacagtg gggtctgcac agacccgcag ccccctcaagg agcagcccgc cctcaatgac    660
tccagatacg ctctgagcag ccgcctgagg gtctcggcca ccttctggca ggaccccgcc    720
aaccacttcc gctgtcaagt ccagttctac gggctctcgg agaatgacga gtggacccag    780
gatagggcca aaccgtcac ccagatcgtc agcgccgagg cctggggtag agcagactaa    840
gcttgaattc cgatccggct gctaacaaag cccgaaagga agctgagttg gctgctgcca    900
ccgctgagca ataactagca taaccccttg gggcctctaa acgggtcttg aggggttttt    960
tgctgaaagg aggaactata tccggataat tcttgaagac gaaagggcct cgtgatacgc   1020
ctatttttat aggttaatgt catgataata atggtttctt agacgtcagg tggcactttt   1080
cggggaaatg tgcgcggaac ccctatttgt ttatttttct aaatacattc aaatatgtat   1140
ccgctcatga caataaccc ctgataaatg cttcaataat attttgttaa aattcgcgtt   1200
aaatttttgt taaatcagct cattttttaa ccaataggcc gaaatcggca aaatccctta   1260
taaatcaaaa gaatagaccg agatagggtt gagtgttgtt ccagtttgga acaagagtcc   1320
actattaaag aacgtggact ccaacgtcaa agggcgaaaa accgtctatc agggcgatgg   1380
cccactacgt gaaccatcac cctaatcaag ttttttgggg tcgaggtgcc gtaaagcact   1440
aaatcggaac cctaaaggga gcccccgatt tagagcttga cggggaaagc cggcgaacgt   1500
ggcgagaaag gaagggaaga agcgaaagg agcgggcgct agggcgctgg caagtgtagc   1560
ggtcacgctg cgcgtaacca ccacacccgc cgcgcttaat gcgccgctac agggcgcgtc   1620
aggtggcact tttcggggaa atgtgcgcgg aaccccattt tgtttatttt tctaaataca   1680
ttcaaatatg tatccgctca tgagacaata accctgataa atgcttcaat aatattgaaa   1740
aaggaagagt atgagtattc aacatttccg tgtcgccctt attccctttt ttgcggcatt   1800
ttgccttcct gtttttgctc acccagaaac gctggtgaaa gtaaaagatg ctgaagatca   1860
gttgggtgca cgagtgggtt acatcgaact ggatctcaac agcggtaaga tccttgagag   1920
ttttcgcccc gaagaacgtt ttccaatgat gagcactttt aaagttctgc tatgtggcgc   1980
ggtattatcc cgtgttgacg ccgggcaaga gcaactcggt cgccgcatac actattctca   2040
gaatgacttg gttgagtact caccagtcac agaaaagcat cttacggatg gcatgacagt   2100
aagagaatta tgcagtgctg ccataaccat gagtgataac actgcggcca acttacttct   2160
gacaacgatc ggaggaccga aggagctaac cgcttttttg cacaacatgg ggatcatgt    2220 aactcgcctt gatcgttggg aaccggagct gaatgaagcc ataccaaacg acgagcgtga   2280
caccacgatg cctgcagcaa tggcaacaac gttgcgcaaa ctattaactg gcgaactact   2340
tactctagct tcccggcaac aattaataga ctggatggag gcggataaag ttgcaggacc   2400
```

| | |
|---|---|
| acttctgcgc tcggcccttc cggctggctg gtttattgct gataaatctg gagccggtga | 2460 |
| gcgtgggtct cgcggtatca ttgcagcact ggggccagat ggtaagccct cccgtatcgt | 2520 |
| agttatctac acgacgggga gtcaggcaac tatggatgaa cgaaatagac agatcgctga | 2580 |
| gataggtgcc tcactgatta agcattggta actgtcagac caagtttact catatatact | 2640 |
| ttagattgat ttaaaacttc attttttaatt taaaaggatc taggtgaaga tcctttttga | 2700 |
| taatctcatg accaaaatcc cttaacgtga gttttcgttc cactgagcgt cagaccccgt | 2760 |
| agaaaagatc aaaggatctt cttgagatcc ttttttttctg cgcgtaatct gctgcttgca | 2820 |
| aacaaaaaaa ccaccgctac cagcggtggt ttgtttgccg gatcaagagc taccaactct | 2880 |
| ttttccgaag gtaactggct tcagcagagc gcagatacca atactgtcc ttctagtgta | 2940 |
| gccgtagtta ggccaccact tcaagaactc tgtagcaccg cctacatacc tcgctctgct | 3000 |
| aatcctgtta ccagtggctg ctgccagtgg cgataagtcg tgtcttaccg ggttggactc | 3060 |
| aagacgatag ttaccggata aggcgcagcg gtcgggctga acggggggtt cgtgcacaca | 3120 |
| gcccagcttg gagcgaacga cctacaccga actgagatac ctacagcgtg agctatgaga | 3180 |
| aagcgccacg cttcccgaag ggagaaaggc ggacaggtat ccggtaagcg gcagggtcgg | 3240 |
| aacaggagag cgcacgaggg agcttccagg gggaaacgcc tggtatcttt atagtcctgt | 3300 |
| cgggtttcgc cacctctgac ttgagcgtcg atttttgtga tgctcgtcag ggggggcggag | 3360 |
| cctatggaaa aacgccagca acgcggcctt tttacggttc ctggccttttt gctgccttt | 3420 |
| tgctcacatg ttctttcctg cgttatcccc tgattctgtg ataaccgta ttaccgcctt | 3480 |
| tgagtgagct gataccgctc gccgcagccg aacgaccgag cgcagcgagt cagtgagcga | 3540 |
| ggaagcggaa gagcgcctga tgcggtattt tctccttacg catctgtgcg gtatttcaca | 3600 |
| ccgcaatggt gcactctcag tacaatctgc tctgatgccg catagttaag ccagtataca | 3660 |
| ctccgctatc gctacgtgac tgggtcatgg ctgcgccccg acacccgcca cacccgctg | 3720 |
| acgcccctg acgggcttgt ctgctcccgg catccgctta cagacaagct gtgaccgtct | 3780 |
| ccgggagctg catgtgtcag aggttttcac cgtcatcacc gaaacgcgcg aggcag | 3836 |

<210> SEQ ID NO 115
<211> LENGTH: 3857
<212> TYPE: DNA
<213> ORGANISM: Artificial Sequence
<220> FEATURE:
<223> OTHER INFORMATION: pEX202 Vector

<400> SEQUENCE: 115

| | |
|---|---|
| gatctcgatc ccgcgaaatt aatacgactc actatagga gaccacaacg gtttccctct | 60 |
| agaaataatt ttgtttaact ttaagaagga gatatacata tgcagaagga agtggagcag | 120 |
| aactctggac ccctcagtgt tccagaggga gccattgcct ctctcaactg cacttacagt | 180 |
| gaccgaggtt cccagtcctt cttctggtac agacaatatt ctgggaaaag ccctgagttg | 240 |
| ataatgtcca tatactccaa tggtgacaaa gaagatggaa ggtttacagc acagctcaat | 300 |
| aaagccagcc agtatgtttc tctgctcatc agagactccc agcccagtga ttcagccacc | 360 |
| tacctctgtg ccgttacaac tgacagctgg gggaaattgc agtttggagc agggaccccag | 420 |
| gttgtggtca ccccagatat ccagaaccct gaccctgccg tgtaccagct gagagactct | 480 |
| aaatccagtg acaagtctgt ctgcctattc accgattttg attctcaaac aaatgtgtca | 540 |
| caaagtaagg attctgatgt gtatatcaca gacaaaactg tgctagacat gaggtctatg | 600 |
| gacttcaaga gcaacagtgc tgtggcctgg agcaacaaat ctgactttgc atgtgcaaac | 660 |

```
gccttcaaca acagcattat tccagaagac accttcttcc ccagcccaga aagttccccc    720
gggggtagaa tcgcccggct ggaggaaaaa gtgaaaacct tgaaagctca gaactcggag    780
ctggcgtcca cggccaacat gctcagggaa caggtggcac agcttaaaca gaaagtcatg    840
aactactagg atccatggta agcttgaatt ccgatccggc tgctaacaaa gcccgaaagg    900
aagctgagtt ggctgctgcc accgctgagc aataactagc ataacccctt ggggcctcta    960
aacgggtctt gaggggtttt tgctgaaagg aggaactat atccggataa ttcttgaaga    1020
cgaaagggcc tcgtgatacg cctattttta taggttaatg tcatgataat aatggtttct    1080
tagacgtcag gtggcacttt tcggggaaat gtgcgcggaa cccctatttg tttattttc     1140 taaatacatt caaatatgta tccgctcatg agacaataac cctgataaat gcttcaataa    1200
tattttgtta aaattcgcgt taaattttg ttaaatcagc tcattttta accaataggc      1260 cgaaatcggc aaaatccctt ataaatcaaa agaatagacc gagatagggt tgagtgttgt    1320
tccagtttgg aacaagagtc cactattaaa gaacgtggac tccaacgtca aagggcgaaa    1380
aaccgtctat cagggcgatg gcccactacg tgaaccatca cctaatcaa gttttttggg     1440 gtcgaggtgc cgtaaagcac taaatcggaa ccctaaaggg agccccgat ttagagcttg      1500 acggggaaag ccggcgaacg tggcgagaaa ggaagggaag aaagcgaaag gagcgggcgc    1560
tagggcgctg gcaagtgtag cggtcacgct gcgcgtaacc accacacccg ccgcgcttaa    1620
tgcgccgcta cagggcgcgt caggtggcac ttttcgggga atgtgcgcg gaacccctat      1680 ttgtttattt ttctaaatac attcaaatat gtatccgctc atgagacaat aaccctgata    1740
aatgcttcaa taatattgaa aaggaagag tatgagtatt caacatttcc gtgtcgccct     1800
tattcccttt tttgcggcat tttgccttcc tgtttttgct cacccagaaa cgctggtgaa    1860
agtaaaagat gctgaagatc agttgggtgc acgagtgggt tacatcgaac tggatctcaa    1920
cagcggtaag atccttgaga gttttcgccc cgaagaacgt tttccaatga tgagcacttt    1980
taaagttctg ctatgtggcg cggtattatc ccgtgttgac gccgggcaag agcaactcgg    2040
tcgccgcata cactattctc agaatgactt ggttgagtac tcaccagtca cagaaaagca    2100
tcttacggat ggcatgacag taagagaatt atgcagtgct gccataacca tgagtgataa    2160
cactgcggcc aacttacttc tgacaacgat cggaggaccg aaggagctaa ccgcttttt     2220 gcacaacatg gggatcatg taactcgcct tgatcgttgg gaaccggagc tgaatgaagc      2280
cataccaaac gacgagcgtg acaccacgat gcctgcagca atggcaacaa cgttgcgcaa    2340
actattaact ggcgaactac ttactctagc ttcccggcaa caattaatag actggatgga    2400
ggcggataaa gttgcaggac cacttctgcg ctcggccctt ccggctggct ggtttattgc    2460
tgataaatct ggagccggtg agcgtgggtc tcgcggtatc attgcagcac tggggccaga    2520
tggtaagccc tcccgtatcg tagttatcta cacgacgggg agtcaggcaa ctatggatga    2580
acgaaataga cagatcgctg agataggtgc ctcactgatt aagcattggt aactgtcaga    2640
ccaagtttac tcatatatac tttagattga tttaaaactt catttttaat ttaaaaggat    2700
ctaggtgaag atccttttg ataatctcat gaccaaaatc ccttaacgtg agttttcgtt     2760
ccactgagcg tcagaccccg tagaaaagat caaaggatct tcttgagatc ctttttttct    2820
gcgcgtaatc tgctgcttgc aaacaaaaaa accaccgcta ccagcggtgg tttgtttgcc    2880
ggatcaagag ctaccaactc tttttccgaa ggtaactggc ttcagcagag cgcagatacc    2940
aaatactgtc cttctagtgt agccgtagtt aggccaccac ttcaagaact ctgtagcacc    3000
```

```
gcctacatac ctcgctctgc taatcctgtt accagtggct gctgccagtg gcgataagtc    3060
gtgtcttacc ggggttggact caagacgata gttaccggat aaggcgcagc ggtcgggctg   3120
aacgggggt tcgtgcacac agcccagctt ggagcgaacg acctacaccg aactgagata     3180
cctacagcgt gagctatgag aaagcgccac gcttcccgaa gggagaaagg cggacaggta    3240
tccggtaagc ggcagggtcg aacaggaga gcgcacgagg gagcttccag ggggaaacgc     3300
ctggtatctt tatagtcctg tcgggtttcg ccacctctga cttgagcgtc gattttttgtg  3360
atgctcgtca ggggggcgga gcctatggaa aaacgccagc aacgcggcct ttttacggtt   3420
cctggccttt tgctggcctt ttgctcacat gttctttcct gcgttatccc ctgattctgt   3480
ggataaccgt attaccgcct ttgagtgagc tgataccgct cgccgcagcc gaacgaccga   3540
gcgcagcgag tcagtgagcg aggaagcgga agagcgcctg atgcggtatt ttctccttac   3600
gcatctgtgc ggtatttcac accgcaatgg tgcactctca gtacaatctg ctctgatgcc   3660
gcatagttaa gccagtatac actccgctat cgctacgtga ctgggtcatg gctgcgcccc   3720
gacacccgcc aacacccgct gacgcgccct gacgggcttg tctgctcccg gcatccgctt   3780
acagacaagc tgtgaccgtc tccgggagct gcatgtgtca gaggttttca ccgtcatcac   3840
cgaaacgcgc gaggcag                                                  3857

<210> SEQ ID NO 116
<211> LENGTH: 4019
<212> TYPE: DNA
<213> ORGANISM: Artificial Sequence
<220> FEATURE:
<223> OTHER INFORMATION: pEX205

<400> SEQUENCE: 116
gatctcgatc ccgcgaaatt aatacgactc actataggga gaccacaacg gtttccctct     60
agaaataatt ttgtttaact ttaagaagga gatatacata tgaacgctgg tgtcactcag    120
accccaaaat tccaggtcct gaagacagga cagagcatga cactgcagtg tgcccaggat   180
atgaaccatg aatacatgtc ctggtatcga caagacccag gcatggggct gaggctgatt   240
cattactcag ttggtgctgg tatcactgac caaggagaag tccccaatgg ctacaatgtc   300
tccagatcaa ccacagagga tttcccgctc aggctgctgt cggctgctcc ctcccagaca   360
tctgtgtact ctgtgccag caggccggga ctagcgggag ggcgaccaga gcagtacttc    420
gggccgggca ccaggctcac ggtcacagag acctgaaaa acgtgttccc acccgaggtc    480
gctgtgtttg agccatcaga agcagagatc tcccacaccc aaaaggccac actggtgtgc   540
ctggccacag gcttctaccc cgaccacgtg agctgagct ggtgggtgaa tgggaaggag    600
gtgcacagtg gggtcagcac agaccccgca ccccctcaagg agcagcccgc ctcaatgac   660
tccagatacg ctctgagcag ccgcctgagg gtctcggcca ccttctggca ggaccccgc    720
aaccacttcc gctgtcaagt ccagttctac gggctctcgg agaatgacga gtggacccag    780
gatagggcca aacccgtcac ccagatcgtc agcgccgagg cctgggggtag agcagacccc   840
gggggtctga ctgatacact ccaagcggag acagatcaac ttgaagacaa gaagtctgcg    900
ttgcagaccg agattgccaa tctactgaaa gagaaggaaa aactagagtt catcctggca   960
gcttacggat ccggtggtgg tctgaacgat atttttgaag ctcagaaaat cgaatggcat   1020
taagcttgaa ttccgatccg gctgctaaca aagcccgaaa ggaagctgag ttggctgctg   1080
ccaccgctga gcaataacta gcataacccc ttggggcctc taaacgggtc ttgaggggtt   1140
ttttgctgaa aggaggaact atatccggat aattcttgaa gacgaaaggg cctcgtgata   1200
```

```
cgcctatttt tataggttaa tgtcatgata ataatggttt cttagacgtc aggtggcact   1260
tttcggggaa atgtgcgcgg aaccccctatt tgtttatttt tctaaataca ttcaaatatg   1320
tatccgctca tgagacaata accctgataa atgcttcaat aatattttgt taaaattcgc   1380
gttaaatttt tgttaaatca gctcattttt taaccaatag gccgaaatcg gcaaaatccc   1440
ttataaatca aaagaataga ccgagatagg gttgagtgtt gttccagttt ggaacaagag   1500
tccactatta aagaacgtgg actccaacgt caaagggcga aaaaccgtct atcagggcga   1560
tggcccacta cgtgaaccat caccctaatc aagttttttg gggtcgaggt gccgtaaagc   1620
actaaatcgg aaccctaaag ggagcccccg atttagagct tgacggggaa agccggcgaa   1680
cgtggcgaga aggaaggga agaaagcgaa aggagcgggc gctagggcgc tggcaagtgt   1740
agcggtcacg ctgcgcgtaa ccaccacacc cgccgcgctt aatgcgccgc tacagggcgc   1800
gtcaggtggc acttttcggg gaaatgtgcg cggaaccccct atttgtttat ttttctaaat   1860
acattcaaat atgtatccgc tcatgagaca ataaccctga taaatgcttc aataatattg   1920
aaaaaggaag agtatgagta ttcaacattt ccgtgtcgcc cttattccct ttttttgcggc   1980
attttgcctt cctgtttttg ctcacccaga aacgctggtg aaagtaaaag atgctgaaga   2040
tcagttgggt gcacgagtgg gttacatcga actggatctc aacagcggta agatccttga   2100
gagttttcgc cccgaagaac gttttccaat gatgagcact tttaaagttc tgctatgtgg   2160
cgcggtatta tcccgtgttg acgccgggca agagcaactc ggtcgccgca tacactattc   2220
tcagaatgac ttggttgagt actcaccagt cacagaaaag catcttacgg atggcatgac   2280
agtaagagaa ttatgcagtg ctgccataac catgagtgat aacactgcgg ccaacttact   2340
tctgacaacg atcggaggac cgaaggagct aaccgctttt ttgcacaaca tgggggatca   2400
tgtaactcgc cttgatcgtt gggaaccgga gctgaatgaa gccataccaa acgacgagcg   2460
tgacaccacg atgcctgcag caatggcaac aacgttgcgc aaactattaa ctggcgaact   2520
acttactcta gcttcccggc aacaattaat agactggatg gaggcggata agttgcagg   2580
accacttctg cgctcggccc ttccggctgg ctggtttatt gctgataaat ctggagccgg   2640
tgagcgtggg tctcgcggta tcattgcagc actggggcca gatggtaagc cctcccgtat   2700
cgtagttatc tacacgacgg ggagtcaggc aactatggat gaacgaaata gacagatcgc   2760
tgagataggt gcctcactga ttaagcattg gtaactgtca gaccaagttt actcatatat   2820
actttagatt gatttaaaac ttcatttta atttaaaagg atctaggtga agatccttt   2880
tgataatctc atgaccaaaa tcccttaacg tgagttttcg ttccactgag cgtcagaccc   2940
cgtagaaaag atcaaaggat cttcttgaga tccttttttt ctgcgcgtaa tctgctgctt   3000
gcaaacaaaa aaaccaccgc taccagcggt ggtttgtttg ccggatcaag agctaccaac   3060
tcttttttccg aaggtaactg gcttcagcag agcgcagata ccaaatactg tccttctagt   3120
gtagccgtag ttaggccacc acttcaagaa ctctgtagca ccgcctacat acctcgctct   3180
gctaatcctg ttaccagtgg ctgctgccag tggcgataag tcgtgtctta ccgggttgga   3240
ctcaagacga tagttaccgg ataaggcgca gcggtcgggc tgaacggggg gttcgtgcac   3300
acagcccagc ttggagcgaa cgacctacac cgaactgaga tacctacagc gtgagctatg   3360
agaaagcgcc acgcttcccg aagggagaaa ggcggacagg tatccggtaa gcggcagggt   3420
cggaacagga gagcgcacga gggagcttcc agggggaaac gcctggtatc tttatagtcc   3480
tgtcgggttt cgccacctct gacttgagcg tcgatttttg tgatgctcgt cagggggggcg   3540
```

```
gagcctatgg aaaaacgcca gcaacgcggc cttttttacgg ttcctggcct tttgctggcc    3600
ttttgctcac atgttcttc  ctgcgttatc ccctgattct gtggataacc gtattaccgc    3660
ctttgagtga gctgataccg ctcgccgcag ccgaacgacc gagcgcagcg agtcagtgag    3720
cgaggaagcg gaaagcgcc  tgatgcggta ttttctcctt acgcatctgt gcggtatttc    3780
acaccgcaat ggtgcactct cagtacaatc tgctctgatg ccgcatagtt aagccagtat    3840
acactccgct atcgctacgt gactgggtca tggctgcgcc ccgacacccg ccaacacccg    3900
ctgacgcgcc ctgacgggct tgtctgctcc cggcatccgc ttacagacaa gctgtgaccg    3960
tctccgggag ctgcatgtgt cagaggtttt caccgtcatc accgaaacgc gcgaggcag    4019
```

<210> SEQ ID NO 117
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 117

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asp Thr Gly Glu Leu Phe Phe Gly Glu Gly Ser Arg Leu Thr Val Leu
            100                 105                 110
```

<210> SEQ ID NO 118
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 118

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asn Thr Gly Glu Leu Phe Phe Gly Glu Gly Ser Arg Leu Thr Val Leu
            100                 105                 110
```

<210> SEQ ID NO 119
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 119

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

<210> SEQ ID NO 120
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 120

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ser Val Gly Met Thr Asp Arg Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asp Thr Gly Glu Leu Phe Phe Gly Glu Gly Ser Arg Leu Thr Val Leu
            100                 105                 110

<210> SEQ ID NO 121
<211> LENGTH: 112
<212> TYPE: PRT
<213> ORGANISM: Artificial Sequence
<220> FEATURE:
<223> OTHER INFORMATION: High affinity variant of 1G4 TCR beta chain
      variable domain AA sequence

<400> SEQUENCE: 121

Met Gly Val Thr Gln Thr Pro Lys Phe Gln Val Leu Lys Thr Gly Gln
1               5                   10                  15

```
Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Arg Gly Glu Val Pro Asn Gly Tyr Asn
65              50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Tyr Val Gly
                85                  90                  95

Asn Thr Gly Glu Leu Phe Phe Gly Glu Gly Ser Arg Leu Thr Val Leu
            100                 105                 110
```

<210> SEQ ID NO 122
<211> LENGTH: 162
<212> TYPE: PRT
<213> ORGANISM: Artificial Sequence
<220> FEATURE:
<223> OTHER INFORMATION: C58c61 alpha with truncated TRAC

<400> SEQUENCE: 122

```
Met Lys Gln Glu Val Thr Gln Ile Pro Ala Ala Leu Ser Val Pro Glu
1               5                   10                  15

Gly Glu Asn Leu Val Leu Asn Cys Ser Phe Thr Asp Ser Ala Ile Tyr
            20                  25                  30

Asn Leu Gln Trp Phe Arg Gln Asp Pro Gly Lys Gly Leu Thr Ser Leu
        35                  40                  45

Leu Leu Ile Thr Pro Trp Gln Arg Glu Gln Thr Ser Gly Arg Leu Asn
    50                  55                  60

Ala Ser Leu Asp Lys Ser Ser Gly Arg Ser Thr Leu Tyr Ile Ala Ala
65                  70                  75                  80

Ser Gln Pro Gly Asp Ser Ala Thr Tyr Leu Cys Ala Val Arg Pro Leu
                85                  90                  95

Leu Asp Gly Thr Tyr Ile Pro Thr Phe Gly Arg Gly Thr Ser Leu Ile
            100                 105                 110

Val His Pro Tyr Ile Gln Asn Pro Asp Pro Ala Val Tyr Gln Leu Arg
        115                 120                 125

Asp Ser Lys Ser Ser Asp Lys Ser Val Cys Leu Phe Thr Asp Phe Asp
    130                 135                 140

Ser Gln Thr Asn Val Ser Gln Ser Lys Asp Ser Asp Val Tyr Ile Thr
145                 150                 155                 160

Asp Lys
```

<210> SEQ ID NO 123
<211> LENGTH: 170
<212> TYPE: PRT
<213> ORGANISM: Artificial Sequence
<220> FEATURE:
<223> OTHER INFORMATION: C58c61 beta with truncated TRBC1

<400> SEQUENCE: 123

```
Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45
```

```
Tyr Ser Val Ala Ile Gln Thr Thr Asp Gln Gly Glu Val Pro Asn Gly
    50                  55                  60

Tyr Asn Val Ser Arg Ser Thr Ile Glu Asp Phe Pro Leu Arg Leu Leu
65                  70                  75                  80

Ser Ala Ala Pro Ser Gln Thr Ser Val Tyr Phe Cys Ala Ser Ser Tyr
                85                  90                  95

Leu Gly Asn Thr Gly Glu Leu Phe Phe Gly Glu Gly Ser Arg Leu Thr
                100                 105                 110

Val Leu Glu Asp Leu Asn Lys Val Phe Pro Pro Glu Val Ala Val Phe
            115                 120                 125

Glu Pro Ser Glu Ala Glu Ile Ser His Thr Gln Lys Ala Thr Leu Val
    130                 135                 140

Cys Leu Ala Thr Gly Phe Phe Pro Asp His Val Glu Leu Ser Trp Trp
145                 150                 155                 160

Val Asn Gly Lys Glu Val His Ser Gly Val
                165                 170

<210> SEQ ID NO 124
<211> LENGTH: 170
<212> TYPE: PRT
<213> ORGANISM: Artificial Sequence
<220> FEATURE:
<223> OTHER INFORMATION: C58c61 beta with truncated TRBC2

<400> SEQUENCE: 124

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
                20                  25                  30

Met Ser Trp Tyr Arg Gln Asp Pro Gly Met Gly Leu Arg Leu Ile His
            35                  40                  45

Tyr Ser Val Ala Ile Gln Thr Thr Asp Gln Gly Glu Val Pro Asn Gly
    50                  55                  60

Tyr Asn Val Ser Arg Ser Thr Ile Glu Asp Phe Pro Leu Arg Leu Leu
65                  70                  75                  80

Ser Ala Ala Pro Ser Gln Thr Ser Val Tyr Phe Cys Ala Ser Ser Tyr
                85                  90                  95

Leu Gly Asn Thr Gly Glu Leu Phe Phe Gly Glu Gly Ser Arg Leu Thr
                100                 105                 110

Val Leu Glu Asp Leu Lys Asn Val Phe Pro Pro Glu Val Ala Val Phe
            115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val
                165                 170

<210> SEQ ID NO 125
<211> LENGTH: 305
<212> TYPE: PRT
<213> ORGANISM: Artificial Sequence
<220> FEATURE:
```

<223> OTHER INFORMATION: C58c61 beta with truncated TRBC2 fused to wt human IL-2

<400> SEQUENCE: 125

```
Met Asn Ala Gly Val Thr Gln Thr Pro Lys Phe Gln Val Leu Lys Thr
1               5                   10                  15
Gly Gln Ser Met Thr Leu Gln Cys Ala Gln Asp Met Asn His Glu Tyr
            20                  25                  30
Met Ser Trp Tyr Arg Gln Asp Pro Gly Met Gly Leu Arg Leu Ile His
        35                  40                  45
Tyr Ser Val Ala Ile Gln Thr Thr Asp Gln Gly Glu Val Pro Asn Gly
    50                  55                  60
Tyr Asn Val Ser Arg Ser Thr Ile Glu Asp Phe Pro Leu Arg Leu Leu
65                  70                  75                  80
Ser Ala Ala Pro Ser Gln Thr Ser Val Tyr Phe Cys Ala Ser Ser Tyr
                85                  90                  95
Leu Gly Asn Thr Gly Glu Leu Phe Phe Gly Glu Gly Ser Arg Leu Thr
            100                 105                 110
Val Leu Glu Asp Leu Lys Asn Val Phe Pro Pro Glu Val Ala Val Phe
        115                 120                 125
Glu Pro Ser Glu Ala Glu Ile Ser His Thr Gln Lys Ala Thr Leu Val
    130                 135                 140
Cys Leu Ala Thr Gly Phe Tyr Pro Asp His Val Glu Leu Ser Trp Trp
145                 150                 155                 160
Val Asn Gly Lys Glu Val His Ser Gly Val Pro Gly Ala Pro Thr Ser
                165                 170                 175
Ser Ser Thr Lys Lys Thr Gln Leu Gln Leu Glu His Leu Leu Leu Asp
            180                 185                 190
Leu Gln Met Ile Leu Asn Gly Ile Asn Asn Tyr Lys Asn Pro Lys Leu
        195                 200                 205
Thr Arg Met Leu Thr Phe Lys Phe Tyr Met Pro Lys Lys Ala Thr Glu
    210                 215                 220
Leu Lys His Leu Gln Cys Leu Glu Glu Glu Leu Lys Pro Leu Glu Glu
225                 230                 235                 240
Val Leu Asn Leu Ala Gln Ser Lys Asn Phe His Leu Arg Pro Arg Asp
                245                 250                 255
Leu Ile Ser Asn Ile Asn Val Ile Val Leu Glu Leu Lys Gly Ser Glu
            260                 265                 270
Thr Thr Phe Met Cys Glu Tyr Ala Asp Glu Thr Ala Thr Ile Val Glu
        275                 280                 285
Phe Leu Asn Arg Trp Ile Thr Phe Cys Gln Ser Ile Ile Ser Thr Leu
    290                 295                 300
Thr
305
```

<210> SEQ ID NO 126
<211> LENGTH: 9
<212> TYPE: PRT
<213> ORGANISM: Artificial Sequence
<220> FEATURE:
<223> OTHER INFORMATION: NY-ESO peptide

<400> SEQUENCE: 126

```
Ser Leu Leu Met Trp Ile Thr Gln Cys
1               5
```

```
<210> SEQ ID NO 127
<211> LENGTH: 9
<212> TYPE: PRT
<213> ORGANISM: Artificial Sequence
<220> FEATURE:
<223> OTHER INFORMATION: NY-ESO analogue

<400> SEQUENCE: 127

Ser Leu Leu Met Trp Ile Thr Gln Val
1               5
```

HIGH AFFINITY NY-ESO T CELL RECEPTORS

CROSS REFERENCE TO RELATED APPLICATIONS

This application is a continuation of U.S. application Ser. No. 11/596,458, filed Oct. 28, 2008, now U.S. Pat. No. 8,143,376, which is a U.S. National Phase of PCT/GB2005/001924, filed May 18, 2005, which published as WO 2005/113595 on Dec. 1, 2005, which claims the benefit of GB Application No. 0411123.3 filed May 19, 2004 and GB Application No. 0419643.2 filed Sep. 3, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The present invention relates to T cell receptors (TCRs) having the property of binding to SLLMWITQC (SEQ ID NO:126)-HLA-A*0201 and comprising at least one TCR α chain variable domain and/or at least one TCR β chain variable domain characterized in that said TCR has a KD for the said SLLMWITQC (SEQ ID NO:126)-HLA-A*0201 complex of less than or equal to 1 μM and/or has an off-rate ($k_{off}$) for the SLLMWITQC (SEQ ID NO:126)-HLA-A*0201 complex of $1 \times 10^{-3}$ S$^{-1}$ or slower.

BACKGROUND TO THE INVENTION

The SLLMWITQC (SEQ ID NO:126) peptide is derived from the NY-ESO-1 protein that is expressed by a range of tumours (Chen et al., (1997) PNAS USA 94 1914-1918). The Class I HLA molecules of these cancerous cells present peptides from this protein, including SLLMWITQC (SEQ ID NO:126). Therefore, the SLLMWITQC (SEQ ID NO:126)-HLA-A2 complex provides a cancer marker that TCRs can target, for example for the purpose of delivering cytotoxic or immuno-stimulatory agents to the cancer cells. However, for that purpose it would be desirable if the TCR had a higher affinity and/or a slower off-rate for the peptide-HLA complex than native TCRs specific for that complex.

BRIEF DESCRIPTION OF THE INVENTION

This invention makes available for the first time TCRs having high affinity ($K_D$) of the interaction less than or equal to 1 μM, and/or a slower off-rate ($k_{off}$) of $1 \times 10^{-3}$ S$^{-1}$ or slower, for the SLLMWITQC (SEQ ID NO:126)-HLA-A*0201 complex. Such TCRs are useful, either alone or associated with a therapeutic agent, for targeting cancer cells presenting that complex.

DETAILED DESCRIPTION OF THE INVENTION

The present invention provides a T-cell receptor (TCR) having the property of binding to SLLMWITQC (SEQ ID NO:126)-HLA-A*0201 and comprising at least one TCR α chain variable domain and/or at least one TCR β chain variable domain characterized in that said TCR has a $K_D$ for the said SLLMWITQC (SEQ ID NO:126)-HLA-A*0201 complex of less than or equal to 1 μM and/or has an off-rate ($k_{off}$) for the SLLMWITQC (SEQ ID NO:126)-HLA-A*0201 complex of $1 \times 10^{-3}$ S$^{-1}$ or slower. The $K_D$ and/or ($k_{off}$) measurement can be made by any of the known methods. A preferred method is the Surface Plasmon Resonance (Biacore) method of Example 5.

For comparison, the interaction of a disulfide-linked soluble variant of the native 1G4 TCR (see SEQ ID NO: 9 for TCR α chain and SEQ ID NO: 10 for TCR β chain) and the SLLMWITQC (SEQ ID NO:126)-HLA-A*0201 complex has a $K_D$ of approximately 10 μM, an off-rate ($k_{off}$) of $1.28 \times 10^{-1}$ S$^{-1}$ and a half-life of 0.17 minutes as measured by the Biacore-base method of Example 5.

The native 1G4 TCR specific for the SLLMWITQC (SEQ ID NO:126)-HLA-A*0201 complex has the following Valpha chain and Vbeta chain gene usage:

Alpha chain—TRAV21
Beta chain:—TRBV 6.5

The native 1G4 TCR can be used as a template into which various mutations that impart high affinity and/or a slow off-rate for the interaction between TCRs of the invention and the SLLMWITQC (SEQ ID NO:126)-HLA-A*0201 complex can be introduced. Thus the invention includes TCRs which are mutated relative to the native 1G4 TCR α chain variable domain (see FIG. 1a and SEQ ID No: 1) and/or β chain variable domain (see FIG. 1b and SEQ ID NO: 2) in at least one complementarity determining region (CDR) and/or variable domain framework region thereof. It is also contemplated that other hypervariable regions in the variable domains of the TCRs of the invention, such as the hypervariable 4 (HV4) regions, may be mutated so as to produce a high affinity mutant.

Native TCRs exist in heterodimeric αβ or γδ forms. However, recombinant TCRs consisting of a single TCR α or TCR β chain have previously been shown to bind to peptide MHC molecules.

In one embodiment the TCR of the invention comprise both an α chain variable domain and an TCR β chain variable domain.

As will be obvious to those skilled in the art the mutation(s) in the TCR α chain sequence and/or TCR β chain sequence may be one or more of substitution(s), deletion(s) or insertion(s). These mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see (Sambrook & Russell, (2001) Molecular Cloning—A Laboratory Manual (3$^{rd}$ Ed.) CSHL Press) Further information on LIC procedures can be found in (Rashtchian, (1995) Curr Opin Biotechnol 6 (1): 30-6)

It should be noted that any αβ TCR that comprises similar Valpha and Vbeta gene usage and therefore amino acid sequence to that of the 1G4 TCR could make a convenient template TCR. It would then be possible to introduce into the DNA encoding one or both of the variable domains of the template αβ TCR the changes required to produce the mutated high affinity TCRs of the invention. As will be obvious to those skilled in the art, the necessary mutations could be introduced by a number of methods, for example site-directed mutagenesis.

The TCRs of the invention include those in which one or more of the TCR alpha chain variable domain amino acids corresponding to those listed below are mutated relative to the amino acid occurring at these positions in the sequence provided for the native 1G4 TCR alpha chain variable domain in FIG. 1a and SEQ ID No: 1.

Unless stated to the contrary, the TCR amino acid sequences herein are generally provided including an N-terminal methionine (Met or M) residue. As will be known to those skilled in the art this residue may be removed during the production of recombinant proteins. Furthermore, unless stated to the contrary, the soluble TCR and TCR variable domain sequences have been truncated at the N-terminus thereof. (Resulting in the lose of the N-terminal "K" and "NA" in the TCR alpha and beta chain sequences respectively). As will be obvious to those skilled in the art these "missing" N-terminal TCR residues may be re-introduced into the TCRs of the present invention. As will also be obvious to those skilled in the art, it may be possible to truncate the sequences provided at the C-terminus and/or N-terminus thereof, by 1, 2, 3, 4, 5 or more residues, without substantially affecting the pMHC binding characteristics of the TCR, all such trivial variants are encompassed by the present invention.

As used herein the term "variable domain" is understood to encompass all amino acids of a given TCR which are not included within the constant domain as encoded by the TRAC gene for TCR α chains and either the TRBC1 or TRBC2 for TCR β chains (T cell receptor Factsbook, (2001) LeFranc and LeFranc, Academic Press, ISBN 0-12-441352-8)

As is known to those skilled in the art, part of the diversity of the TCR repertoire is due to variations which occur in the amino acid encoded by the codon at the boundary between the variable domain, as defined herein, and the constant domain. For example, the codon that is present at this boundary in the wild-type IG4 TCR sequence results in the presence of the Tyrosine (Y) residue at the C-terminal of the variable domain sequences herein. This Tyrosine replaces the N-terminal Asparagine (N) residue encoded by the TRAC gene shown in FIG. 8A.

Embodiments of the invention include mutated TCRs which comprise mutation of one or more of alpha chain variable domain amino acids corresponding to: 20V, 51Q, 52S, 53S, 94P, 95T, 96S, 97G, 98G, 99S, 100Y, 101I and 103T, for example the amino acids:

20A
51P/S/T or M
52P/F or G
53W/H or T
94H or A
95L/M/A/Q/Y/E/I/F/V/N/G/S/D or R
96L/T/Y/I/Q/V/E/X/A/W/R/G/H/D or K
97D/N/V/S/T or A
98P/H/S/T/W or A
99T/Y/D/H/V/N/E/G/Q/K/A/I or R
100F/M or D
101P/T/ or M
103A

The numbering used above is the same as that shown in FIG. 1a and SEQ ID No: 1.

Embodiments of the invention also include TCRs which comprise mutation of one or more of the TCR beta chain variable domain amino acids corresponding to those listed below, are relative to the amino acid occurring at these positions in the sequence provided for the native 1G4 TCR alpha chain variable domain of the native 1G4 TCR beta chain in FIG. 1b and SEQ ID No: 2. The amino acids referred to which may be mutated are: 18M, 50G, 51A, 52G, 53I, 55D, 56Q, 70T, 94Y, 95V and 97N, for example:

18V
50S or A
51V or I
52Q
53T or M
55R
56R
70I
94N or F
95L
97G or D

The numbering used above is the same as that shown in FIG. 1b and SEQ ID No: 2

Further preferred embodiments of the invention are provided by TCRs comprising one of the mutated alpha chain variable domain amino acid sequences shown in FIG. 6 (SEQ ID Nos: 11 to 83). Phenotypically silent variants of such TCRs also form part of this invention.

Additional preferred embodiments of the invention are provided by TCRs comprising one of the mutated beta chain variable domain amino acid sequences shown in FIG. 7 or 13. (SEQ ID Nos: 84 to 99 or 117 to 121). Phenotypically silent variants of such TCRs also form part of this invention.

Native TCRs exist in heterodimeric αβ or γδ forms. However, recombinant TCRs consisting of αα or ββ homodimers have previously been shown to bind to peptide MHC molecules. Therefore, one embodiment of the invention is provided by TCR αα or TCR ββ homodimers.

Further preferred embodiments are provided by TCRs of the invention comprising the alpha chain variable domain amino acid sequence and the beta chain variable domain amino acid sequence combinations listed below, phenotypically silent variants of such TCRs also form part of this invention:

| Alpha chain variable domain sequence, SEQ ID NO: | Beta chain variable domain sequence, SEQ ID NO: |
|---|---|
| 1 | 84 |
| 1 | 85 |
| 1 | 86 |
| 1 | 87 |
| 1 | 88 |
| 11 | 84 |
| 12 | 84 |
| 12 | 85 |
| 12 | 90 |
| 11 | 85 |
| 11 | 86 |
| 11 | 92 |
| 11 | 93 |
| 13 | 86 |
| 14 | 84 |
| 14 | 85 |
| 15 | 84 |
| 15 | 85 |
| 16 | 84 |
| 16 | 85 |
| 17 | 86 |
| 18 | 86 |
| 19 | 84 |
| 20 | 86 |
| 21 | 84 |
| 21 | 85 |
| 22 | 84 |
| 23 | 86 |
| 24 | 84 |
| 25 | 84 |
| 26 | 84 |

| Alpha chain variable domain sequence, SEQ ID NO: | Beta chain variable domain sequence, SEQ ID NO: |
|---|---|
| 27 | 84 |
| 28 | 84 |
| 29 | 84 |
| 30 | 84 |
| 31 | 84 |
| 32 | 84 |
| 33 | 84 |
| 20 | 86 |
| 34 | 86 |
| 35 | 89 |
| 36 | 89 |
| 37 | 89 |
| 38 | 89 |
| 39 | 89 |
| 16 | 89 |
| 17 | 89 |
| 31 | 89 |
| 40 | 89 |
| 1 | 90 |
| 1 | 91 |
| 41 | 90 |
| 42 | 2 |
| 42 | 85 |
| 42 | 92 |
| 1 | 92 |
| 1 | 93 |
| 43 | 92 |
| 44 | 92 |
| 45 | 92 |
| 46 | 92 |
| 47 | 92 |
| 48 | 84 |
| 49 | 94 |
| 50 | 84 |
| 50 | 94 |
| 51 | 94 |
| 51 | 95 |
| 1 | 94 |
| 1 | 85 |
| 51 | 84 |
| 52 | 84 |
| 52 | 94 |
| 52 | 95 |
| 53 | 84 |
| 49 | 95 |
| 49 | 94 |
| 54 | 92 |
| 55 | 92 |
| 56 | 92 |
| 57 | 92 |
| 58 | 92 |
| 59 | 92 |
| 60 | 92 |
| 61 | 92 |
| 62 | 92 |
| 63 | 92 |
| 64 | 92 |
| 65 | 92 |
| 66 | 92 |
| 67 | 92 |
| 68 | 92 |
| 69 | 92 |
| 70 | 92 |
| 71 | 92 |
| 72 | 92 |
| 73 | 92 |
| 74 | 92 |
| 75 | 92 |
| 76 | 92 |
| 77 | 92 |
| 78 | 92 |
| 79 | 92 |
| 80 | 92 |
| 81 | 92 |
| 82 | 92 |
| 83 | 92 |
| 11 | 96 |
| 11 | 97 |
| 11 | 98 |
| 11 | 99 |
| 1 | 89 |
| 50 | 117 |
| 49 | 117 |
| 50 | 118 |
| 49 | 119 |
| 50 | 119 |
| 58 | 93 |
| 49 | 118 |
| 1 | 119 |
| 1 | 117 |
| 55 | 120 |
| 56 | 120 |
| 50 | 121 |
| 50 | 120 |
| 49 | 121 |
| 49 | 120 |
| 48 | 118 |
| 53 | 95 |

Preferred embodiments provide a TCR of the invention comprising:

the alpha chain variable domain shown in the SEQ ID NO: 49 and the beta chain variable domain shown in the SEQ ID NO: 94, or phenotypically silent variants thereof.

In another preferred embodiment TCRs of the invention comprising the variable domain combinations detailed above further comprise the alpha chain constant region amino acid sequence shown in FIG. 8a (SEQ ID NO: 100) and one of the beta chain amino acid constant region sequences shown in FIGS. 8b and 8c (SEQ ID NOs: 101 and 102) or phenotypically silent variants thereof.

As used herein the term "phenotypically silent variants" is understood to refer to those TCRs which have a $K_D$ for the said SLLMWITQC (SEQ ID NO:126)-HLA-A*0201 complex of less than or equal to 1 μM and/or have an off-rate ($k_{off}$) of $1 \times 10^{-3}$ $S^{-1}$ or slower. For example, as is known to those skilled in the art, it may be possible to produce TCRs that incorporate minor changes in the constant and/or variable domains thereof compared to those detailed above without altering the affinity and/or off-rate for the interaction with the SLLMWITQC (SEQ ID NO:126)-HLA-A*0201 complex. Such trivial variants are included in the scope of this invention. Those TCRs in which one or more conservative substitutions have been made also form part of this invention.

In one broad aspect, the TCRs of the invention are in the form of either single chain TCRs (scTCRs) or dimeric TCRs (dTCRs) as described in WO 04/033685 and WO 03/020763.

A suitable scTCR form comprises a first segment constituted by an amino acid sequence corresponding to a TCR α chain variable domain, a second segment constituted by an amino acid sequence corresponding to a TCR β chain variable domain sequence fused to the N terminus of an amino acid sequence corresponding to a TCR β chain constant domain extracellular sequence, and a linker sequence linking the C terminus of the first segment to the N terminus of the second segment.

Alternatively the first segment may be constituted by an amino acid sequence corresponding to a TCR β chain variable domain, the second segment may be constituted by an amino acid sequence corresponding to a TCR α chain variable domain sequence fused to the N terminus of an amino acid sequence corresponding to a TCR α chain constant domain extracellular sequence The above scTCRs may further comprise a disulfide bond between the first and second chains, said disulfide bond being one which has no equivalent in native αβ T cell receptors, and wherein the length of the linker sequence and the position of the disulfide bond being such that the variable domain sequences of the first and second segments are mutually orientated substantially as in native αβ T cell receptors.

More specifically the first segment may be constituted by an amino acid sequence corresponding to a TCR α chain variable domain sequence fused to the N terminus of an amino acid sequence corresponding to a TCR α chain constant domain extracellular sequence, the second segment may be constituted by an amino acid sequence corresponding to a TCR β chain variable domain fused to the N terminus of an amino acid sequence corresponding to TCR β chain constant domain extracellular sequence, and a disulfide bond may be provided between the first and second chains, said disulfide bond being one which has no equivalent in native αβ T cell receptors.

In the above scTCR forms, the linker sequence may link the C terminus of the first segment to the N terminus of the second segment, and may have the formula -PGGG-(SGGGG)$_n$-P- wherein n is 5 or 6 and P is proline, G is glycine and S is serine.

(SEQ ID NO: 103)
-PGGG-SGGGGSGGGGSGGGGSGGGGSGGGG-P (SEQ ID NO: 104)
-PGGG-SGGGGSGGGGSGGGGSGGGGSGGGGSGGGG-P

A suitable dTCR form of the TCRs of the present invention comprises a first polypeptide wherein a sequence corresponding to a TCR α chain variable domain sequence is fused to the N terminus of a sequence corresponding to a TCR α chain constant domain extracellular sequence, and a second polypeptide wherein a sequence corresponding to a TCR β chain variable domain sequence fused to the N terminus a sequence corresponding to a TCR β chain constant domain extracellular sequence, the first and second polypeptides being linked by a disulfide bond which has no equivalent in native αβ T cell receptors.

The first polypeptide may comprise a TCR α chain variable domain sequence is fused to the N terminus of a sequence corresponding to a TCR α chain constant domain extracellular sequence, and a second polypeptide wherein a sequence corresponding to a TCR β chain variable domain sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof. ("TRAC" etc. nomenclature herein as per T cell receptor Factsbook, (2001) LeFranc and LeFranc, Academic Press, ISBN 0-12-441352-8)

The dTCR or scTCR form of the TCRs of the invention may have amino acid sequences corresponding to human αβ TCR extracellular constant and variable domain sequences, and a disulfide bond may link amino acid residues of the said constant domain sequences, which disulfide bond has no equivalent in native TCRs. The disulfide bond is between cysteine residues corresponding to amino acid residues whose β carbon atoms are less than 0.6 nm apart in native TCRs, for example between cysteine residues substituted for Thr 48 of exon 1 of TRAC*01 and Ser 57 of exon 1 of TRBC1*01 or TRBC2*01 or the non-human equivalent thereof. Other sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

In addition to the non-native disulfide bond referred to above, the dTCR or scTCR form of the TCRs of the invention may include a disulfide bond between residues corresponding to those linked by a disulfide bond in native TCRs.

The dTCR or scTCR form of the TCRs of the invention preferably does not contain a sequence corresponding to transmembrane or cytoplasmic sequences of native TCRs.

Preferred embodiments of the invention provide a soluble TCR consisting of:

the alpha chain amino acid sequence of SEQ ID NO: 122 and beta chain amino acid sequence SEQ ID NO: 123:

the alpha chain amino acid sequence of SEQ ID NO: 122 and beta chain amino acid sequence SEQ ID NO: 124;

SEQ ID NOs: 122, 123 and 124 have been provided in a form which includes the N-terminal methionine (M) and the N-terminal "K" and "NA" in the TCR alpha and beta chain sequences respectively.

PEGylated TCR Monomers

In one particular embodiment a TCR of the invention is associated with at least one polyalkylene glycol chain(s). This association may be cause in a number of ways known to those skilled in the art. In a preferred embodiment the polyalkylene chain(s) is/are covalently linked to the TCR. In a further embodiment the polyethylene glycol chains of the present aspect of the invention comprise at least two polyethylene repeating units.

Multivalent TCR Complexes

One aspect of the invention provides a multivalent TCR complex comprising at least two TCRs of the invention. In one embodiment of this aspect, at least two TCR molecules are linked via linker moieties to form multivalent complexes. Preferably the complexes are water soluble, so the linker moiety should be selected accordingly. Furthermore, it is preferable that the linker moiety should be capable of attachment to defined positions on the TCR molecules, so that the structural diversity of the complexes formed is minimised. One embodiment of the present aspect is provided by a TCR complex of the invention wherein the polymer chain or peptidic linker sequence extends between amino acid residues of each TCR which are not located in a variable region sequence of the TCR.

Since the complexes of the invention may be for use in medicine, the linker moieties should be chosen with due regard to their pharmaceutical suitability, for example their immunogenicity.

Examples of linker moieties which fulfil the above desirable criteria are known in the art, for example the art of linking antibody fragments.

There are two classes of linker that are preferred for use in the production of multivalent TCR molecules of the present invention. A TCR complex of the invention in which the TCRs are linked by a polyalkylene glycol chain provides one embodiment of the present aspect.

The first are hydrophilic polymers such as polyalkylene glycols. The most commonly used of this class are based on polyethylene glycol or PEG, the structure of which is shown below.

$HOCH_2CH_2O(CH_2CH_2O)_n\text{—}CH_2CH_2OH$

Wherein n is greater than two. However, others are based on other suitable, optionally substituted, polyalkylene glycols include polypropylene glycol, and copolymers of ethylene glycol and propylene glycol.

Such polymers may be used to treat or conjugate therapeutic agents, particularly polypeptide or protein therapeutics, to achieve beneficial changes to the PK profile of the therapeutic, for example reduced renal clearance, improved plasma half-life, reduced immunogenicity, and improved solubility. Such improvements in the PK profile of the PEG-therapeutic conjugate are believe to result from the PEG molecule or molecules forming a 'shell' around the therapeutic which sterically hinders the reaction with the immune system and reduces proteolytic degradation. (Casey et al, (2000) Tumor Targetting 4 235-244) The size of the hydrophilic polymer used my in particular be selected on the basis of the intended therapeutic use of the TCR complex. Thus for example, where the product is intended to leave the circulation and penetrate tissue, for example for use in the treatment of a tumour, it may be advantageous to use low molecular weight polymers in the order of 5 KDa. There are numerous review papers and books that detail the use of PEG and similar molecules in pharmaceutical formulations. For example, see Harris (1992) Polyethylene Glycol Chemistry—Biotechnical and Biomedical Applications, Plenum, New York, N.Y. or Harris & Zalipsky (1997) Chemistry and Biological Applications of Polyethylene Glycol ACS Books, Washington, D.C.

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the TCR. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable, chain, Such spacers include, by are not limited to the following:

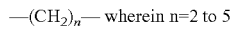
—$(CH_2)_n$— wherein n=2 to 5

—$(CH_2)_3NHCO(CH_2)_2$

A TCR complex of the invention in which a divalent alkylene spacer radical is located between the polyalkylene glycol chain and its point of attachment to a TCR of the complex provides a further embodiment of the present aspect.

A TCR complex of the invention in which the polyalkylene glycol chain comprises at least two polyethylene glycol repeating units provides a further embodiment of the present aspect.

There are a number of commercial suppliers of hydrophilic polymers linked, directly or via a spacer, to reactive chemistries that may be of use in the present invention. These suppliers include Nektar Therapeutics (CA, USA), NOF Corporation (Japan), Sunbio (South Korea) and Enzon Pharmaceuticals (NJ, USA).

Commercially available hydrophilic polymers linked, directly or via a spacer, to reactive chemistries that may be of use in the present invention include, but are not limited to, the following:

| PEG linker Description | Source of PEG | Catalogue Number |
|---|---|---|
| TCR Monomer attachment | | |
| 5K linear (Maleimide) | Nektar | 2D2MOHO1 |
| 20K linear (Maleimide) | Nektar | 2D2MOPO1 |
| 20K linear (Maleimide) | NOF Corporation | SUNBRIGHT ME-200MA |
| 20K branched (Maleimide) | NOF Corporation | SUNBRIGHT GL2-200MA |
| 30K linear (Maleimide) | NOF Corporation | SUNBRIGHT ME-300MA |
| 40K branched PEG (Maleimide) | Nektar | 2D3XOTO1 |
| 5K-NP linear (for Lys attachment) | NOF Corporation | SUNBRIGHT MENP-50H |
| 10K-NP linear (for Lys attachment) | NOF Corporation | SUNBRIGHT MENP-10T |
| 20K-NP linear (for Lys attachment) | NOF Corporation | SUNBRIGHT MENP-20T |
| TCR dimer linkers | | |
| 3.4K linear (Maleimide) | Nektar | 2D2DOFO2 |
| 5K forked (Maleimide) | Nektar | 2D2DOHOF |
| 10K linear (with orthopyridyl ds-linkers in place of Maleimide) | Sunbio | |
| 20K forked (Maleimide) | Nektar | 2D2DOPOF |
| 20K linear (Maleimide) | NOF Corporation | |
| 40K forked (Maleimide) | Nektar | 2D3XOTOF |
| Higher order TCR multimers | | |
| 15K, 3 arms, $Mal_3$ (for trimer) | Nektar | OJOONO3 |
| 20K, 4 arms, $Mal_4$ (for tetramer) | Nektar | OJOOPO4 |
| 40K, 8 arms, $Mal_8$ (for octamer) | Nektar | OJOOTO8 |

A wide variety of coupling chemistries can be used to couple polymer molecules to protein and peptide therapeutics. The choice of the most appropriate coupling chemistry is largely dependant on the desired coupling site. For example, the following coupling chemistries have been used attached to one or more of the termini of PEG molecules (Source: Nektar Molecular Engineering Catalogue 2003):

N-maleimide
Vinyl sulfone
Benzotriazole carbonate
Succinimidyl proprionate
Succinimidyl butanoate
Thio-ester
Acetaldehydes
Acrylates
Biotin
Primary amines As stated above non-PEG based polymers also provide suitable linkers for multimerising the TCRs of the present invention. For example, moieties containing maleimide termini linked by aliphatic chains such as BMH and BMOE (Pierce, products Nos. 22330 and 22323) can be used.

Peptidic linkers are the other class of TCR linkers. These linkers are comprised of chains of amino acids, and function to produce simple linkers or multimerisation domains onto which TCR molecules can be attached. The biotin/streptavidin system has previously been used to produce TCR tetramers (see WO/99/60119) for in-vitro binding studies. However, stepavidin is a microbially-derived polypeptide and as such not ideally suited to use in a therapeutic.

A TCR complex of the invention in which the TCRs are linked by a peptidic linker derived from a human multimerisation domain provides a further embodiment of the present aspect.

There are a number of human proteins that contain a multimerisation domain that could be used in the production of multivalent TCR complexes. For example the tetramerisation domain of p53 which has been utilised to produce tetramers of scFv antibody fragments which exhibited increased serum persistence and significantly reduced off-rate compared to the monomeric scFV fragment. (Willuda et al. (2001) J. Biol. Chem. 276 (17) 14385-14392) Haemoglobin also has a tetramerisation domain that could potentially be used for this kind of application.

A multivalent TCR complex of the invention comprising at least two TCRs provides a final embodiment of this aspect, wherein at least one of said TCRs is associated with a therapeutic agent.

In one aspect a TCR (or multivalent complex thereof) of the present invention may alternatively or additionally comprise a reactive cysteine at the C-terminal or N-terminal of the alpha or beta chains thereof.

Diagnostic and Therapeutic Use

In one aspect the TCR of the invention may be associated with a therapeutic agent or detectable moiety. For example, said therapeutic agent or detectable moiety may be covalently linked to the TCR.

In one embodiment of the invention said therapeutic agent or detectable moiety is covalently linked to the C-terminus of one or both TCR chains.

In one aspect the scTCR or one or both of the dTCR chains of TCRs of the present invention may be labelled with an detectable moiety, for example a label that is suitable for diagnostic purposes. Such labelled TCRs are useful in a method for detecting a SLLMWITQC (SEQ ID NO:126)-HLA-A*0201 complex which method comprises contacting the TCR ligand with a TCR (or a multimeric high affinity TCR complex) which is specific for the TCR ligand; and detecting binding to the TCR ligand. In tetrameric TCR complexes formed for example, using biotinylated heterodimers, fluorescent streptavidin can be used to provide a detectable label. Such a fluorescently-labelled TCR tetramer is suitable for use in FACS analysis, for example to detect antigen presenting cells carrying the SLLMWITQC (SEQ ID NO:126)-HLA-A*0201 complex for which these high affinity TCRs are specific.

Another manner in which the soluble TCRs of the present invention may be detected is by the use of TCR-specific antibodies, in particular monoclonal antibodies. There are many commercially available anti-TCR antibodies, such as αF1 and βF1, which recognise the constant domains of the α and β chains, respectively.

In a further aspect a TCR (or multivalent complex thereof) of the present invention may alternatively or additionally be associated with (e.g. covalently or otherwise linked to) a therapeutic agent which may be, for example, a toxic moiety for use in cell killing, or an immune effector molecule such as an interleukin or a cytokine. A multivalent TCR complex of the invention may have enhanced binding capability for a TCR ligand compared to a non-multimeric wild-type or T cell receptor heterodimer of the invention. Thus, the multivalent TCR complexes according to the invention are particularly useful for tracking or targeting cells presenting particular antigens in vitro or in vivo, and are also useful as intermediates for the production of further multivalent TCR complexes having such uses. These TCRs or multivalent TCR complexes may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the SLLMWITQC (SEQ ID NO:126)-HLA-A*0201 complex and having the therapeutic agent associated therewith.

In particular, the soluble TCR or multivalent TCR complex of the present invention can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to TCRs or multivalent TCR complexes according to the invention specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:

small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Including but not limited to, ricin, diphtheria toxin, pseudomonas bacterial exotoxin A, DNAase and RNAase;

radio-nuclides, i.e. unstable isotopes of elements which decay with the concurrent emission of one or more of α or β particles, or γ rays. including but not limited to, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

prodrugs, including but not limited to, antibody directed enzyme pro-drugs;

immuno-stimulants, i.e. moieties which stimulate immune response. Including but not limited to, cytokines such as IL-2 and IFN, Superantigens and mutants thereof, TCR-HLA fusions and chemokines such as IL-8, platelet factor 4, melanoma growth stimulatory protein, etc, antibodies or fragments thereof, complement activators, xenogeneic protein domains, allogeneic protein domains, viral/bacterial protein domains, viral/bacterial peptides and anti-T cell determinant antibodies (e.g. anti-CD3 or anti-CD28).

Functional Antibody Fragments and Variants

Antibody fragments and variants/analogues which are suitable for use in the compositions and methods described herein include, but are not limited to, the following.

Antibody Fragments

As is known to those skilled in the art, it is possible to produce fragments of a given antibody which retain substantially the same binding characteristics as those of the parent antibody. The following provides details of such fragments:

Minibodies—These constructs consist of antibodies with a truncated Fc portion. As such they retain the complete binding domains of the antibody from which are derived.

Fab fragments—These comprise a single immunoglobulin light chain covalently-linked to part of an immunoglobulin heavy chain. As such, Fab fragments comprise a single antigen combining site. Fab fragments are defined by the portion of an IgG that can be liberated by treatment with papain. Such fragments are commonly produced via recombinant DNA techniques. (Reeves et al., (2000) *Lecture Notes on Immunology* (4th Edition) Published by Blackwell Science)

F(ab')$_2$ fragments—These comprise both antigen combining sites and the hinge region from a single antibody. F(ab')$_2$ fragments are defined by the portion of an IgG that can be liberated by treatment with pepsin. Such fragments are commonly produced via recombinant DNA techniques. (Reeves et al., (2000) *Lecture Notes on Immunology* (4th Edition) Published by Blackwell Science)

Fv fragments—These comprise an immunoglobulin variable heavy domain linked to an immunoglobulin variable light domain. A number of Fv designs have been produced. These include dsFvs, in which the association between the two domains is enhanced by an introduced disulfide bond. Alternatively, scFVs can be formed using a peptide linker to bind the two domains together as a single polypeptide. Fvs constructs containing a variable domain of a heavy or light immunoglobulin chain associated to the variable and constant domain of the corresponding immunoglobulin heavy or light chain have also been produced. FV have also been multimerised to form diabodies and triabodies (Maynard et al., (2000) *Annu Rev Biomed Eng* 2 339-376)

Nanobodies™—These constructs, marketed by Ablynx (Belgium), comprise synthetic single immunoglobulin variable heavy domain derived from a camelid (e.g. camel or llama) antibody.

Domain Antibodies—These constructs, marketed by Domantis (Belgium), comprise an affinity matured single immunoglobulin variable heavy domain or immunoglobulin variable light domain.

Antibody Variants and Analogues

The defining functional characteristic of antibodies in the context of the present invention is their ability to bind specifically to a target ligand. As is known to those skilled in the art it is possible to engineer such binding characteristics into a range of other proteins. Examples of antibody variants and analogues suitable for use in the compositions and methods of the present invention include, but are not limited to, the following.

Protein scaffold-based binding polypeptides—This family of binding constructs comprise mutated analogues of proteins which contain native binding loops. Examples include Affibodies, marketed by Affibody (Sweden), which are based on a three-helix motif derived from one of the IgG binding domains of *Staphylococcus aureus* Protein A. Another example is provided by Evibodies, marketed by EvoGenix (Australia) which are based on the extracellular domains of CTLA-4 into which domains similar to antibody binding loops are grafted. A final example, Cytokine Traps marketed by Regeneron Pharmaceuticals (US), graft cytokine receptor domains into antibody scaffolds. (Nygren et al., (2000) *Current Opinion in Structural biology* 7 463-469) provides a review of the uses of scaffolds for engineering novel binding sites in proteins. This review mentions the following proteins as sources of scaffolds: CP1 zinc finger, Tendamistat, Z domain (a protein A analogue), PST1, Coiled coils, LACI-D1 and cytochrome $b_{562}$. Other protein scaffold studies have reported the use of Fibronectin, Green fluorescent protein (GFP) and ankyrin repeats.

As is known to those skilled in the art antibodies or fragments, variants or analogues thereof can be produced which bind to various parts of a given protein ligand. For example, anti-CD3 antibodies can be raised to any of the polypeptide chains from which this complex is formed (i.e. γ, δ, ε, ζ, and η CD3 chains) Antibodies which bind to the ε CD3 chain are the preferred anti-CD3 antibodies for use in the compositions and methods of the present invention.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

It is expected that the high affinity SLLMWITQC (SEQ ID NO: 125) (SEQ ID NO:126)-HLA-A*0201 specific TCRs disclosed herein may be used in methods for the diagnosis and treatment of cancer.

For cancer treatment, the localisation in the vicinity of tumours or metastasis would enhance the effect of toxins or immunostimulants. For vaccine delivery, the vaccine antigen could be localised in the vicinity of antigen presenting cells, thus enhancing the efficacy of the antigen. The method can also be applied for imaging purposes.

One embodiment is provided by an isolated cell presenting a TCR of the invention. For example, said cell may be a T cell.

Further embodiments of the invention are provided by a pharmaceutical composition comprising:

a TCR or a multivalent TCR complex of the invention (optionally associated with a therapeutic agent), or a plurality of cells presenting at least one TCR of the invention, together with a pharmaceutically acceptable carrier;

The invention also provides a method of treatment of cancer comprising administering to a subject suffering such cancer disease an effective amount of a TCR or a multivalent TCR complex of the invention (optionally associated with a therapeutic agent), or a plurality of cells presenting at least one TCR of the invention. In a related embodiment the invention provides for the use of a TCR or a multivalent TCR complex of the invention (optionally associated with a therapeutic agent), or a plurality of cells presenting at least one TCR of the invention, in the preparation of a composition for the treatment of cancer.

Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by admixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Additional Aspects

A scTCR or dTCR (which preferably is constituted by constant and variable sequences corresponding to human sequences) of the present invention may be provided in substantially pure form, or as a purified or isolated preparation. For example, it may be provided in a form which is substantially free of other proteins.

The invention also provides a method of producing a high affinity TCR having the property of binding to SLLMWITQC (SEQ ID NO:126)-HLA-A*0201. characterized in that the TCR (i) comprises at least one TCR α chain variable domain and/or at least one TCR β chain variable domain and (ii) has a $K_D$ for the said SLLMWITQC (SEQ ID NO:126)-HLA-A*0201 complex of less than or equal to 1 μM and/or an off-rate ($k_{off}$) for the SLLMWITQC (SEQ ID NO:126)-HLA-A*0201 complex of $1 \times 10^{-3}$ $S^{-1}$ or slower, wherein the method comprises:

(a) the production of a TCR comprising the α and β chain variable domains of the 1G4 TCR wherein one or both of the α and β chain variable domains comprise a mutation(s) in one or more of the amino acids identified in claims 7 and 8;

(b) contacting said mutated TCR with SLLMWITQC (SEQ ID NO:126)-HLA-A*0201 under conditions suitable to allow the binding of the TCR to SLLMWITQC (SEQ ID NO:126)-HLA-A*0201;

and measuring the $K_D$ and/or $k_{off}$ of the interaction.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIGS. 1a and 1b details the alpha chain variable domain amino acid and beta chain variable domain amino acid sequences of the native 1G4 TCR respectively.

FIGS. 2a and 2b show respectively the DNA sequence of soluble versions of the native 1G4 TCR α and β chains.

FIGS. 3a and 3b show respectively the 1G4 TCR α and β chain extracellular amino acid sequences produced from the DNA sequences of FIGS. 2a and 2b.

FIGS. 4a and 4b show respectively the DNA sequence of soluble versions of the 1G4 TCR α and β chains mutated to include additional cysteine residues to form a non-native disulphide bond. The mutated codon is indicated by shading.

FIGS. 5a and 5b show respectively the 1G4 TCR α and β chain extracellular amino acid sequences produced from the DNA sequences of FIGS. 4a and 4b. The introduced cysteine is indicated by shading.

FIG. 6 details the alpha chain variable domain amino acid sequences of the high affinity 1G4 TCR variants.

FIG. 7 details the beta chain variable domain amino acid sequences of the high affinity 1G4 TCR variants.

FIG. 8a details the amino acid sequence of a soluble form of TRAC.

FIG. 8b details the amino acid sequence of a soluble form of TRBC1.

FIG. 8c details the amino acid sequence of a soluble form of TRBC2.

FIG. 9 details the DNA sequence of the pEX954 plasmid.
FIG. 10 details the DNA sequence of the pEX821 plasmid.
FIG. 11 details the DNA sequence of the pEX202 plasmid.
FIG. 12 details the DNA sequence of the pEX205 plasmid.
FIG. 13 details further beta chain variable domain amino acid sequences of the high affinity 1G4 TCR variants.

FIG. 14a details the alpha chain amino acid sequences of a preferred soluble high affinity 1G4 TCR variant.

FIG. 14b details the beta chain amino acid sequences of a preferred (c58c61) soluble high affinity 1G4 TCR variant utilising the TRBC1 constant domain.

FIG. 14c details the beta chain amino acid sequences of a preferred (c58c61) soluble high affinity 1G4 TCR variant utilising the TRBC2 constant domain.

FIG. 14d details the beta chain amino acid sequences of a preferred (c58c61) soluble high affinity 1G4 TCR using the TRBC2 encoded constant region fused via a peptide linker to wild-type human IL-2.

Figure 15A:
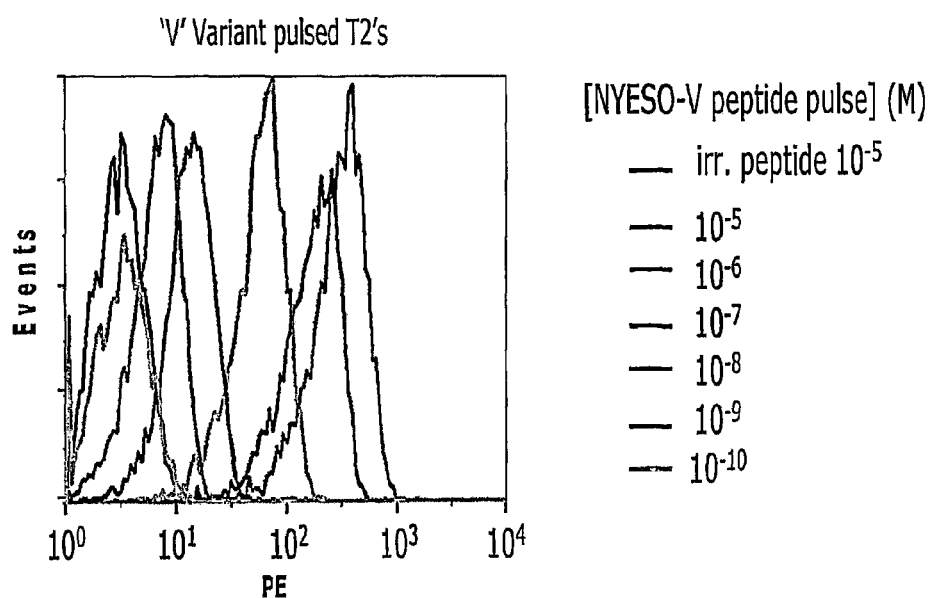

FIG. 15a shows FACs staining of T2 cell pulsed with a range of NY-ESO-analogue SLLMWITQV (SEQ ID NO:127) peptide concentrations using the high affinity c58c61 1G4 TCR-IL-2 fusion proteins.

Figure 15B:
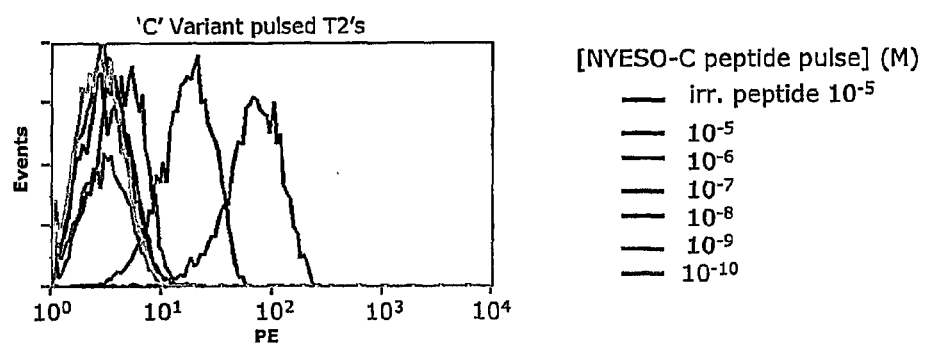

FIG. 15b shows FACs staining of T2 cell pulsed with a range of NY-ESO-derived SLLMWITQC (SEQ ID NO:126) peptide concentrations using the high affinity c58c61 1G4 TCR-IL-2 fusion proteins.

Figure 16:
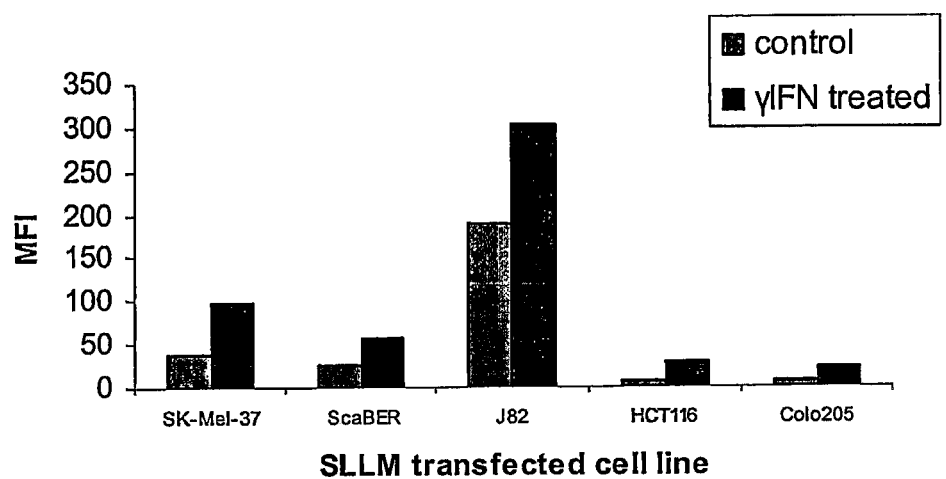

FIG. 16 shows FACs staining of SK-MEL-37, ScaBER, J82, HcT119 and Colo 205 cancer cells transfected with an SLLMWITQC (SEQ ID NO:126) peptide producing ubiquitin minigene (±proteosome inhibitors) using the high affinity c58c61 1G4 TCR-IL-2 fusion proteins.

Figure 17:
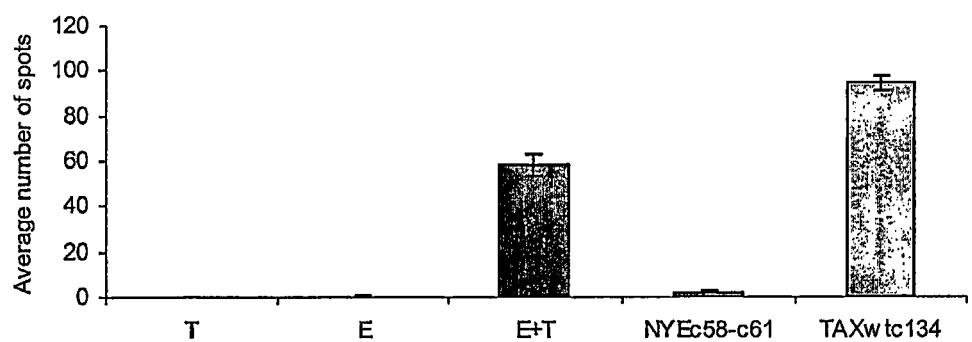

FIG. 17 shows ELISPOT data demonstrating the ability of soluble high affinity c58c61 1G4 TCR to inhibit CTL activation against the MEL-624 cancer cell.

Figure 18:
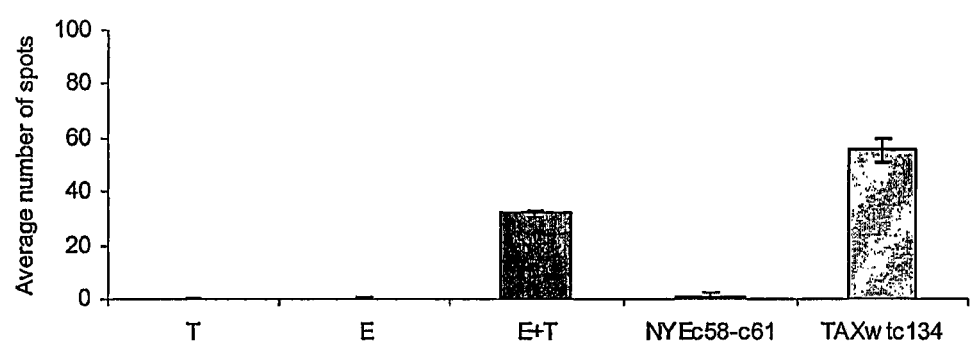

FIG. 18 shows ELISPOT data demonstrating the ability of soluble high affinity c58c61 1G4 TCR to inhibit CTL activation against the SK-MEL-37 cancer cell.

Figure 19:
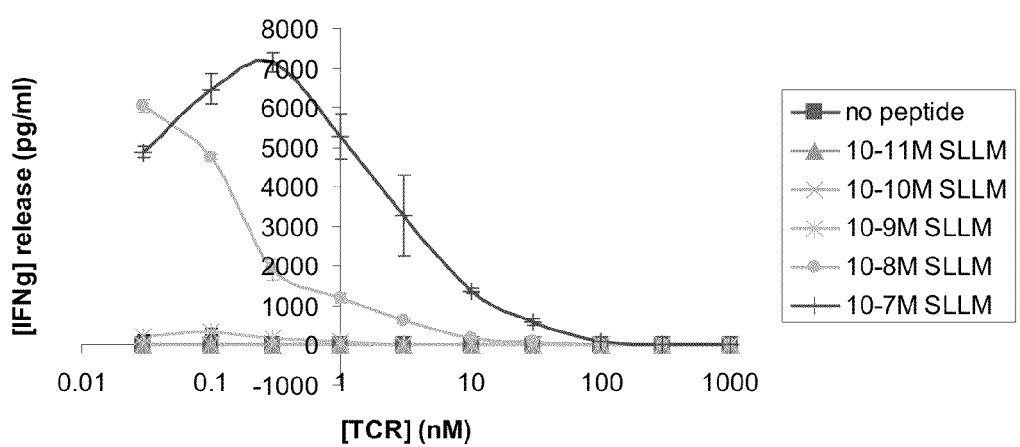

FIG. 19 shows inhibition of T cell activation against peptide pulsed T2 cells by the soluble c58c61 high affinity 1G4 TCR as measured by IFNγ production.

Figure 20:
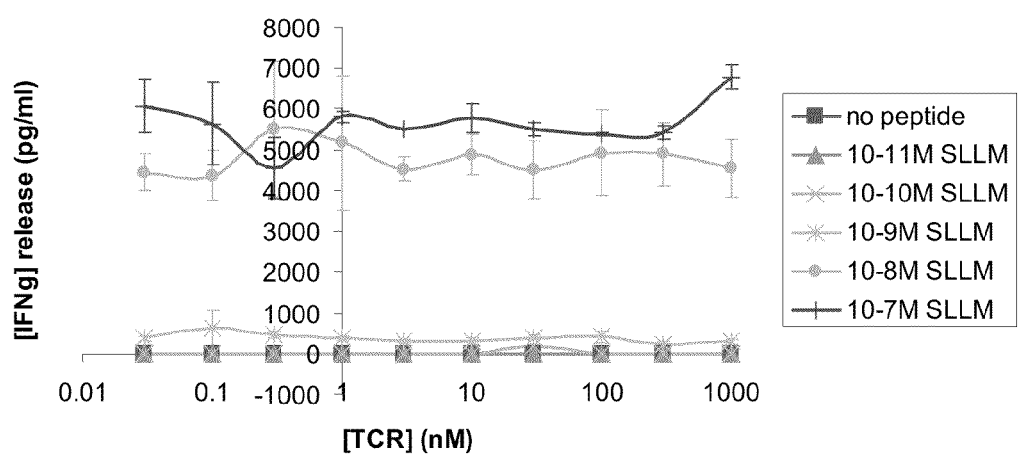

FIG. 20 shows lack of inhibition of T cell activation against peptide pulsed T2 cells by the soluble wild-type 1G4 TCR as measured by IFNγ production.

Figure 21:
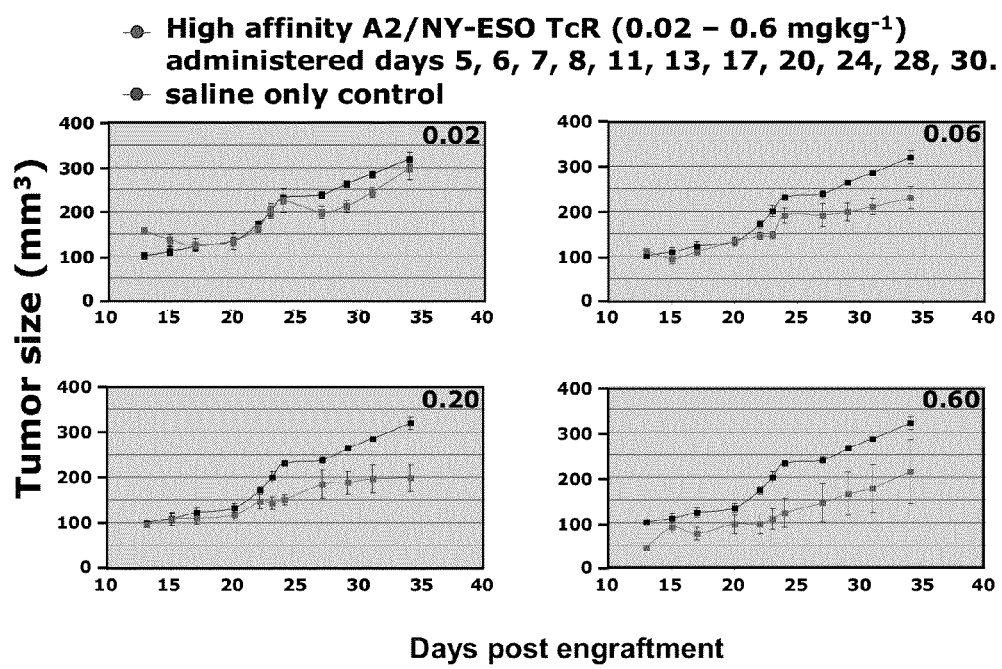

FIG. 21 shows tumor growth inhibition caused by soluble c58c61 high affinity 1G4 TCR-IL-2 immunoconjugates.

Figure 22:
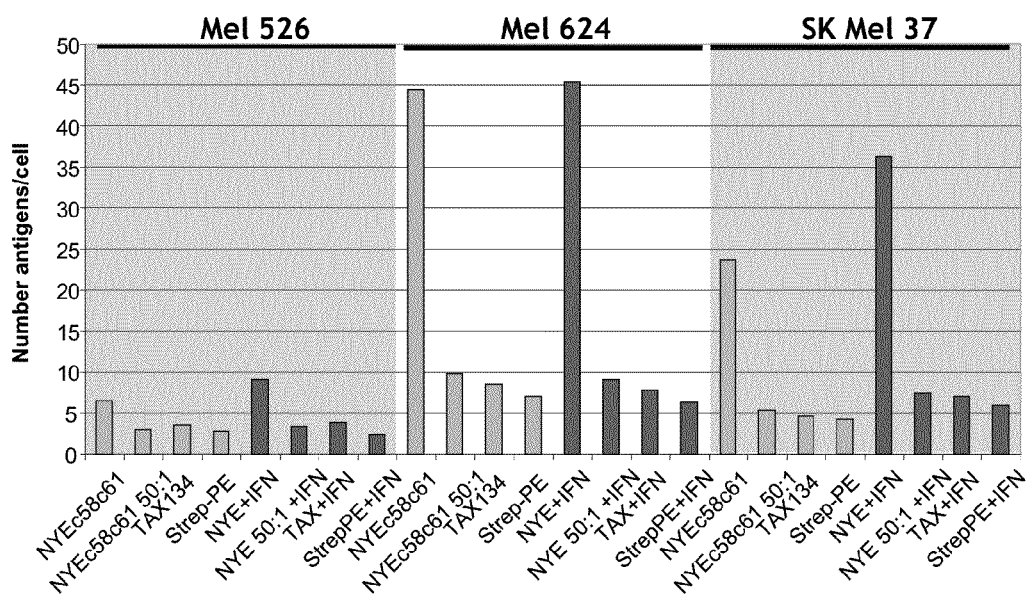

FIG. 22 shows the number of SLLMWITQC (SEQ ID NO:126)-HLA-A*0201 antigens on the surface of Mel 526, Mel 624 and SK-Mel-37 cancer cells as determined by fluorescent microscopy. The visualisation of cell-bound biotinylated soluble c58c61 high affinity 1G4 TCRs was facilitated by conjugation with streptavidin-R phycoerythrin (PE).

EXAMPLE 1

Production of a Soluble Disulfide-Linked TCR Comprising the Native 1G4 TCR Variable Domain RNA Isolation Total RNA was isolated from 10000 clonal T cells by re-suspension in 100 µl tri-reagent (Sigma) and processing of the lysate according to the manufacturer's instructions. After the final precipitation the RNA was re-dissolved in 12.5 µl RNAse free water.

cDNA Production

To the above sample of RNA, 2.5 µl of 10 mM oligo-dT$^{15}$ (Promega) was added and the sample incubated at 60° C. for 2 minutes then placed on ice. Reverse transcription was carried out using OmniscriptRT kit (Qiagen) by addition of 2 µl RT buffer (10×), 2 µl 5 mM dNTP, 1 µl Omniscript reverse transcriptase. The sample was mixed and incubated for 1 hour at 37° C. cDNA was then stored at −80° C.

The above cDNA was used as template. A panel of forward primers covering all possible alpha and beta variable chains was used to screen for, and amplify by PCR, alpha and beta chains genes. Primer sequences used for TCR chain gene amplification were designed from the NCBI website using accession numbers obtained from the T cell receptor Factsbook, (2001) LeFranc and LeFranc, Academic Press, ISBN 0-12-441352-8. Alpha-chain forward primers were designed to contain a ClaI restriction site and the universal alpha chain reverse primer a SalI restriction site. Beta-chain forward primers were designed to contain a AseI restriction site and universal beta reverse primer an AgeI restriction site.

Recipient vectors for the TCR gene fragments were based on a pGMT7 parent plasmid, which contains the T7 promoter for high level expression in *E. coli* strain BL21-DE3 (pLysS) (Pan et al., *Biotechniques* (2000) 29 (6): 1234-8)

Alpha chain purified PCR products were digested with ClaI and SalII and ligated into pEX954 (see FIG. 9) cut with ClaI and XhoI.

Beta chain purified PCR products were digested with AseI and AgeI and ligated into pEX821 (See FIG. 10) cut with NdeI/AgeI.

Ligation

The cut PCR product and cut vector were ligated using a rapid DNA ligation kit (Roche) following the manufacturers instructions.

Ligated plasmids were transformed into competent *E. coli* strain XL1-blue cells and plated out on LB/agar plates containing 100 mg/ml ampicillin. Following incubation overnight at 37° C., single colonies were picked and grown in 10 ml LB containing 100 mg/ml ampicillin overnight at 37° C. with shaking. Cloned plasmids were purified using a Miniprep kit (Qiagen) and the insert was sequenced using an automated DNA sequencer (Lark Technologies).

FIGS. 4a and 4b show respectively the DNA sequence of soluble versions of the 1G4 TCR α and β chains mutated to include additional cysteine residues to form a non-native disulphide bond.

FIGS. 5a and 5b show respectively the NY-ESO TCR α and β chain extracellular amino acid sequences produced from the DNA sequences of FIGS. 4a and 4b

EXAMPLE 2

Production of High Affinity Variants of the Soluble Disulfide Linked 1G4 TCR The soluble disulfide-linked native 1G4 TCR produced as described in Example 1 can be used a template from which to produce the TCRs of the invention which have an increased affinity for the SLLMWITQC (SEQ ID NO:126)-HLA-A*0201 complex.

The amino sequences of the mutated TCR alpha and beta chain variable domains which demonstrate high affinity for the SLLMWITQC (SEQ ID NO:126)-HLA-A*0201 complex are listed in FIGS. 6 and 7 respectively. (SEQ ID Nos: 11-83 and 84-99 respectively) As is known to those skilled in the art the necessary codon changes required to produce these mutated chains can be introduced into the DNA encoding these chains by site-directed mutagenesis. (QuickChange™ Site-Directed Mutagenesis Kit from Stratagene)

Briefly, this is achieved by using primers that incorporate the desired codon change(s) and the plasmids containing the relevant 1G4 TCR chain as a template for the mutagenesis:

Mutagenesis was carried out using the following conditions: 50 ng plasmid template, 1 µl of 10 mM dNTP, 5 µl of 10× Pfu DNA polymerase buffer as supplied by the manufacturer, 25 pmol of fwd primer, 25 pmol of rev primer, 1 µl pfu DNA polymerase in total volume 50 µl. After an initial denaturation step of 2 mins at 95 C, the reaction was subjected to 25 cycles of denaturation (95 C, 10 secs), annealing (55 C 10 secs), and elongation (72 C, 8 mins). The resulting product was digested with DpnI restriction enzyme to remove the template plasmid and transformed into *E. coli* strain XL1-blue. Mutagenesis was verified by sequencing.

EXAMPLE 3

Production of Soluble "Zippered" High Affinity TCRs

Alpha Chain—C-Jun Leucine Zipper

The construct was made by PCR stitching.

For the 5'-end of the gene the plasmid coding for the high affinity TCR alpha chains and containing the code for the introduced inter-chain di-sulfide bridge was used as template. PCR with the following two primer pairs generated the desired variable domain.

```
5'-TRAV21 fwd
                                       (SEQ ID NO: 105)
tctctcattaatgaaacaggaggtgacgcagattcct C-alpha rev
                                       (SEQ ID NO: 106)
CGGCAGGGTCAGGGTTCTGG
```

For the 3'-end of the gene the plasmid pEX202 (see FIG. 11), coding for a wild type affinity TCR alpha chain fused to human c-jun leucine zipper domain and not containing the code for the introduced inter-chain di-sulfide bridge, was used as template. PCR with the following primer pair generated the desired constant domain.

```
C-alpha fwd
                                       (SEQ ID NO: 107)
CCAGAACCCTGACCCTGCCG 3'-alpha rev
                                       (SEQ ID NO: 108)
aagcttcccgggggaactttctgggctggg
```

The two products were mixed and diluted 1000 fold and 1 µl was used as template in a 50 µl PCR with 5'-TRAV21 fwd and 3'-alpha rev primers.

The resulting PCR product was digested using restriction enzymes AseI and XmaI and ligated into pEX202 cut with NdeI and XmaI.

PCRs were carried out using the following conditions: 50 pg plasmid template, 1 μl of 10 mM dNTP, 5 μl of 10× Pfu DNA polymerase buffer as supplied by the manufacturer, 25 pmol of fwd primer, 25 pmol of rev primer, 1 μl Pfu DNA polymerase in total volume 50 μl. After an initial denaturation step of 2 mins at 95 C, the reaction was subjected to 30 cycles of denaturation (95 C, 10 secs), annealing (55 C 10 secs), and elongation (72 C, 2 mins).

Beta Chain—C-Fos Leucine Zipper

The construct was made by PCR stitching.

For the 5'-end of the gene plasmids coding for the high affinity TCR beta chains and containing the introduced inter-chain di-sulfide bridge were used as template. PCR with the following two primers generated the desired variable domain gene fragment.

```
TRBV6-5 fwd
                                    (SEQ ID NO: 109)
tctctcattaatgaatgctggtgtcactcagacccc C-beta rev
                                    (SEQ ID NO: 110)
CTTCTGATGGCTCAAACACAGC
```

For the 3'-end of the gene the plasmid pEX205 (see FIG. 12), coding for a wild type affinity TCR beta chain fused to the human c-fos leucine zipper domain and not containing the code for the introduced inter-chain di-sulfide bridge, was used as template. PCR with the following two primers generated the desired constant domain gene fragment.

```
C-beta fwd
                                    (SEQ ID NO: 111)
GCTGTGTTTGAGCCATCAGAAG TRBC rev
                                    (SEQ ID NO: 112)
aagcttcccggggtctgctctaccccaggc
```

The two products were mixed and diluted 1000 fold and 1 μl was used as template in a 50 μl PCR with TRBV6-5 fwd and TRBC rev primers. PCRs were carried out as described above.

The resulting PCR product was digested using restriction enzymes AseI and XmaI and ligated into pEX205 cut with NdeI and XmaI.

EXAMPLE 4

Expression, Refolding and Purification of Soluble TCR

The expression plasmids containing the mutated α-chain and β-chain respectively as prepared in Examples 1, 2 or 3 were transformed separately into *E. coli* strain BL21pLysS, and single ampicillin-resistant colonies were grown at 37° C. in TYP (ampicillin 100 μg/ml) medium to $OD_{600}$ of 0.4 before inducing protein expression with 0.5 mM IPTG. Cells were harvested three hours post-induction by centrifugation for 30 minutes at 4000 rpm in a Beckman J-6B. Cell pellets were re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (Per-Bio).

Approximately 30 mg of TCR β chain and 60 mg of TCR α chain solubilised inclusion bodies were thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The redox couple (2-mercaptoethylamine and cystamine (to final concentrations of 6.6 mM and 3.7 mM, respectively) were added approximately 5 minutes before addition of the denatured TCR chains. The solution was left for 5 hrs±15 minutes. The refolded TCR was dialysed in Spectrapor 1 membrane (Spectrum; Product No. 132670) against 10 L 10 mM Tris pH 8.1 at 5° C.±3° C. for 18-20 hours. After this time, the dialysis buffer was changed to fresh 10 mM Tris pH 8.1 (10 L) and dialysis was continued at 5° C.±3° C. for another 20-22 hours.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions were stored at 4° C. and analysed by Coomassie-stained SDS-PAGE before being pooled and concentrated. Finally, the sTCR was purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

EXAMPLE 5

Biacore Surface Plasmon Resonance Characterisation of sTCR Binding to Specific pMHC A surface plasmon resonance biosensor (Biacore 3000™) was used to analyse the binding of a sTCR to its peptide-MHC ligand. This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Biotinylated class I HLA-A*0201 molecules were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15).

HLA-A*0201-heavy chain was expressed with a C-terminal biotinylation tag which replaces the transmembrane and cytoplasmic domains of the protein in an appropriate construct. Inclusion body expression levels of ~75 mg/liter bacterial culture were obtained. The MHC light-chain or β2-microglobulin was also expressed as inclusion bodies in *E. coli* from an appropriate construct, at a level of ~500 mg/liter bacterial culture.

*E. coli* cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter β2m into 0.4 M L-Arginine-HCl, 100 mM Tris pH 8.1, 3.7 mM cystamine, mM cysteamine, 4 mg/ml of the SLLMWITQC peptide required to be loaded by the HLA-A*0201 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient. HLA-A*0201-peptide complex eluted at approximately 250 mM NaCl, and peak fractions were collected, a cocktail of protease inhibitors (Calbiochem) was added and the fractions were chilled on ice.

Biotinylation tagged pMHC molecules were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 μg/ml BirA enzyme (purified according to O'Callaghan et al. (1999) *Anal. Biochem.* 266: 9-15). The mixture was then allowed to incubate at room temperature overnight.

The biotinylated pHLA-A*0201 molecules were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated pHLA-A*0201 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*0201 molecules were stored frozen at −20° C. Streptavidin was immobilised by standard amine coupling methods.

Such immobilised complexes are capable of binding both T-cell receptors and the coreceptor CD8αα, both of which may be injected in the soluble phase. Specific binding of TCR is obtained even at low concentrations (at least 40 μg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

The interactions between 1G4 sTCR containing a novel inter-chain bond and its ligand/MHC complex or an irrelevant HLA-peptide combination, the production of which is described above, were analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2m and streptavidin which have been chemically cross linked to the activated surface of the flow cells. The assay was then performed by passing sTCR over the surfaces of the different flow cells at a constant flow rate, measuring the SPR response in doing so.

To Measure Equilibrium Binding Constant

Serial dilutions of WT 1G4 sTCR were prepared and injected at constant flow rate of 5 μl min-1 over two different flow cells; one coated with ~1000 RU of specific SLLMWITQC (SEQ ID NO:126)-HLA-A*0201 complex, the second coated with ~1000 RU of non-specific HLA-A2-peptide complex. Response was normalised for each concentration using the measurement from the control cell. Normalised data response was plotted versus concentration of TCR sample and fitted to a hyperbola in order to calculate the equilibrium binding constant, $K_D$. (Price & Dwek, Principles and Problems in Physical Chemistry for Biochemists (2$^{nd}$ Edition) 1979, Clarendon Press, Oxford).

To Measure Kinetic Parameters

For high affinity TCRs $K_D$ was determined by experimentally measuring the dissociation rate constant, kd, and the association rate constant, ka. The equilibrium constant $K_D$) was calculated as kd/ka.

TCR was injected over two different cells one coated with ~300 RU of specific HLA-A2-nyeso peptide complex, the second coated with ~300 RU of non-specific HLA-A2-peptide complex. Flow rate was set at 50 μl/min. Typically 250 μl of TCR at ~3 μM concentration was injected. Buffer was then flowed over until the response had returned to baseline. Kinetic parameters were calculated using Biaevaluation software. The dissociation phase was also fitted to a single exponential decay equation enabling calculation of half-life.

Results

The interaction between a soluble disulfide-linked native 1G4 TCR (consisting of the α and β TCR chains detailed in SEQ ID NOs 9 and 10 respectively) and the SLLMWITQC (SEQ ID NO:126)-HLA-A*0201 complex was analysed using the above methods and demonstrated a $K_D$ of 15 μM and a $k_{off}$ of $1.28 \times 10^{-1}$ $S^{-1}$.

The TCRs specified in the following table have a $K_D$ of less than or equal to 1 μM and/or a $k_{off}$ of $1 \times 10^{-3}$ $S^{-1}$ or slower.

| Alpha chain variable domain sequence, SEQ ID NO: | Beta chain variable domain sequence, SEQ ID NO: |
|---|---|
| 1 | 84 |
| 1 | 85 |
| 1 | 86 |
| 1 | 87 |
| 1 | 88 |
| 11 | 84 |
| 12 | 84 |
| 12 | 85 |
| 12 | 90 |
| 11 | 85 |
| 11 | 86 |
| 11 | 92 |
| 11 | 93 |
| 13 | 86 |

| Alpha chain variable domain sequence, SEQ ID NO: | Beta chain variable domain sequence, SEQ ID NO: |
|---|---|
| 14 | 84 |
| 14 | 85 |
| 15 | 84 |
| 15 | 85 |
| 16 | 84 |
| 16 | 85 |
| 17 | 86 |
| 18 | 86 |
| 19 | 84 |
| 20 | 86 |
| 21 | 84 |
| 21 | 85 |
| 22 | 84 |
| 23 | 86 |
| 24 | 84 |
| 25 | 84 |
| 26 | 84 |
| 27 | 84 |
| 28 | 84 |
| 29 | 84 |
| 30 | 84 |
| 31 | 84 |
| 32 | 84 |
| 33 | 84 |
| 20 | 86 |
| 34 | 86 |
| 35 | 89 |
| 36 | 89 |
| 37 | 89 |
| 38 | 89 |
| 39 | 89 |
| 16 | 89 |
| 17 | 89 |
| 31 | 89 |
| 40 | 89 |
| 1 | 90 |
| 1 | 91 |
| 41 | 90 |
| 42 | 2 |
| 42 | 85 |
| 42 | 92 |
| 1 | 92 |
| 1 | 93 |
| 43 | 92 |
| 44 | 92 |
| 45 | 92 |
| 46 | 92 |
| 47 | 92 |
| 48 | 84 |
| 49 | 94 |
| 50 | 84 |
| 50 | 94 |
| 51 | 94 |
| 51 | 95 |
| 1 | 94 |
| 1 | 85 |
| 51 | 84 |
| 52 | 84 |
| 52 | 94 |
| 52 | 95 |
| 53 | 84 |
| 49 | 95 |
| 49 | 94 |
| 54 | 92 |
| 55 | 92 |
| 56 | 92 |
| 57 | 92 |
| 58 | 92 |
| 59 | 92 |
| 60 | 92 |
| 61 | 92 |
| 62 | 92 |
| 63 | 92 |
| 64 | 92 |
| 65 | 92 |
| 66 | 92 |
| 67 | 92 |
| 68 | 92 |
| 69 | 92 |
| 70 | 92 |
| 71 | 92 |
| 72 | 92 |
| 73 | 92 |
| 74 | 92 |
| 75 | 92 |
| 76 | 92 |
| 77 | 92 |
| 78 | 92 |
| 79 | 92 |
| 80 | 92 |
| 81 | 92 |
| 82 | 92 |
| 83 | 92 |
| 11 | 96 |
| 11 | 97 |
| 11 | 98 |
| 11 | 99 |
| 1 | 89 |
| 50 | 117 |
| 49 | 117 |
| 50 | 118 |
| 49 | 119 |
| 50 | 119 |
| 58 | 93 |
| 49 | 118 |
| 1 | 119 |
| 1 | 117 |
| 55 | 120 |
| 56 | 120 |
| 50 | 121 |
| 50 | 120 |
| 49 | 121 |
| 49 | 120 |
| 48 | 118 |
| 53 | 95 |

EXAMPLE 6

In-Vitro Cell Staining Using a High Affinity c58c61 NY-ESO TCR-IL-2 Fusion Protein T2 lymphoblastoid cells were pulsed with the NY-ESO-derived SLLMWITQC (SEQ ID NO:126), NY-ESO-analogue SLLMWITQV (SEQ ID NO:127) peptide, or an irrelevant peptide at a range of concentrations ($10^{-5}$-$10^{-10}$ M) for 180 minutes at 37° C. The NY-ESO-analogue SLLMWITQV (SEQ ID NO:127) peptide (V-variant peptide) was used as this peptide is known to have a higher affinity for the binding cleft of the HLA-A*0201 complex than the native NY-ESO-derived SLLMWITQC (SEQ ID NO:126) peptide. After pulsing, cells were washed in serum-free RPMI and $5 \times 10^5$ cells were incubated with high affinity c58c61 NY-ESO TCR-IL-2 fusion protein for 10 min at room temperature, followed by secondary anti-IL-2 mAb conjugated with PE (Serotec) for 15 min at room temperature. After washing, bound TCR-IL-2 was quantified by flow cytometry using a FACSVantage SE (Becton Dickinson). Controls, also using peptide-pulsed T2 cells were included where TCR-IL-2 was omitted.

FIG. 14a details the amino acid sequence of the alpha chain of the c58c61 NY-ESO TCR. (SEQ ID NO: 122).

FIG. 14c (SEQ ID NO: 124) details the amino acid sequence of the beta chain of the c58c61 NY-ESO TCR using the TRBC2 encoded constant region.

FIG. 14d (SEQ ID NO: 125) details the amino acid sequence of the beta chain of the c58c61 NY-ESO TCR using the TRBC2 encoded constant region fused via a peptide linker to wild-type human IL-2.

The alpha and beta chain variable domain mutations contained within the soluble c58c61 1G4 TCR-IL-2 fusion protein correspond to those detailed in SEQ ID NO: 49 and SEQ ID NO: 94 respectively. Note that SEQ ID NOs: 121-125 have been provided in a form which includes the N-terminal methionine (M) and the "K" and "NA" residues omitted in the majority of the other TCR alpha chain and beta chain amino acid sequences.

In similar experiments SK-MEL-37, ScaBER, J82, HcT119 and Colo 205 cancer cells transfected with a NY-ESO-derived SLLMWITQC (SEQ ID NO:126) peptide expressing ubiquitin minigene construct were used. The cancer cells were transfected using substantially the methods described in (Rimoldi et al., (2000) *J Immunol*. 165 7253-7261). Cells were labelled as described above.

Results

FIG. 15a shows FACs staining of T2 cell pulsed with a range of NY-ESO-analogue SLLMWITQV (SEQ ID NO:127) peptide concentrations using the high affinity c58c61 1G4 TCR-IL-2 fusion proteins.

FIG. 15a shows FACs staining of T2 cell pulsed with a range of NY-ESO-analogue SLLMWITQV (SEQ ID NO:127) peptide concentrations using the high affinity c58c61 1G4 TCR-IL-2 fusion proteins.

FIG. 15b shows FACs staining of T2 cell pulsed with a range of NY-ESO-derived SLLMWITQC (SEQ ID NO:126) peptide concentrations using the high affinity c58c61 1G4 TCR-IL-2 fusion proteins.

FIG. 16 shows FACs staining of SK-MEL-37, ScaBER, J82, HcT119 and Colo 205 cancer cells transfected with an SLLMWITQC (SEQ ID NO:126) peptide producing ubiquitin minigene (±proteosome inhibitors) using the high affinity c58c61 1G4 TCR-IL-2 fusion proteins.

EXAMPLE 9

CTL Activation ELISPOT Assay

The following assay was carried out to demonstrate that the soluble high affinity c58c61 NY-ESO TCR was capable of inhibiting activation of an SLLMWITQC (SEQ ID NO:126)-HLA-A*0201 specific CTL clone (1G4). IFN-γ production was used as the read-out for CTL activation.

Reagents

R10 Assay media: 10% FCS (heat-inactivated, Gibco, cat#10108-165), 88% RPMI 1640 (Gibco, cat#42401-018), 1% glutamine (Gibco, cat#25030-024) and 1% penicillin/streptomycin (Gibco, cat#15070-063).

Peptide: (obtained from various sources) initially dissolved in DMSO (Sigma, cat# D2650) at 4 mg/ml and frozen.

Wash buffer: 0.01M PBS/0.05% Tween 20 (1 sachet of Phosphate buffered saline with Tween 20, pH7.4 from Sigma, Cat. # P-3563 dissolved in 1 liter distilled water gives final composition 0.01M PBS, 0.138M NaCl, 0.0027M KCl, 0.05% Tween 20). PBS (Gibco, cat#10010-015).

The EliSpot kit contains all other reagents required i.e. capture and detection antibodies, skimmed milk powder, BSA, streptavidin-alkaline phosphatase, BCIP/NBT solution (Human IFN-g PVDF Eli-spot 20×96 wells with plates (IDS cat# DC-856.051.020, DC-856.000.000). The following method is based on the instructions supplied with each kit but contains some alterations.

MEL-624 and SK-MEL-37 melanoma cell lines were treated with trypsin for 5 minutes at 37° C. The cells are then washed and re-suspended in R10 media.

50000 target cells were then plated out per well in 50 μl of R10 media in a 96 well ELISPOT plate (Diaclone).

The following was then added to the above target cell cultures:

$1 \times 10^{-7}$M high affinity c58c61 TCR, or an irrelevant TCR, in 50 μl of R10 media.

600 SLLMWITQC (SEQ ID NO:126)-HLA-A*0201 specific T cells (clone 1G4) in 50 μl of R10 media.

These cultures were then incubated for 24 hours at 37° C., 5% $CO_2$. The ELISPOT plates were processed according to the manufacturers instructions.

Results

The soluble high affinity c58c61 1G4 TCR strongly inhibited the activation of 1G4 T cell clones against the melanoma cells, as measured by IFN-γ production. Whereas the irrelevant high affinity TCR had no inhibitory effect. (See FIG. 17 for MEL-624 cancer cell line results and FIG. 18 for SK-MEL-37 cancer cell line results)

EXAMPLE 10

CTL Activation ELISA Assay

The following assay was carried out to demonstrate that the soluble high affinity c58c61 1G4 TCR was capable of inhibiting activation of an SLLMWITQC-HLA-A*0201 specific CTL clone (1G4). IFN-γ production was used as the read-out for CTL activation.

Reagents

R10 Assay media: 10% FCS (heat-inactivated, Gibco, cat#10108-165), 88% RPMI 1640 (Gibco, cat#42401-018), 1% glutamine (Gibco, cat#25030-024) and 1% penicillin/streptomycin (Gibco, cat#15070-063).

Peptide: (obtained from various sources) initially dissolved in DMSO (Sigma, cat# D2650) at 4 mg/ml and frozen.

Wash buffer: 0.01M PBS/0.05% Tween 20 (1 sachet of Phosphate buffered saline with Tween 20, pH7.4 from Sigma, Cat. # P-3563 dissolved in 1 liter distilled water gives final composition 0.01M PBS, 0.138M NaCl, 0.0027M KCl, 0.05% Tween 20). PBS (Gibco, cat#10010-015).

The ELISA kit contains all other reagents except BSA (Sigma). required i.e. capture and detection antibodies, skimmed milk powder, streptavidin-HRP, TMB solution (Human IFN-g Eli-pair 20×96 wells with plates. The following method is based substantially on the instructions supplied with each kit.

Method

ELISA plates were prepared according to the manufacturers instructions. (Diaclone kit, Immunodiagnostic systems, UK T2 cell line target cells were washed and re-suspended in R10 media with or without varying concentrations (100 nM-10 pM) of SLLMWITQC (SEQ ID NO:126) peptide, then incubated for 1 hour at 37° C., 5% $CO_2$.

10,000 target cells per well were then plated out into a 96 well ELISA plate.

To these plates the following was added to the relevant well:

$1 \times 10^{-6}$M to $3 \times 10^{-12}$M of the high affinity c58c61 1G4 TCR or wild-type 1G4 TCR in 50 μl of R10 media.

5000 1G4 effector cells in 50 μl of R10 media.

The plates were then incubated for 48 hours at 37° C., 5% $CO_2$. The ELISA was then processed according to manufacturer's instructions.

Results

The soluble high affinity c58c61 1G4 TCR strongly inhibited the activation of 1G4 T cell clones against the peptide-pulsed target cells, as measured by IFN-γ production. Whereas the wild-type 1G4 TCR had no inhibitory effect. (See FIG. 19 for the high affinity c58c61 1G4 TCR and FIG. 20 for the wild-type 1G4 TCR)

EXAMPLE 11

In-Vivo Tumour Targeting Using a High Affinity c58c61 IG4 TCR-IL-2 Fusion Protein This work was carried out to investigate the ability of a high affinity c58c61 1G4 TCR-IL-2 fusion protein described in Example 6, to inhibit growth of human tumor cells engrafted in nude mice.

Fifty female nude mice (HARLAN, France) were used in this trial.

All animals were injected subcutaneously with the human melanoma tumour-forming cell line (SK-MEL-37) which had been stably transfected with a NY-ESO peptide/ubiquitin minigene construct in ensure enhanced expression of the appropriate class I-peptide target at the cell surface. Tumors were allowed to grow in the animals for 5 days to allow tumour development prior to commencement of treatment.

The rats then received the following i.v. bolus dosage of c58c61 high affinity NY-ESO TCR/IL-2 fusion protein:

Doses ranged between 0.02 and 1.0 mg/kg high affinity 1G4 TCR/IL-2 fusion proteins in PBS, administered at 5, 6, 7, 8, 11, 13, 17, 20, 24, 28, and 30 day post-tumor engraftment. In all experiments, a control treatment group was included where PBS alone was substituted for the TCR/IL-2 immunoconjugate.

Tumor size was then measured using callipers and tumor volume determined according to the following formula ($W^2 \times L$)/2, where W=the smallest diameter of the tumor, and L=is the longest diameter.

Results

The therapeutic effect of the TCR/IL-2 immunoconjugates in terms of tumor growth inhibition is shown in FIG. 21.

Conclusions

The TCR/IL-2 immunoconjugate exhibited a clear dose-dependent anti-tumor effect as shown by the tumour growth curves depicted in FIG. 21.

EXAMPLE 12

Quantification of Cell Surface TCR Ligands by Fluorescence Microscopy Using High Affinity c58c61 1G4 TCR The number of SLLMWITQC (SEQ ID NO:126)-HLA-A*0201 antigens on cancer cells (Mel 526, Mel 624 and SK-Mel-37 cell lines) was determined (on the assumption that one fluorescence signal relates to a single labelled TCR bound to its cognate pMHC ligand on the surface of the target cell) by single molecule fluorescence microscopy using the high-affinity c58c61 1G4 TCR. This was facilitated by using biotinylated TCR to target the antigen-expressing cancer cells and subsequent labelling of cell-bound TCR by streptavidin-R phycoerythrin (PE) conjugates. Individual PE molecules were then imaged by 3-dimensional fluorescence microscopy.

Staining of Adherent Cells.

The cancer cells were plated into chamber well slides and allowed to adhere overnight in incubator. (37° C., 5% $CO_2$) Media was removed and replaced with fresh R10. Media was removed, and cells washed twice with 500 µl of PBS supplemented with 400 µM $MgCl_2$ (PBS/Mg). Cells were incubated in 200 µl of TCR solution (5 µg ml$^{-1}$ high affinity c58c61 1G4 TCR, or 5 µg ml$^{-1}$ of an "irrelevant" HLA-A2-tax peptide-specific high affinity TCR, in PBS/Mg containing 0.5% BSA albumin) for 30 min at 4° C. TCR solution was removed, and cells were washed three times with 500 µl of PBS/Mg. Cells were incubated in 200 µl of streptavidin-PE solution (5 µg ml$^{-1}$ streptavidin-PE in PBS/Mg containing 0.5% BSA) at room temperature in the dark for 20 min. Streptavidin-PE solution was removed and cells were washed five times with 500 µl of PBS/Mg. Wash media was removed, and cells kept in 400 µl of imaging media before imaging by fluorescence microscopy.

Fluorescence Microscopy.

Fluorescent microscopy was carried out using an Axiovert 200M (Zeiss) microscope with a 63× Oil objective (Zeiss). A Lambda LS light source containing a 300 W Xenon Arc lamp (Sutter) was used for illumination, and light intensity was reduced to optimal levels by placing a 0.3 and a 0.6 neutral density filter into the light path. Excitation and emission spectra were separated using a TRITC/DiI filter set (Chroma). Cells were imaged in three dimensions by z-stack acquisition (21 planes, 1 µm apart). Image acquisition and analysis was performed using Metamorph software (Universal Imaging) as described (Irvine et al., Nature (419), p 845-9, and Purbhoo et al., Nature Immunology (5), p 524-30).

Results

As demonstrated by FIG. 22 the above method was used successfully to image high affinity 1G4 TCR bound to SLL-MWITQC (SEQ ID NO:126)-HLA-A*0201 antigens on the surface of Mel 526, Mel 624 and SK-Mel-37 cancer cells.

The invention claimed is:

1. A recombinant TCR having the α chain extracellular sequence SEQ ID NO: 1 and the β chain extracellular sequence SEQ ID NO: 2 except that amino acids Q51 and S53 of SEQ ID NO: 1 are replaced by 51M and 53H and amino acid G50 of SEQ ID NO: 2 is replaced by 50S.

2. A pharmaceutical composition comprising: a plurality of cells having the TCR of claim 1; and a pharmaceutically acceptable carrier.

3. A recombinant TCR having the α chain extracellular sequence SEQ ID NO: 1 and the β chain extracellular sequence SEQ ID NO: 2 except that amino acids Q51 and S53 of SEQ ID NO: 1 are replaced by 51M and 53H and amino acid A51 of SEQ ID NO: 2 is replaced by 51V.

4. A pharmaceutical composition comprising: a plurality of cells having the TCR of claim 3; and a pharmaceutically acceptable carrier.

5. A recombinant TCR having the α chain extracellular sequence SEQ ID NO: 5 and the β chain extracellular sequence SEQ ID NO: 6 except that amino acids Q51 and S53 of SEQ ID NO: 5 are replaced by 51M and 53H and amino acid A51 of SEQ ID NO: 6 is replaced by 51V and amino acid T162 of the α chain and amino acid S169 of the β chain are replaced by 162C and 169C and comprising a disulfide bond between α chain 162C and β chain 169C, using the numbering of SEQ ID NOs: 5 and 6.

6. An isolated cell having a TCR having the α chain extracellular sequence SEQ ID NO: 1 and the β chain extracellular sequence SEQ ID NO: 2 except that amino acids Q51 and S53 of SEQ ID NO: 1 are replaced by 51M and 53H and amino acid G50 of SEQ ID NO: 2 is replaced by 50S.

7. An isolated cell having a TCR having the α chain extracellular sequence SEQ ID NO:5 and the β chain extracellular sequence SEQ ID NO: 6 except that amino acids Q51 and S53 of SEQ ID NO: 5 are replaced by 51M and 53H and amino acid G50 of SEQ ID NO: 6 is replaced by 50S and amino acid T162 of the α chain and amino acid S169 of the β chain are replaced by 162C and 169C and comprising a disulfide bond between α chain 162C and β chain 169C, using the numbering of SEQ ID NOs: 5 and 6.

8. An isolated cell having a TCR having the α chain extracellular sequence SEQ ID NO: 1 and the β chain extracellular sequence SEQ ID NO: 2 except that amino acids Q51 and S53 of SEQ ID NO: 1 are replaced by 51M and 53H and amino acid A51 of SEQ ID NO: 2 is replaced by 51V.

9. An isolated cell having a TCR having the α chain extracellular sequence SEQ ID NO: 5 and the chain extracellular sequence SEQ ID NO: 6 except that amino acids Q51 and S53 of SEQ ID NO: 5 are replaced by 51M and 53H and amino acid A51 of SEQ ID NO: 6 is replaced by 51V and amino acid T162 of the α chain and amino acid S169 of the β chain are replaced by 162C and 169C and comprising a disulfide bond between α chain 162C and β chain 169C, using the numbering of SEQ ID NOs: 5 and 6.

* * * * *